United States Patent [19]

Ooki et al.

[11] Patent Number: 5,764,363
[45] Date of Patent: Jun. 9, 1998

[54] APPARATUS FOR OBSERVING A SURFACE USING POLARIZED LIGHT

[75] Inventors: Hiroshi Ooki; Yutaka Iwasaki; Jun Iwasaki, all of Yokohama; Tsuneyuki Hagiwara, Tokyo, all of Japan

[73] Assignee: Nikon Corporation, Tokyo, Japan

[21] Appl. No.: 672,331

[22] Filed: Jun. 28, 1996

[30] Foreign Application Priority Data

| Jun. 30, 1995 | [JP] | Japan | 7-188509 |
| Jun. 30, 1995 | [JP] | Japan | 7-188510 |
| Jun. 30, 1995 | [JP] | Japan | 7-188511 |
| Aug. 24, 1995 | [JP] | Japan | 7-215580 |
| Aug. 25, 1995 | [JP] | Japan | 7-217915 |
| Nov. 20, 1995 | [JP] | Japan | 7-301579 |
| Nov. 20, 1995 | [JP] | Japan | 7-301580 |

[51] Int. Cl.$^6$ ................................. G01J 4/00
[52] U.S. Cl. .............. 356/364; 356/369; 359/385; 359/386
[58] Field of Search .................. 356/364, 365, 356/366, 367, 368, 369, 351, 352, 237, 317, 445; 359/385, 386, 387, 388, 389, 390, 368, 369, 370, 371; 354/434; 250/563, 572

[56] References Cited

U.S. PATENT DOCUMENTS

| 2,601,175 | 6/1952 | Smith. | |
| 4,037,929 | 7/1977 | Bricot et al. | 350/160 |
| 4,298,283 | 11/1981 | Makosch et al. | |

(List continued on next page.)

FOREIGN PATENT DOCUMENTS

| 0634682 A2 | 1/1995 | European Pat. Off. |
| 3136887 A1 | 3/1983 | Germany. |
| 3240234 A1 | 5/1983 | Germany. |
| 2428810 C2 | 12/1984 | Germany. |

(List continued on next page.)

OTHER PUBLICATIONS

"Quantitative surface topography determination by Nomarski reflection microscopy. I. Theor", Lessor et al., J. Opt. Soc. Am., vol. 69, No. 2, Feb. 1979, pp. 357–366.

Bristow, Non–Contact Surface Roughness Meter "MP2000", O Plus E, No. 155, 1992, pp. 70–72. (Translation).

Iwasaki et al. "Differential Detection of Differential Interference Contrast Microscope and Its Application", Proceedings of 16th Meeting of Japan Society for Laser Microscopy, 1995, pp. 63–67. (Translation).

(List continued on next page.)

*Primary Examiner*—Frank G. Font
*Assistant Examiner*—Michael P. Stafira
*Attorney, Agent, or Firm*—Foley & Lardner

[57] ABSTRACT

An observation apparatus of the present comprises (i) a light source for generating light; (ii) a separating optical system which splits the light from the light source into two different polarized light beams; (iii) a condenser optical system which converges the two polarized light beams from the separating optical system so as to respectively form light spots on two different positions on a sample object; (iv) a polarization selecting means which has a predetermined analyzer angle and selects a specific polarized light component from composite light made of the two polarized light beams by way of the sample object; (v) light detecting means which detects the polarized light component selected by the polarization selecting means; and (vi) phase difference adjustment means which adjusts a phase difference between the two polarized light beams by way of the sample object and guides composite light composed of the two polarized light beams as circularly polarized light to the polarization selecting means, when the sample object does not modulate both phase and amplitude of the light incident thereon. Accordingly, this observation apparatus can detect a phase difference generated between the two light components respectively emitted from both side of a level difference on the sample object.

104 Claims, 25 Drawing Sheets

U.S. PATENT DOCUMENTS

| | | |
|---|---|---|
| 4,456,339 | 6/1984 | Sommargren . |
| 4,841,510 | 6/1989 | Yoshizawa ........................ 369/46 |
| 5,311,284 | 5/1994 | Nishino .......................... 356/364 |
| 5,457,536 | 10/1995 | Kornfield et al. ............... 356/366 |
| 5,479,252 | 12/1995 | Worster et al. ................. 356/237 |
| 5,572,359 | 11/1996 | Otaki et al. .................... 359/386 |
| 5,604,591 | 2/1997 | Kitagawa ........................ 356/351 |

FOREIGN PATENT DOCUMENTS

| | | |
|---|---|---|
| 3918412 A1 | 2/1990 | Germany . |
| 3803181 C2 | 7/1990 | Germany . |
| 3942896 A1 | 6/1991 | Germany . |
| 4124223 A1 | 1/1993 | Germany . |
| 4242883 A1 | 6/1994 | Germany . |
| 4311726 A1 | 1/1995 | Germany . |
| 4192191 C1 | 10/1995 | Germany . |
| 4434473 A1 | 3/1996 | Germany . |
| 07253545 A | 3/1995 | Japan . |
| 08122648 A | 5/1996 | Japan . |

OTHER PUBLICATIONS

Bristow et al, "Surface Measurements and Applications for Manufactured Parts Using Noncontact Profilometer", SPIE, vol. 954, Optical Testing and Metrology II, 1988, pp. 217–225.

Ooki et al, "Differential interference contrast microscope with differential detection for optimizing image contrast", Applied Optics, vol. 35, No. 13, 1996, pp. 2230–2234.

APPARATUS FOR OBSERVING A SURFACE USING POLARIZED LIGHT

BACKGROUND OF THE INVENTION

1. Field of the Invention

The present invention relates to an observation apparatus suitable for observing IC patterns and metal surfaces in particular and, more specifically, to that used as a differential interference microscope which forms a differential interference image reflecting the distribution of minute level differences existing in their surface structures, and as a level-difference measuring apparatus for quantitatively measuring these minute level differences, or the like.

Also, the present invention relates to an observation apparatus suitable for observing a reticle having a light-shielding circuit pattern or a reticle with phase shifters used in manufacturing a semiconductor or liquid crystal substrate (including a reticle having both a light-shielding circuit pattern and a circuit pattern as a phase object) in particular and, more specifically, to that used as a differential interference microscope which can observe defects in the circuit pattern or in phase shifter, and foreign substances (defects) adhering to the reticle, and as a defect inspection apparatus for inspecting defects in the circuit pattern or in the phase shifter, and foreign substances on the reticle.

2. Related Background Art

As disclosed in Japanese Unexamined Patent Publication No. 3-91709 corresponding to an application of the assignee, there has been known a conventional laser scanning type differential interference microscope in which the configuration of a known imaging type differential interference microscope is transferred to a laser scanning optical system. The laser scanning type differential interference microscope can yield advantages inherent in a laser scanning microscope such as minimized flares, while attaining a differential interference image in which the influence of change in reflectivity on a sample object is suppressed.

Also, as disclosed in *O plus E*, October 1992, pp. 70–72, there has been known a conventional non-contact surface roughness meter in which, while a laser scanning type differential interference microscope is adopted, a polarizing beam splitter is used in place of the conventional analyzer. The non-contact surface roughness meter disclosed in this journal detects the transmitted light and reflected light from the polarizing beam splitter at the same time and, based on the ratio of the difference signal between the detected signal of the transmitted light and the detected signal of the reflected light to their sum signal, measures a level difference on the sample object so as to suppress the influence on the image caused by the change in reflectivity of the sample object.

The above-mentioned journal states that the sum signal is not influenced by the level difference. However, a level difference is not considerably influential to the sum signal only when the phase difference of light generated by the level difference is very small. As the level difference increases, the sum signal is also modulated by diffraction.

Further, a conventional defect inspection apparatus for a reticle with phase shifters is an apparatus for measuring the phase amount of a phase shifter, as described in, e.g., "Photomask and X-ray Mask technology," SPIE, Proceedings series Volume 2254, pp. 294–301. The apparatus measures a phase amount at one sampling point in the field of an optical microscope while positioning the phase shifter portion to be inspected in the reticle in the field of the optical microscope.

SUMMARY OF THE INVENTION

An object of the present invention is to provide an observation apparatus which can detect, with high sensitivity, a phase difference generated between two light components respectively traveled through both sides of a level difference on a sample object.

Also, an object of the present invention is to provide an observation apparatus configured as a differential interference microscope which can adjust the contrast of an interference image reflecting the level difference on the sample object so as to set an optimal contrast for the differential interference image.

Also, an object of the present invention is to provide an observation apparatus configured as a level-difference measuring apparatus which can quantitatively measure a level difference on a sample object with high accuracy even when light reflectivity changes between both sides of the level difference.

Also, an object of the present invention is to provide an observation apparatus configured as a defect inspection apparatus which can inspect defects in phase difference amounts of all phase shifters in a reticle with phase shifters within a short time and also detect contaminants (defects) in a circuit pattern of the reticle, such as foreign substances interfering with an exposure operation.

Further, an object of the present invention is to provide an observation apparatus configured as a defect inspection apparatus which can detect transparent foreign substances on a reticle with a high sensitivity.

In order to attain the above-mentioned objects, the observation apparatus in accordance with one aspect of the present invention comprises (i) a light source for generating light; (ii) a separating optical system which splits the light emitted from the light source into two different polarized light beams; (iii) a condenser optical system which converges the two polarized light beams emitted from the separating optical system so as to respectively form light spots on two different positions on a sample object; (iv) a polarization selecting means which has a predetermined analyzer angle and selects a specific polarized light component from composite light made of the two polarized light beams reflected by or transmitted through the sample object; (v) light detecting means which detects the polarized light component selected by the polarization selecting means; and (vi) phase difference adjustment means which adjusts a phase difference between the two polarized light beams reflected by or transmitted through the sample object and guides composite light composed of the two polarized light beams as circularly polarized light to the polarization selecting means, when the sample object does not modulate both the phase and amplitude of the light incident thereon.

Here, preferably, the observation apparatus of the present invention further comprises a scanning device for scanning the sample object with the two light spots thereon which are split by the separating optical system, while the light source generates spatially coherent light and guides thus generated light to the separating optical system.

In this case, desirably, in the observation apparatus of the present invention, the light source generates linearly polarized light having a predetermined direction of polarization; when the sample object is a light reflecting member having a mirror surface, the phase difference adjustment means imparts a phase difference of $\pi$ multiplied by an integer to the two polarized light beams split by the separating optical system and then reflected by the sample object, as the two polarized light beams travel through the separating optical system to-and-fro; and the phase difference adjustment means includes a ¼-wavelength plate which converts the linearly polarized light emitted from the separating optical system into the circularly polarized light.

Also, desirably, in the observation apparatus of the present invention, the light source generates linearly polarized light having a predetermined direction of polarization; when the sample object is a light reflecting member having a mirror surface, the phase difference adjustment means imparts a phase difference of $\pi/2$ multiplied by an odd number to the two polarized light beams split by the separating optical system and then reflected by the sample object, as the two polarized light beams travel through the separating optical system to-and-fro.

Also, desirably, the observation apparatus of the present invention further comprises a synthesizing optical system which combines the two polarized light beams transmitted through the sample object and guides the composite light to the polarization selecting means; the light source generates linearly polarized light having a predetermined direction of polarization; when the sample object is an optical flat light transmitting member, the phase difference adjustment means imparts a phase difference of $\pi$ multiplied by an integer to the two polarized light beams split by the separating optical system and then transmitted through the sample object; and wherein the phase difference adjustment means includes a ¼-wavelength plate which converts the linearly polarized light emitted from the synthesizing optical system into the circularly polarized light.

Further, desirably, the observation apparatus of the present invention further comprises a synthesizing optical system which combines the two polarized light beams transmitted through the sample object and guides the composite light to the polarization selecting means; the light source generates linearly polarized light having a predetermined direction of polarization; and when the sample object is an optically flat light transmitting member, the phase difference adjustment means imparts a phase difference of $\pi/2$ multiplied by an odd number to the two polarized light beams split by the separating optical system and then transmitted through the sample object.

Also here, preferably, the observation apparatus of the present invention further comprises an illumination optical system which is disposed between the light source and the separating optical system and illuminates the sample object with the light thereon emitted from the light source by way of the separating optical system; the light detecting means is constituted by two-dimensional image sensor disposed on at least one of respective focal planes of the condenser optical system.

In this case, desirably, in the observation apparatus of the present invention, the illumination optical system includes a wavelength selecting means for selecting a specific wavelength component from the light emitted from the light source. Also, desirably, in the observation apparatus of the present invention, the illumination optical system includes a polarized light selecting means for selecting a specific linear polarized light component from the light emitted from the light source.

More desirably, in the observation apparatus of the present invention, when the sample object is a light reflecting member having a mirror surface, the phase difference adjustment means imparts a phase difference of $\pi$ multiplied by an integer to the two polarized light beams split by the separating optical system and then reflected by the sample object, as the two polarized light beams travel through the separating optical system to-and-fro; the phase difference adjustment means includes a ¼-wavelength plate which converts the linearly polarized light emitted from the separating optical system into the circularly polarized light.

Also, more desirably, in the observation apparatus of the present invention, when the sample object is a light reflecting member having a mirror surface, the phase difference adjustment means imparts a phase difference of $\pi/2$ multiplied by an odd number to the two polarized light beams split by the separating optical system and then reflected by the sample object, as the two polarized light beams travel through the separating optical system to-and-fro.

Also, more desirably, the observation apparatus of the present invention further comprises a synthesizing optical system which combines the two polarized light beams transmitted through the sample object and guides the composite light to the polarization selecting means; when the sample object is an optically flat light transmitting member, the phase difference adjustment means imparts a phase difference of $\pi$ multiplied by an integer to the two polarized light beams split by the separating optical system and then transmitted through the sample object; and the polarization selecting means includes a ¼-wavelength plate which converts the linearly polarized light emitted from the synthesizing optical system into the circularly polarized light.

Further, more desirably, the observation apparatus of the present invention further comprises a synthesizing optical system which combines the two polarized light beams transmitted through the sample object and guides the composite light to the polarization selecting means; when the sample object is an optically flat light transmitting member, the phase difference adjustment means imparts a phase difference of $\pi/2$ multiplied by an odd number to the two polarized light beams split by the separating optical system and then transmitted through the sample object.

Also here, preferably, in the observation apparatus of the present invention, the condenser optical system is arranged so as to serve as an objective optical system which collects the two polarized light beams reflected by the sample object, and the separating optical system is arranged so as to serve as a synthesizing optical system which combines the two polarized light beams again exited from the condenser optical system and guides the composite light to the polarization selecting means.

In this case, desirably, in the observation apparatus of the present invention, the separating optical system includes a birefringence prism. Also, desirably, in the observation apparatus of the present invention, the separating optical system includes a prism having two reflecting surfaces non-parallel to each other, and a polarizing beam splitter surface disposed between the two reflecting surfaces and parallel to either of the two reflecting surfaces.

Also, desirably, in the observation apparatus of the present invention, the separating optical system includes two mirrors having respective reflecting surfaces non-parallel to each other, and two prisms disposed between the two mirrors and having respective polarizing beam splitter surfaces parallel to either of the reflecting surfaces of two reflecting mirrors. Also, desirably, in the observation apparatus of the present invention, the phase difference adjustment means comprises a driving member capable of moving the separating optical system.

Also, preferably, the observation apparatus of the present invention further comprises an objective optical system which collects the two polarized light beams transmitted through the sample object, and a synthesizing optical system which combines the two polarized light beams emitted from the objective optical system and guides the composite light to the polarization selecting means.

In this case, desirably, in the observation apparatus of the present invention, at least one of the separating optical system and the synthesizing optical system includes a birefringence prism. Also, desirably, in the observation apparatus of the present invention, at least one of the separating optical system and the synthesizing optical system includes a prism having two reflecting surfaces non-parallel to each other, and a polarizing beam splitter surface disposed between the two reflecting surfaces and parallel to either of the two reflecting surfaces.

Also, desirably, in the observation apparatus of the present invention, at least one of the separating optical system and the synthesizing optical system includes two mirrors having respective reflecting surfaces non-parallel to each other, and two prisms disposed between the two mirrors and having respective polarizing beam splitter surfaces parallel to either of the reflecting surfaces of two reflecting mirrors. Further, desirably, in the observation apparatus of the present invention, the phase difference adjustment means comprises a driving member capable of moving at least one of the separating optical system and the synthesizing optical system.

Also, here, preferably, the observation apparatus of the present invention further comprises a measuring means for quantitatively measuring, based on an output of the light detecting means, a level difference on the sample object; the polarization selecting means includes a polarizing beam splitter which splits the composite light composed of the two polarized light beams reflected by or transmitted through the sample object into two different directions; the light detecting means includes a first photodetector for detecting the polarized light transmitted through the polarizing beam splitter and a second photodetector for detecting the polarized light reflected by the polarizing beam splitter; and the measuring means measures the level difference of the sample object based on a relationship which is established between an output difference in the first and second photodetectors for the level difference of the sample object and a phase difference in the two polarized light beams caused by the level difference of the sample object, while depending on change in amplitude reflectance between two regions holding the level difference of the sample object therebetween.

In this case, desirably, in the observation apparatus of the present invention, the analyzer angle of the polarization selecting means is set to $n\pi/4$ as the analyzer angle of the polarizing beam splitter wherein n is an odd number. Also, desirably, in the observation apparatus of the present invention, the measuring means measures the level difference of the object sample based on a phase difference $\Psi$ between the two polarized light beams calculated by the following relationship:

$$\sin \Psi = D \cdot S / (W_a^{1/2} \cdot W_b^{1/2})$$

wherein $\Psi$ is the phase difference between the two polarized light beams caused by the level difference of the sample object, S is an output difference between the first and second photodetectors, $W_a$ is an output sum of the first and second photodetectors for one of two regions holding the level difference of the sample object therebetween reflecting amplitude reflectance of the region, $W_b$ is an output sum of the first and second photodetectors for the other of the two regions holding the level difference of the sample object therebetween reflecting amplitude reflectance of the other region, and D is a constant depending on the apparatus as a whole.

Also here, preferably, the observation apparatus of the present invention further comprises a measuring means for quantitatively measuring, based on an output of the light detecting means, a level difference on the sample object; the polarization selecting means variably sets the analyzer angle with respect to the composite light composed of the two polarized light beams reflected by or transmitted through the sample object; and the measuring means measures the level difference of the sample object based on a relationship which is established between an output difference in the light detecting means for the level difference of the sample object when two different analyzer angles for the polarization selecting means are respectively set and a phase difference in the two polarized light beams caused by the level difference of the sample object, while depending on change in amplitude reflectance between two regions holding the level difference of the sample object therebetween.

In this case, desirably, in the observation apparatus of the present invention, the polarization selecting means includes a polarizing plate which is disposed so as to be rotatable around an optical axis of the condenser optical system. Also, desirably, in the observation apparatus of the present invention, the polarization selecting means includes a liquid crystal polarizer which changes a refractive index distribution thereof based on a voltage signal externally applied thereto. Also, desirably, in the observation apparatus of the present invention, the analyzer angles of the polarization selecting means are set to $n\pi/4$ and $(n/4+m/2)\pi$, respectively, wherein n and m are odd numbers.

Further, desirably, in the observation apparatus of the present invention, the measuring means measures a level difference of the object surface based on a phase difference $\Psi$ between the two polarized light beams calculated by the following relationship:

$$\sin \Psi = D \cdot S / (W_a^{1/2} \cdot W_b^{1/2})$$

wherein $\Psi$ is the phase difference between the two polarized light beams caused by the level difference of the sample object, S is an output difference in the light detecting means when two analyzer angles for the polarization selecting means are set, $W_a$ is an output sum of the light detecting means for one of two regions holding the level difference of the sample object therebetween reflecting amplitude reflectance of this region, $W_b$ is an output sum of the light detecting means for the other of the two regions holding the level difference of the sample object therebetween reflecting amplitude reflectance of the other region, and D is a constant depending on the apparatus as a whole.

Also here, preferably, the observation apparatus of the present invention further comprises a measuring means for quantitatively measuring, based on an output of the light detecting means, a level difference on the sample object; the polarization selecting means variably sets the analyzer angle with respect to the composite light composed of the two polarized light beams reflected by or transmitted through the sample object and includes a polarizing beam splitter which splits the composite light into two different directions; the light detecting means includes a first photodetector for detecting light transmitted through the polarizing beam splitter and a second photodetector for detecting light reflected by the polarizing beam splitter; and the measuring means measures the level difference of the sample object based on the analyzer angle which is set so as to maximize or minimize the output difference between the first and second photodetectors for the level difference of the sample object.

In this case, desirably, in the observation apparatus of the present invention, the polarizing beam splitter is fixed around an optical axis of the condenser optical system and wherein the polarization selecting means includes an azimuth rotator disposed on an inlet side of the polarizing beam splitter, the azimuth rotator having a variable polarization rotational angle. More desirably, in the observation apparatus of the present invention, the azimuth rotator is constituted by a ½-wavelength plate disposed so as to be rotatable around the optical axis of the condenser optical system.

Also, desirably, in the observation apparatus of the present invention, each of the polarizing beam splitter and the first and second photodetectors is disposed so as to be rotatable around the optical axis of the condenser lens. Also, desirably, in the observation apparatus of the present invention, an analyzer angle $\phi_{min}$ of the polarization selecting means when the output difference between the first and second photodetectors for the level difference of the sample object is minimum, coincides with $\phi_{max}+n\pi/4$, wherein $\phi_{max}$ is an analyzer angle of the polarization selecting means when the output difference between the first and second photodetectors for the level difference of the sample object is maximum, and n is an odd number.

Further, desirably, in the observation apparatus of the present invention, the measuring means measures a level difference of the object sample based on a phase difference $\Psi$ between the two polarized light beams calculated by the following relationship:

$$\tan 2\phi = -2a \cdot b \cdot \sin \Psi/(a^2-b^2)$$

wherein $\phi$ is the analyzer angle of the polarization selecting means when the output difference between the first and second photodetectors for the level difference of the sample object is maximum, $\Psi$ is the phase difference between the two polarized light beams caused by the level difference of the sample object, a is an amplitude reflectance of one of two regions holding the level difference of the sample object therebetween incorporated in an output sum of the light detecting means for the region, and b is an amplitude reflectance of the other of two regions holding the level difference of the sample object therebetween incorporated in an output sum of the light detecting means for the other region.

Also here, in the observation apparatus of the present invention further comprises a measuring means for quantitatively measuring, based on an output of the light detecting means, a level difference on the sample object; the polarization selecting means variably sets the analyzer angle with respect to the composite light composed of the two polarized light beams reflected by or transmitted through the sample object and wherein the measuring means measures the level difference of the sample object based on two different analyzer angles which are set so as to maximize and minimize the output difference between the light detecting means for the level difference of the sample object.

In this case, desirably, in the observation apparatus of the present invention, the polarization selecting means includes a polarizing plate which is disposed so as to be rotatable around the optical axis of the condenser optical system. Also, desirably, in the observation apparatus of the present invention, the polarization selecting means includes a liquid crystal polarizer which changes a refractive index distribution thereof based on a voltage signal externally applied thereto. Also, desirably, in the observation apparatus of the present invention, a difference in the two analyzer angles of the polarization selecting means is set to $n\pi/4$, wherein n is an odd number.

Further, desirably, in the observation apparatus of the present invention, the measuring means measures a level difference of the object sample based on a phase difference $\Psi$ between the two polarized light beams calculated by the following relationship:

$$\tan 2\phi = -2a \cdot b \cdot \sin \Psi/(a^2-b^2)$$

wherein $\Psi$ is the phase difference between the two polarized light beams caused by the level difference of the sample object, a is an amplitude reflectance of one of two regions holding the level difference of the sample object therebetween incorporated in an output sum of the light detecting means for the region and b is an amplitude reflectance of the other of the two regions holding the level difference of the sample object therebetween incorporated in an output sum of the light detecting means for the other region when the two analyzer angles for the polarization selecting means are respectively set to $\phi$ and $\phi+\pi/2$ so that the output difference between the light detecting means for the level difference of the sample object is maximum, or when the two analyzer angles for the polarization selecting means are respectively set to $\phi+\pi/4$ and $\phi+3\pi/4$ so that the output difference between the light detecting means for the level difference of the sample object is minimum.

Also here, preferably, the observation apparatus of the present invention further comprises an image forming means which forms a differential interference image of the sample object based on an output of the light detecting means; the polarization selecting means variably sets the analyzer angle with respect to the composite light composed of the two polarized light beams reflected by or transmitted through the sample object and includes a polarizing beam splitter which splits the composite light into two different directions; the light detecting means includes a first photodetector for detecting light transmitted through the polarizing beam splitter and a second photodetector for detecting light reflected by the polarizing beam splitter; and the image forming means generates, based on an output difference between the first and second photodetectors for the level difference of the sample object, a contrast corresponding to the analyzer angle of the polarization selecting means for the differential interference image of the sample object.

In this case, desirably, in the observation apparatus of the present invention, the polarizing beam splitter is fixed around an optical axis of the condenser optical system and wherein the polarization selecting means includes an azimuth rotator which is disposed on an inlet side of the polarizing beam splitter, the azimuth rotator having a variable polarization rotational angle. More desirably, in the observation apparatus of the present invention, the azimuth rotator is constituted by a ½-wavelength plate disposed so as to be rotatable around the optical axis of the condenser optical system.

Also, desirably, in the observation apparatus of the present invention, each of the polarizing beam splitter and the first and second photodetectors is disposed so as to be rotatable around the optical axis of the condenser optical system. Also, desirably, in the observation apparatus of the present invention, the analyzer angle of the polarization selecting means is set to $n\pi/4$ wherein n is an odd number.

Also here, preferably, the observation apparatus of the present invention further comprises an image forming means which forms a differential interference image of the sample object based on an output of the light detecting means; the polarization selecting means variably sets the analyzer angle with respect to the composite light composed of the two polarized light beams reflected by or transmitted through the sample object; and the image forming means generates, based on an output difference in the light detecting means for the level difference of the sample object when two different analyzer angles for the polarization selecting means are respectively set, a contrast corresponding to the analyzer angle of the polarization selecting means for the differential interference image of the sample object.

In this case, desirably, in the observation apparatus of the present invention, the polarization selecting means includes a polarizing plate which is disposed so as to be rotatable around the optical axis of the condenser optical system. Also, desirably, in the observation apparatus of the present invention, the polarization selecting means includes a liquid crystal polarizer which changes a refractive index distribution thereof based on a voltage signal externally applied thereto. Further, desirably, in the observation apparatus of the present invention, a difference in the two analyzer angles of the polarization selecting means is set to $n\pi/4$, wherein n is an odd number.

Also here, preferably, the observation apparatus of the present invention further comprises a defect detection system which detects the defect formed on a substrate being the sample object on the basis of an output from the light detecting means; the polarization selecting means variably sets the analyzer angle with respect to the composite light composed of the two polarized light beams emitted from the sample object and includes a polarizing beam splitter which splits the composite light into two different directions; the light detecting means includes a first photodetector for detecting light transmitted through the polarizing beam splitter and a second photodetector for detecting light reflected by the polarizing beam splitter; and the defect detecting means shows the defects as the differential interference image of the sample object generated with a contrast corresponding to the analyzer angle of the polarization selecting means, based on an output difference between the first and second photodetectors.

In this case, desirably, in the observation apparatus of the present invention, the light source emits a linearly polarized light beam having a wavelength of light for which a phase shift of $\pi$ multiplied by an integer is caused by a transparent substance constituting a predetermined pattern on the substrate or a wavelength substantially equal to a wavelength of light used to expose the predetermined pattern.

Also, desirably, in the observation apparatus of the present invention, the defect detection system comprises a differential circuit which generates a difference signal as the difference of two output signals respectively input from the first and second photodetectors, corresponding the two different polarized light beams selected by the polarization selecting means, a binaring circuit which compares the difference signal from the differential circuit with a predetermined threshold value thereby generating a binary signal, and a judging circuit which detects the defects formed on the substrate on the basis of the binary signal from the binaring circuit.

Also, desirably, in the observation apparatus of the present invention, the polarizing beam splitter is fixed around an optical axis of the condenser optical system and the polarization selecting means includes an azimuth rotator which is disposed on an inlet side of the polarizing beam splitter, the azimuth rotator having a variable polarization rotational angle. More desirably, in the observation apparatus of the present invention, the azimuth rotator is constituted by a ½-wavelength plate disposed so as to be rotatable around the optical axis of the condenser optical system.

Also, desirably, in the observation apparatus of the present invention, each of the polarizing beam splitter and the first and second photodetectors is disposed so as to be rotatable around the optical axis of the condenser optical system. Further, desirably, in the observation apparatus of the present invention, the analyzer angle of the polarization selecting means is set to $n\pi/4$ wherein n is an odd number.

Further here, preferably, the observation apparatus of the present invention further comprises a defect detection system which detects the defect formed on a substrate being the sample object on the basis of an output from the light detecting means; the polarization selecting means variably sets the analyzer angle with respect to the composite light composed of the two polarized light beams emitted from the sample object; and the defect detecting means shows the defects as the differential interference image of the sample object generated with a contrast corresponding to the analyzer angle of the polarization selecting means, based on an output difference in the light detecting means when two different analyzer angles for the polarization selecting means are respectively set.

In this case, desirably, in the observation apparatus of the present invention, the light source emits a linearly polarized light beam having a wavelength of light for which a phase shift of $\pi$ multiplied by an integer is caused by a transparent substance constituting a predetermined pattern on the substrate or a wavelength substantially equal to a wavelength of light used to expose the predetermined pattern.

Also, desirably, in the observation apparatus of the present invention, the defect detection system comprises a differential circuit which generates a difference signal as the difference of two output signals sequentially input from the light detecting means, corresponding the two different polarized light beams selected by the polarization selecting means when two different analyzer angles for the polarization selecting means are respectively set, a binaring circuit which compares the difference signal from the differential circuit with a predetermined threshold value thereby generating a binary signal, and a judging circuit which detects the defects formed on the substrate on the basis of the binary signal from the binaring circuit.

Also, desirably, in the observation apparatus of the present invention, the polarization selecting means comprises an analyzer rotatable about an optical axis of the condenser optical system.

More desirably, the observation apparatus of the present invention further comprises an azimuth rotator which is disposed between the light source and the substrate, and having a variable polarization rotational angle. Note that in the observation apparatus of the present invention, the azimuth rotator may be constituted by a ½-wavelength plate disposed so as to be rotatable around the optical axis of the condenser optical system. Note that the observation apparatus of the present invention further may comprise an actuator which rotates the azimuth rotator around the optical axis of the condenser optical system; the actuator changes an azimuth of the azimuth rotator by 45° when the polarization selecting means changes selecting either of the two different polarized light components.

More desirably, the observation apparatus of the present invention further comprises a polarizer which is disposed between the light source and is rotatable about the optical axis of the condenser optical system. Note that the observation apparatus of the present invention further may comprise an actuator which rotates the polarizer around the optical axis of the condenser optical system; the actuator changes an azimuth of the polarizer by 90° when the polarization selecting means changes selecting either of the two different polarized light components.

Further, desirably, in the observation apparatus of the present invention, the two analyzer angles of the polarization selecting means are set to $n\pi/4$ and $(n/4+m/2)\pi$, respectively, wherein n and m are odd numbers.

Next, in order to attain the above-mentioned objects, the observation apparatus in accordance with another aspect of the present invention comprises (i) a light source for generating light; (ii) a separating optical system which splits the light emitted from the light source into two different polarized light beams; (iii) a condenser optical system which converges the two polarized light beams emitted from the separating optical system so as to respectively form light spots on two different positions on a sample object; (iv) a polarization selecting means which includes an azimuth rotator having a variable polarization rotational angle, variably sets an analyzer angle by the azimuth rotator and selects a specific polarized light component from composite light made of the two polarized light beams reflected by or transmitted through the sample object; (v) light detecting means which detects the polarized light component selected by the polarization selecting means; and (vi) phase difference adjustment means which adjusts a phase difference between the two polarized light beams reflected by or transmitted through the sample object and guides composite light composed of the two polarized light beams as circularly polarized light to the polarization selecting means, when the sample object does not modulate both phase and amplitude of the light incident thereon.

Here, preferably, the observation apparatus of the present invention further comprises a scanning device for scanning the sample object with the two light spots thereon which are split by the separating optical system, while the light source generates spatially coherent light and guides thus generated light to the separating optical system.

In this case, desirably, in the observation apparatus of the present invention, the light source generates linearly polarized light having a predetermined direction of polarization; when the sample object is a light reflecting member having a mirror surface, the phase difference adjustment means imparts a phase difference of $\pi$ multiplied by an integer to the two polarized light beams split by the separating optical system and then reflected by the sample object, as the two polarized light beams travel through the separating optical system to-and-fro; and the phase difference adjustment means includes a ¼-wavelength plate which converts the linearly polarized light emitted from the separating optical system into the circularly polarized light.

Also, desirably, in the observation apparatus of the present invention, the light source generates linearly polarized light having a predetermined direction of polarization; when the sample object is a light reflecting member having a mirror surface, the phase difference adjustment means imparts a phase difference of $\pi/2$ multiplied by an odd number to the two polarized light beams split by the separating optical system and then reflected by the sample object, as the two polarized light travel through the separating optical system to-and-fro.

Also, desirably, the observation apparatus of the present invention further comprises a synthesizing optical system which combines the two polarized light beams transmitted through the sample object and guides the composite light to the polarization selecting means; the light source generates linearly polarized light having a predetermined direction of polarization; when the sample object is optically flat, the phase difference adjustment means imparts a phase difference of $\pi$ multiplied by an integer to the two polarized light split by the separating optical system and then transmitted through the sample object; and wherein the phase difference adjustment means includes a ¼-wavelength plate which converts the linearly polarized light emitted from the synthesizing optical system into the circularly polarized light.

Further, desirably, the observation apparatus of the present invention further comprises a synthesizing optical system which combines the two polarized light beams transmitted through the sample object and guides the composite light to the polarization selecting means; the light source generates linearly polarized light having a predetermined direction of polarization; and when the sample object is optically flat, the phase difference adjustment means imparts a phase difference of $\pi/2$ multiplied by an odd number to the two polarized light split by the separating optical system and then transmitted through the sample object.

Also here, preferably, the observation apparatus of the present invention further comprises an illumination optical system which is disposed between the light source and the separating optical system and illuminates the sample object with the light thereon emitted from the light source by way of the separating optical system; the light detecting means is constituted by a two-dimensional image sensor disposed on at least one of respective focal planes of the condenser optical system.

In this case, desirably, in the observation apparatus of the present invention, the illumination optical system includes a wavelength selecting means for selecting a specific wavelength component from the light emitted from the light source. Also, desirably, in the observation apparatus of the present invention, the illumination optical system includes a polarized light selecting means for selecting a specific linear polarized light component from the light emitted from the light source.

More desirably, in the observation apparatus of the present invention, when the sample object is a light reflecting member having a mirror surface, the phase difference adjustment means imparts a phase difference of $\pi$ multiplied by an integer to the two polarized light beams split by the separating optical system and then reflected by the sample object, as the two polarized light beams travel through the separating optical system to-and-fro; the phase difference adjustment means includes a ¼-wavelength plate which converts the linearly polarized light emitted from the separating optical system into the circularly polarized light.

Also, more desirably, in the observation apparatus of the present invention, when the sample object is a light reflecting member having a mirror surface, the phase difference adjustment means imparts a phase difference of $\pi/2$ multiplied by an odd number to the two polarized light beams split by the separating optical system and then reflected by the sample object, as the two polarized light beams travel through the separating optical system to-and-fro.

Also, more desirably, the observation apparatus of the present invention further comprises a synthesizing optical system which combines the two polarized light beams transmitted through the sample object and guides the composite light to the polarization selecting means; when the sample object is optically flat, the phase difference adjustment means imparts a phase difference of $\pi$ multiplied by an integer to the two polarized light beams which has been split by the separating optical system and then transmitted through the sample object; and the polarization selecting means includes a ¼-wavelength plate which converts the linearly polarized light emitted from the synthesizing optical system into the circularly polarized light.

Further, more desirably, the observation apparatus of the present invention further comprises a synthesizing optical system which combines the two polarized light beams transmitted through the sample object and guides the composite light to the polarization selecting means; when the sample object is optically flat, the phase difference adjustment means imparts a phase difference of π/2 multiplied by an odd number to the two polarized light beams split by the separating optical system and then transmitted through the sample object.

Also here, preferably, in the observation apparatus of the present invention, the condenser optical system is arranged so as to serve as an objective optical system which collects the two polarized light beams reflected by the sample object, and the separating optical system is arranged so as to serve as a synthesizing optical system which combines the two polarized light beams again exited from the condenser optical system and guides the composite light to the polarization selecting means.

In this case, desirably, in the observation apparatus of the present invention, the separating optical system includes a birefringence prism. Also, desirably, in the observation apparatus of the present invention, the separating optical system includes a prism having two reflecting surfaces non-parallel to each other, and a polarizing beam splitter surface disposed between the two reflecting surfaces and parallel to either of the two reflecting surfaces.

Also, preferably, in the observation apparatus of the present invention, the separating optical system includes two mirrors having respective reflecting surfaces non-parallel to each other, and two prisms disposed between the two mirrors and having respective polarizing beam splitter surfaces parallel to either of the reflecting surfaces of two reflecting mirrors. Also, preferably, in the observation apparatus of the present invention, the phase difference adjustment means comprises a driving member capable of moving the separating optical system.

Also, preferably, the observation apparatus of the present invention further comprises an objective optical system which converges the two polarized light beams transmitted through the sample object, and a synthesizing optical system which combines the two polarized light beams emitted from the objective optical system and guides the composite light to the polarization selecting means.

In this case, desirably, in the observation apparatus of the present invention, at least one of the separating optical system and the synthesizing optical system includes a birefringence prism. Also, desirably, in the observation apparatus of the present invention, at least one of the separating optical system and the synthesizing optical system includes a prism having two reflecting surfaces non-parallel to each other, and a polarizing beam splitter surface disposed between the two reflecting surfaces and parallel to either of the two reflecting surfaces.

Also, desirably, in the observation apparatus of the present invention, at least one of the separating optical system and the synthesizing optical system includes two mirrors having respective reflecting surfaces non-parallel to each other, and two prisms disposed between the two mirrors and having respective polarizing beam splitter surfaces parallel to either of the reflecting surfaces of two reflecting mirrors. Further, desirably, in the observation apparatus of the present invention, the phase difference adjustment means comprises a driving member capable of moving at least one of the separating optical system and the synthesizing optical system.

Also here, preferably, in the observation apparatus of the present invention, the polarization selecting means variably sets the analyzer angle with respect to the composite light composed of the two polarized light beams reflected by or transmitted through the sample object and includes a polarizing beam splitter which splits the composite light into two different directions; and the light detecting means includes a first photodetector for detecting light transmitted through the polarizing beam splitter and a second photodetector for detecting light reflected by the polarizing beam splitter.

In this case, desirably, in the observation apparatus of the present invention, the polarizing beam splitter is fixed around an optical axis of the condenser optical system and wherein the azimuth rotator is disposed on an inlet side of the polarizing beam splitter. More desirably, in the observation apparatus of the present invention, the azimuth rotator is constituted by a ½-wavelength plate disposed so as to be rotatable around the optical axis of the condenser optical system.

Also, desirably, in the observation apparatus of the present invention, each of the polarizing beam splitter and the first and second photodetectors is disposed so as to be rotatable around the optical axis of the condenser optical system. Also, desirably, in the observation apparatus of the present invention, an analyzer angle $\phi_{min}$ of the polarization selecting means when the output difference between the first and second photodetectors for the level difference of the sample object is minimum, coincides with $\phi_{max}+n\pi/4$, wherein $\phi_{max}$ is an analyzer angle of the polarization selecting means when the output difference between the first and second photodetectors for the level difference of the sample object is maximum, and n is an odd number.

Also, desirably, the observation apparatus of the present invention further comprises a measuring means for quantitatively measuring, based on an output of the light detecting means, a level difference on the sample object; the measuring means measures the level difference of the sample object based on the analyzer angle which is set so as to maximize or minimize the output difference between the first and second photodetectors for the level difference of the sample object.

More desirably, in the observation apparatus of the present invention, the measuring means measures a level difference of the object sample based on a phase difference $\Psi$ between the two polarized light beams calculated by the following relationship:

$$\tan 2\phi = -2a \cdot b \cdot \sin \Psi/(a^2-b^2)$$

wherein $\phi$ is the analyzer angle of the polarization selecting means when the output difference between the first and second photodetectors for the level difference of the sample object is maximum, $\Psi$ is the phase difference between the two polarized light beams caused by the level difference of the sample object, a is an amplitude reflectance of one of two regions holding the level difference of the sample object therebetween incorporated in an output sum of the light detecting means for the region, and b is an amplitude reflectance of the other of two regions holding the level difference of the sample object therebetween incorporated in an output sum of the light detecting means for the other region.

Also, desirably, the observation apparatus of the present invention further comprises an image forming means which forms a differential interference image of the sample object based on an output of the light detecting means; the image forming means generates, based on an output difference between the first and second photodetectors for the level difference of the sample object, a contrast corresponding to the analyzer angle of the polarization selecting means for the differential interference image of the sample object.

Further desirably, the observation apparatus of the present invention further comprises a defect detection system which detects the defect formed on a substrate being the sample object on the basis of an output from the light detecting means; wherein the defect detecting means shows the defects as the differential interference image of the sample object generated with a contrast corresponding to the analyzer angle of the polarization selecting means, based on an output difference between the first and second photodetectors.

More desirably, in the observation apparatus of the present invention, the light source emits a linearly polarized light beam having a wavelength of light for which a phase shift of $\pi$ multiplied by an integer is caused by a transparent substance constituting a predetermined pattern on the substrate or a wavelength substantially equal to a wavelength of light used to expose the predetermined pattern. Also, more desirably, in the observation apparatus of the present invention, the defect detection system comprises a differential circuit which generates a difference signal as the difference of two output signals respectively input from the first and second photodetectors, corresponding the two different polarized light beams selected by the polarization selecting means, a binaring circuit which compares the difference signal from the differential circuit with a predetermined threshold value thereby generating a binary signal, and a judging circuit which detects the defects formed on the substrate on the basis of the binary signal from the binaring circuit.

In general, a differential interference microscope can provide a geometric level difference existing on the sample object with a contrast which nearly equals a differential image. However, typical level differences existing on the sample object are not simply constituted by surface irregularities (geometric level differences) alone. In a chromium pattern deposited on a glass substrate, for example, not only a geometric level difference corresponding to the chromium film thickness exists but the light reflectivity largely changes between both sides of the level difference.

Thus, a typical level difference has a characteristic of modulating both phase and amplitude of the light incident thereon. Accordingly, different level differences consequently yield different degrees of phase and amplitude modulation. It is not always possible to attain a differential interference image with an optimal contrast by way of a fixed optical system. However, as a result of various studies conducted by the inventors, a simple novel configuration is added to the conventional configurations of a laser scanning type differential interference microscope and an imaging type differential interference microscope, thereby yielding an observation apparatus which is configured as a differential interference microscope which can attain a differential interference image with an optimal contrast for any level difference, a level-difference measuring apparatus which can quantitatively measure any level difference with high accuracy, a defect inspection apparatus which can detect defects and foreign substances on various typed reticles with high sensitivity or the like.

The defect inspection apparatus of the present invention is obtained by applying an imaging type differential interference microscope or the differential interference microscope of a laser scanning optical system thereto. The analyzer (polarization selection means) arranged in such a differential interference microscope is used as, e.g., a polarizing beam splitter to detect the transmitted light and reflected light from the beam splitter simultaneously or time-divisionally, thereby obtaining a differential interference image on the basis of the differential output between the transmitted light and the reflected light.

The illumination light beam has a wavelength substantially equal to the exposure wavelength of an exposure apparatus, or a wavelength for which a phase shift of $\pi$ multiplied by an integer is caused by a phase shifter upon transmission through or reflection by the substrate such that a change in phase corresponding to $\pi$ multiplied by an integer is caused in the light beam transmitted through a nondefective transparent substance (phase shifter). When the analyzer angle of the polarizing beam splitter is optimally adjusted, the sensitivity for detecting a defect (foreign substance) can be maximized, and a differential output in observing the nondefective transparent substance can be made zero. Therefore, a defect inspection apparatus capable of inspecting both the presence/absence of a defect in phase shifter and the presence/absence of a transparent foreign substance can be obtained.

In the following, the operation of the observation apparatus of the present invention will be theoretically explained. Here, since the level difference of a circuit pattern on a reticle basically has one-dimensional characteristics, all the elements including optical systems are treated one-dimensionally. While actual optical systems have two-dimensional characteristics, it is needless to mention that two-dimensional models can be easily attained when an orthogonal coordinate system is simply introduced into each of the following expressions.

Also, in the following explanation, laser light, which is spatially coherent light, is used as typical illumination light irradiating a sample object. Of course, other kinds of illumination light can be adopted. Note that, with an imaging type differential interference microscope, the same differential interference image can be obtained by appropriately setting the $\sigma$ value of the illumination system, though the focal depth is different.

It is assumed that a one-dimensional coordinate x is set on a sample object and that a level difference of a circuit pattern on a reticle exists at its origin x=0. Also, it is assumed that the object is flat except for x=0 and that a complex amplitude distribution O(x) is given by the following expression (1):

$$O(x) = \begin{cases} a & x \leq 0 \\ b \exp[i\Psi] & x > 0 \end{cases} \tag{1}$$

wherein a and b are square roots of reflectivities or transmittances (i.e., the absolute value of the complex amplitude reflectance or the complex amplitude transmittance) of the object at regions of $x \leq 0$ and $x > 0$, respectively, and $\Psi$ is the amount of change in phase of the incident light caused by the level difference.

Next, intensity I of the differential interference image at this level difference position is determined. At the level difference position, i.e., x=0, two laser spots (point images of illumination light) formed on the sample surface by the observation apparatus are respectively disposed at positions which are symmetrical to each other on both sides of the level difference held therebetween. Namely, assuming that the distance between the two laser spots (point images of the illumination light) is $2\delta$, the first spot center is at $x=\delta$ whereas the second spot center is at $x=-\delta$.

Initially, the first spot is considered. Assuming that the amplitude distribution of the laser spot on the object is u(x), complex amplitude $P_1$ of the light diffracted into direction cosine $\alpha$ direction by the diffraction of the first spot is given by the following expression (2):

$$P_1 = a \int_{-\infty}^{\delta} u(x)\exp[-ik\alpha x]dx + b\exp[i\Psi] \int_{\delta}^{\infty} u(x)\exp[-ik\alpha x]dx \quad (2)$$

Similarly, with respect to the second spot, complex amplitude $P_2$ of the light diffracted into direction cosine α direction by the diffraction thereof is given by the following expression (3):

$$P_2 = a \int_{-\infty}^{-\delta} u(x)\exp[-ik\alpha x]dx + b\exp[i\Psi] \int_{-\delta}^{\infty} u(x)\exp[-ik\alpha x]dx \quad (3)$$

Assuming that the phase difference generated between the light corresponding to the first spot and the light corresponding to the second spot by an optical system extending from a laser light emission point (light source) to a point just in front of an analyzer such as a polarizing beam splitter (i.e., the phase difference between the light components respectively corresponding to these two spots just in front of the analyzer when a mirror surface or a reticle without any circuit pattern and defect is used as the sample object) is θ and the azimuth (analyzer angle) of the analyzer (polarizing beam splitter) is φ; transmitted light intensity $i_T$ and reflected light intensity $i_R$ at the analyzer (polarizing beam splitter) are respectively given by the following expressions (4) and (5):

$$i_T = |\cos\phi P_1 + \exp[i\theta]\sin\phi P_2|^2 \quad (4)$$

$$i_R = |-\sin\phi P_1 + \exp[i\theta]\cos\phi P_2|^2 \quad (5)$$

Actually, all the diffracted light components with direction cosine values smaller than numerical aperture NA of a lens are received by the lens. Accordingly, whole transmitted light intensity $I_T$ and whole reflected light intensity $I_R$ are respectively given by the following expressions (6) and (7):

Accordingly, difference signal S between the whole transmitted light intensity $I_T$ and whole reflected light $$I_T = \int_{-NA}^{NA} i_T d\alpha \quad (6)$$

$$I_R = \int_{-NA}^{NA} i_R d\alpha \quad (7)$$

intensity $I_R$ is given by the following expression (8):

$$S = I_T - I_R \quad (8)$$

When expressions (1) to (7) are input into expression (8), the relationship represented by the following expression (9) is obtained:

$$S = 2C\{\cos 2\phi(a^2-b^2)-\sin 2\phi 2ab \cos(\theta+\Psi)\} \quad (9)$$

In the present invention, when the phase difference is set to θ=π/2, the relationship represented by the following expression (10) is obtained:

$$S = 2C\{\cos 2\phi(a^2-b^2)-\sin 2\phi 2ab \sin \Psi\} \quad (10)$$

In the above two expressions (9) and (10), C is an apparatus constant independent of the object and given by the following expression (11):

The right side of expression (10) can be represented as a form of an inner product of vectors given by the following expression (12):

Accordingly, the difference signal S at the level $$C = \int_0^{NA} \left[ \left\{ \int_{-28}^{\delta} u(x)\cos(k\alpha x)dx \right\}^2 - \left\{ \int_{-\infty}^{\delta} u(x)\cos(k\alpha x)dx \right\}^2 \right] d\alpha \quad (11)$$

$$S = 2C(\cos 2\phi, \sin 2\phi) \cdot (a^2-b^2, -2ab\sin\Psi) \quad (12)$$

difference position is maximized when the two vectors of the above expression (12) is parallel to each other, i.e., when the analyzer angle φ satisfies the following expression (13):

$$\tan 2\phi = \frac{-2ab\sin\Psi}{a^2-b^2} \quad (13)$$

Also, in view of expression (12), it can be seen that the difference signal S at the level difference position is minimized (nullified) when the two vectors of the above expression (12) are orthogonal to each other, i.e., when the analyzer angle satisfying the above expression (12) is shifted by π/4. Here, the analyzer angle is obtained when ±π/4 is added to the φ satisfying the above expression (13).

In the following, the reason why the phase difference is set to θ=π/2 in the present invention will be explained.

First, when θ=π/2 is set, cos(θ+Ψ), which is the portion including the phase difference θ in the right side of expression (9), is incorporated as sinΨ in the difference signal S as represented by expression (10). Thus, the sensitivity of the difference signal S with respect to the minute phase difference Ψ corresponding to the minute level difference becomes most favorable when the phase difference θ=π/2 is set. In other words, when the phase difference θ=π/2 is set, the difference signal S (contrast) with respect to the minute level difference can be made large.

Next, when the phase difference θ=π/2 is set, the difference signals S (contrasts) for both side edges of the level difference can be simultaneously maximized (or minimized). Assuming that the amplitude reflectance at the level difference portion is b and that the amplitude reflectance at flat portions on both sides thereof is a, the phase difference due to the level difference changes from 0 to Ψ as the amplitude reflectance at one edge changes from a to b. At the other edge, the phase difference changes from Ψ to 0 as the amplitude reflectance changes from b to a.

Namely, between the edges, a and b are interchanged and the signs of the phase difference Ψ are opposite to each other at the right side of expression (13). Here, even when a and b are interchanged and the sign of the phase difference Ψ is reversed, the value of the right side of expression (13) does not change. It means that the analyzer angle for maximizing (or minimizing) the difference signal S (contrast) of one edge equals the analyzer angle for maximizing (or minimizing) the difference signal S (contrast) of the other edge. In other words, when the phase difference θ=π/2 is set, the difference signals S (contrasts) for both side edges of the level difference can be simultaneously maximized (or minimized) at the same analyzer angle.

If the phase difference θ=0 is set instead of θ=π/2, the difference signal S at the level difference position will be maximized when the two vectors of the above equation (12) are orthogonal each other, that is, the analyzer angle φ satisfies the following expression (14):

$$\tan 2\phi = \frac{-2ab\cos\Psi}{a^2 - b^2} \quad (14)$$

In the above expression (14), when a and b are interchanged and the sign of the phase difference $\Psi$ is reversed, the value of the right side changes. Namely, unless the phase difference $\theta=\pi/2$ is set as in the case of the present invention, even when the contrast for one edge is maximized (or minimized), the contrast for the other edge fails to be maximized (or minimized) with respect to the analyzer angle at that time.

Thus, in the present invention, the phase difference imparted to the light components corresponding to the two spots by the optical system by the time these light components reach just in front of the analyzer is set to $\pi/2$, namely, the light reaches the analyzer as circularly polarized light, while the analyzer angle $\phi$ of the polarizing beam splitter is made variable. In this manner, with respect to any level difference, the difference signal at the level difference position can be changed from maximum to minimum. Namely, the contrast of the differential interference image formed with respect to any level difference can be adjusted at any time.

In the present invention, as mentioned above, the phase difference imparted to the light components corresponding to the two spots by the optical system by the time these light components reach just in front of the analyzer is set to $\pi/2$, namely, the light reaches the analyzer as circularly polarized light, while the analyzer angle $\phi$ of the polarizing beam splitter is made variable. Accordingly, the value of the right side in expression (13) can be determined from the analyzer angle at which the difference signal S at the level difference position is maximized. Also, the inverse number of the right side value in expression (13) can be determined from the analyzer angle at which the difference signal S at the level difference position is minimized.

Namely, when the analyzer angle at which the difference signal S is qualitatively maximized or minimized is measured, namely, without quantitatively measuring the value of the difference signal S (without directly measuring the light quantity), an amount including the phase difference $\Psi$ due to the level difference can be determined with high accuracy. Here, the right side of expression (13) includes the amplitude reflectances a and b in addition to the phase difference $\Psi$. In order to determine the amplitude reflectances a and b, sum signal $W=I_T+I_R$ at a position sufficiently distanced from the level difference is determined as explained in the following.

For example, at a position of x<0 which is sufficiently distanced from the level difference position x=0, the relationship represented by the following expression (15) is established with a good approximation:

$$P_1 = P_2 = a \int_{-\infty}^{\infty} u(x)\exp[b - ik\alpha x]dx \quad (15)$$

When expression (15) is input into expressions (4) to (7) and $\theta=\pi/2$ is set, sum signal $W_a$ with respect to the position of x<0 sufficiently distanced from the level difference position x=0 is given by the following expression (16):

$$W_a = 2a^2 \int_{-NA}^{NA} \left| \int_{-\infty}^{\infty} u(x)\exp[-ik\alpha x]dx \right|^2 d\alpha \quad (16)$$

Thus, when the square root of the sum signal $W_a$ given by expression (16) is calculated, the amplitude reflectance a can be determined. Here, in addition to the amplitude reflectance a, expression (16) includes an apparatus constant which is dependent on the apparatus. This apparatus constant is a calculable amount. In practice, the apparatus constant can be determined when a calibration is performed with a sample whose level difference and reflectivity are known.

Also, when the square root of the sum signal $W_b$ with respect to a position of x>0 sufficiently distanced from the level difference position x=0 is calculated, the other amplitude reflectance b can be similarly determined.

Thus, based on the value of the right side in expression (13) determined from the analyzer angle at which the difference signal S is maximized or minimized and the two amplitude reflectance values a and b respectively determined from the sum signals $W_a$ and $W_b$, the phase difference $\Psi$ can be calculated. Then, based on thus calculated phase difference $\Psi$, level difference $\Delta h$ can be determined from the following expression (17):

$$\Delta h = \frac{\Psi \lambda}{4\pi n} \quad (17)$$

wherein $\lambda$ is the wavelength of light and n is the refractive index of a medium (1 for the air).

Here, when the complex index of refraction differs between both sides of the level difference, a difference in phase hit amount of light is generated in the reflection with respect to two laser spots (point images of illumination light). Accordingly, it is necessary to measure the difference in phase hit amount of light beforehand and then correct, with thus measured difference in phase hit amount of light, the value of the phase difference $\Psi$ determined according to expression (13). However, when the difference in phase hit amount of light is of such a magnitude that it can fall within an error range, no correction is necessary.

Also, in the present invention, the phase difference imparted to the light components corresponding to the two spots by the optical system by the time these light components reach just in front of the analyzer is set to $\pi/2$, namely, the light reaches the analyzer as circularly polarized light, while the analyzer angle $\phi$ of the polarizing beam splitter is set to $\pi/4$. Thus, the difference signal S at the level difference position is given by the following expression (18):

$$S = -4Cab \sin \Psi \quad (18)$$

Thus, when the value of the difference signal S is quantitatively measured (i.e., light quantity is measured), an amount including the phase difference $\Psi$ can be determined. Here, the right side of expression (18) includes the respective amplitude reflectances a and b for both sides of the level difference in addition to the phase difference $\Psi$. In order to determine the amplitude reflectances a and b, sum signal $W=I_T+I_R$ at a position sufficiently distanced from the level difference is determined as explained above.

Accordingly, the relationship represented by expression (16) concerning the sum signal $W_a$ and an expression corresponding thereto concerning the sum signal $W_b$ can be used to eliminate the amplitude reflectances a and b from the expression (18). As a result, the relationship represented by the following expression (19) is obtained:

$$\sin \Psi = D \frac{S}{\sqrt{W_a} \sqrt{W_b}} \quad (19)$$

Here, in addition to the difference signal S and the sum signals $W_a$ and $W_b$, the right side of expression (19) includes an apparatus constant D which is dependent on the apparatus. This apparatus constant D is a calculable amount. In practice, the apparatus constant D can be determined when a calibration is performed with a sample whose level difference and reflectivity are known.

Thus, the phase difference $\Psi$ can be determined on the basis of expression (19) which is a relational expression dependent on the change in amplitude reflectance between the difference signal S and the phase difference $\Psi$. Then, based on thus determined phase difference $\Psi$, the level difference $\Delta h$ can be determined according to the above-mentioned expression (17).

Here, when the complex index of refraction differs between both sides of the level difference, a difference in phase hit amount of light is generated in the reflection with respect to two laser spots. Accordingly, it is necessary to measure the difference in phase hit amount of light beforehand and then correct, with thus measured difference in phase hit amount of light, the value of the phase difference $\Psi$ determined according to expression (19). However, when the difference in phase hit amount of light is of such a magnitude that it can fall within an error range, no correction is necessary.

The present invention has as its main object to detect a transparent foreign substance as a phase object, and a defect in phase difference of a phase shifter portion. In this case, the differential output S of expression (10) becomes most favorable to exhibit the maximum gain (sensitivity) as represented by expression (18) when the analyzer angle is set as $\phi=\pi/4+n\pi/2$ (n=0, 1, 2, 3, . . . ). To the contrary, when $\phi=n\pi/2$ (n=0, 1, 2, 3, . . . ), the capability of detecting a foreign substance as a phase object becomes minimum.

When the level difference portion of a nondefective circuit pattern is to be observed with transmission illumination, the differential output S is preferably minimum (zero). Three cases are considered for the complex amplitude transmittance distribution representing the level difference of a nondefective circuit pattern. The first case is for the level difference at the boundary between the glass portion and the phase shifter portion, which is represented by expression (20). The second case is for the level difference at the boundary between the glass portion and the chromium light-shielding film, which is represented by expression (21). The third case is for the level difference at the boundary between the chromium light-shielding film and the phase shifter portion, which is represented by expression (22):

$$O_1(x)=a_1[x<0]b_1 \exp(i\Psi_1)[x>0] \quad (20)$$

$$O_2(x)=a_1[x<0]b_2 \exp(i\Psi_2)=0[x>0] \quad (21)$$

$$O_3(x)=b_2 \exp(i\Psi_2)=0[x<0]b_1 \exp(i\Psi_1)[x>0] \quad (22)$$

In the cases that the complex amplitude distribution in the level difference is represented by two expressions (21) and (22), the above expression (18) automatically yields zero. In the case that the complex amplitude distribution in the level difference is represented by the expressions (20), expression (18) yields zero when $\Psi_1=n\pi$ (n=0, 1, 2, 3, . . . ). The amount of phase shift at the phase shifter portion with respect to light with an exposure wavelength is $\pi$ multiplied by an odd number. Therefore, defect inspection is preferably performed using a wavelength substantially equal to the exposure wavelength of an exposure apparatus or a wavelength for which the phase shifter causes a phase shift of $\pi$ multiplied by an integer upon transmission through the transparent substrate.

Above mentioned limited condition for the wave length of transmission illumination is necessary only for the inspection of the phase shift mask that has the boundary represented by equation (20). Here we would like to review the variations of photo mask (either called photo mask or reticle) types.

At this time, the various type of the phase shift masks have been developed for the laboratory use, but for the commercial use, and there are still few variations. The most common phase shift masks in the market today are half tone mask that is sometimes called attenuated mask and the Levenson type photo mask. The former type does have the boundary represented by equation (20), while the latter type does not have the boundary represented by equation (20).

Beside these phase shift masks, the conventional masks (without phase shifters) off course does not have the boundary represented by equation (20). So, if the masks to be inspected are limited to either Levenson type phase shift mask or conventional type photo mask, it is not necessary to choose the wave length of the transmission illumination.

We will later describe the other way to minimize the signal S on the boundary represented by equation (20) using the adjustment of the angular direction of the analyzer with respect to equation (10). This alternate way off course applies only for the reticle with the boundary represented by equation (20).

In the embodiments and the like to be described later, light having a wavelength substantially equal to or matching the exposure wavelength is used as illumination light, and $\Psi_1=\pi$. At this time, when the analyzer angle $\phi$ is set to be $\pi/4$, the detection capability can be maximized, and the differential output can be made zero in observing a nondefective circuit pattern.

If the circuit pattern of a reticle to be inspected is limited to a chromium light-shielding film, the complex amplitude transmittance distribution representing the level difference of a nondefective circuit pattern is represented by only expression (21). At this time, the azimuth of the analyzer (analyzer angle) $\phi$ is set to be $\pi/4$, and the illumination light may have an arbitrary wavelength.

If the reticle to be inspected is limited to a halftone reticle, the complex amplitude transmittance distribution representing the level difference of a nondefective circuit pattern is represented by only expression (20). At this time, as the wavelength of illumination light, a wavelength substantially equal to the exposure wavelength of the exposure apparatus, or a wavelength for which the phase shifter causes a phase shift of $\pi$ multiplied by an integer upon transmission through the transparent substrate may be selected, and the azimuth of the analyzer (analyzer angle) $\phi_1$ may be set to satisfy expression (22):

$$S=2C\{\cos 2\phi_1(a_1^2-b_1^2)-\sin 2\phi_1 2a_1b_1 \sin \Psi_1\}=0 \quad (17)$$

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE PREFERRED EMBODIMENTS

Figure 1:
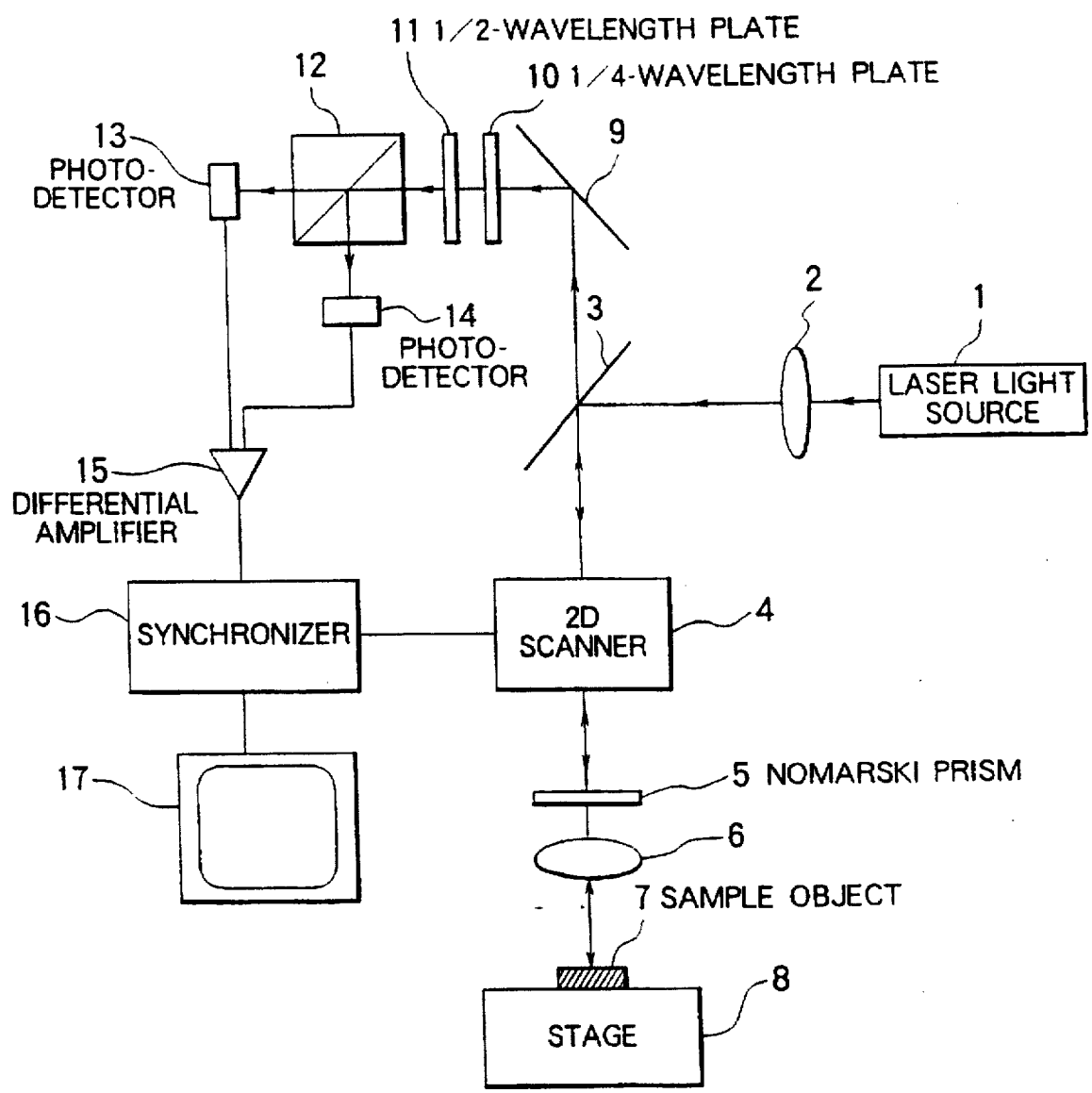
FIG. 1 is a block diagram schematically showing a configuration of a differential interference microscope as a first embodiment in accordance with the observation apparatus of the present invention.

In the following, configurations and operations of various embodiments concerning the observation apparatus in accordance with the present invention will be explained in detail with reference to FIGS. 1 to 25. Here, in the explanation of the drawings, elements identical to each other are referred to with marks identical to each other without repeating their overlapping explanations. Also, the size ratios in the drawings do not always correspond to those explained.

First Embodiment

As shown in FIG. 1, the differential interference microscope of this embodiment comprises a laser light source 1 which supplies, as spatially coherent light, a linearly polarized laser beam having a polarization direction which is in parallel to the paper surface of FIG. 1, for example. The laser beam from the laser light source 1 is turned into parallel light by way of a collimator lens 2 and then made incident on a half mirror 3.

The laser beam reflected by the half mirror 3 in a downward direction in the drawing is spatially deflected by a two-dimensional scanner 4 and then made incident on a Nomarski prism 5. The Nomarski prism 5 is a birefringence prism which has an optic axis intersecting the polarization direction of the incident laser beam at 45° and splits the incident laser beam into two light components according to their polarization characteristics.

The two light components split by the Nomarski prism 5 are converged by way of an objective lens 6 so as to form two laser spots on a sample object 7 such as a substrate mounted on a stage 8.

Thus, due to an operation of the Nomarski prism 5, two laser spots slightly distanced from each other are formed on the sample object 7. The object 7 is two-dimensionally scanned with these two laser spots according to the two-dimensional deflecting operation of the two-dimensional scanner 4.

Two reflected laser beams from the object 7 with respect to the two laser spots are transmitted through the objective lens 6 again and then combined together by way of the Nomarski prism 5.

Here, the inserting position of the Nomarski prism 5 with respect to the optic axis of the objective lens 6 is defined such that the Nomarski prism 5 imparts a phase difference of $\pi$ multiplied by an integer to the light components corresponding to the two laser spots as they travel therethrough to-and-fro. Accordingly, when the object 7 is of a flat surface having no level difference, namely, a mirror surface upon which the two laser spots do not relatively change their wavelengths and phases, the phase difference between the two reflected laser beams by way of the Nomarski prism 5 becomes $\pi$ multiplied by an integer. In other words, the two reflected laser beams from the object 7 with respect to the two laser spots are combined together, by way of the Nomarski prism 5, into a linearly polarized laser beam having a polarization direction in parallel to the paper surface of FIG. 1.

The composite laser beam formed by way of the Nomarski prism 5 is turned into a parallel luminous flux again by way of the two-dimensional scanner 4 and then made incident on the half mirror 3. Here, the parallel luminous flux emitted from the two-dimensional scanner 4 attains a still state within the space since it has been subjected to the deflecting operation of the two-dimensional scanner 4 twice.

The composite laser beam transmitted through the half mirror 3 is made incident on a ¼-wavelength plate 10 by way of a mirror 9. The ¼-wavelength plate 10 is positioned so as to have an azimuth of $\pi/4$ with respect to the linear polarization direction of the composite linearly polarized laser beam which is incident on the ¼-wavelength plate 10 when the object 7 is of a mirror surface. Accordingly, when the object 7 is of a mirror surface, the laser beam emitted from the ¼-wavelength plate 10 becomes circularly polarized light and then is made incident on a ½-wavelength plate 11 which is rotatable around an optical axis conforming to the optical axis of the objective lens 6.

The laser beam emitted from the ½-wavelength plate 11 is separated into transmitted light and reflected light by a polarizing beam splitter 12. Thus, the ½-wavelength plate 11 is an analyzer whose polarization rotational angle is variable. The rotatable ½-wavelength plate 11 and the fixed polarizing beam splitter 12 constitute a polarizing beam splitter having a variable analyzer angle.

The light transmitted through the polarizing beam splitter 12 is detected and photoelectrically converted by a photodetector 13. On the other hand, the light reflected by the polarizing beam splitter 12 is detected and photoelectrically converted by a photodetector 14.

The respective electric signals photoelectrically converted by the two photodetectors 13 and 14 are supplied to a differential amplifier 15. The differential amplifier 15 determines a difference signal S based on the respective signals from the two photodetectors 13 and 14 and supplies thus determined difference signal S to a synchronizer 16. The synchronizer 16 synchronizes information about the scanning position of the laser spots corresponding to the operation of the two-dimensional scanner 4 and the difference signal S from the differential amplifier 15 with each other and supplies them to an image display device 17.

The image display device 17 forms a differential interference image based on the information about the scanning position of the laser spots and the difference signal S and displays thus formed differential interference image. Here, the contrast of the differential interference image displayed on the image display device 17 changes depending on the polarization rotational angle due to the ½-wavelength plate 11 and, accordingly, depending on the analyzer angle of the polarizing beam splitter 12. Namely, in the present embodiment, the contrast of the resulting differential interference image changes as the ½-wavelength plate 11 is appropriately rotated around its optical axis.

Here, the contrast of the differential interference image can be maximized when the polarization rotational angle of the ½-wavelength plate 11, i.e., analyzer angle, satisfies $\phi$ in the above-mentioned expression (13). Also, the contrast of the differential interference image can be minimized when an analyzer angle of $\phi$ in the above-mentioned expression (13) with $\pm \pi/4$ being added thereto is used. Namely, in the present embodiment, the contrast of the resulting differential interference image can be arbitrarily adjusted from maximum to minimum as the ½-wavelength plate 11 is appropriately rotated around its optical axis.

Figure 2A:
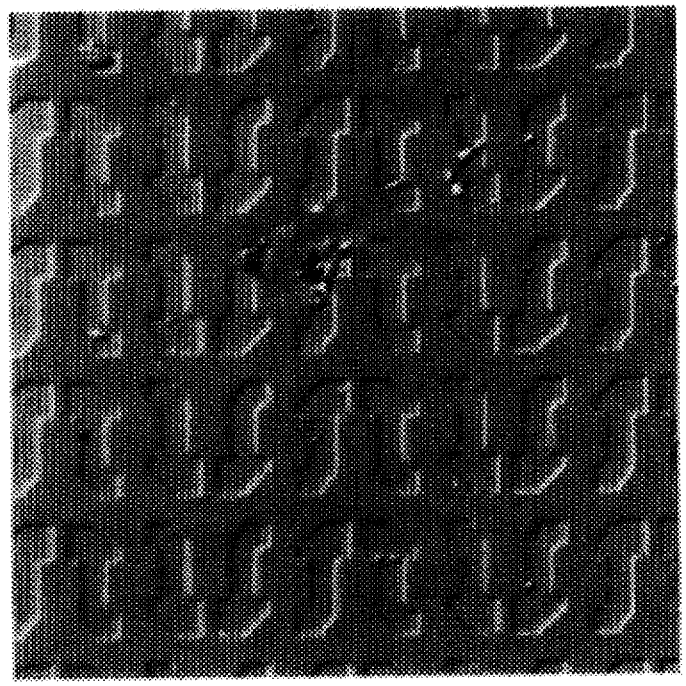
FIGS. 2A and 2B are photographs showing differential interference images obtained when contrast is set to the maximum and minimum values in the differential interference microscope of FIG. 1, respectively.
Figure 2B:
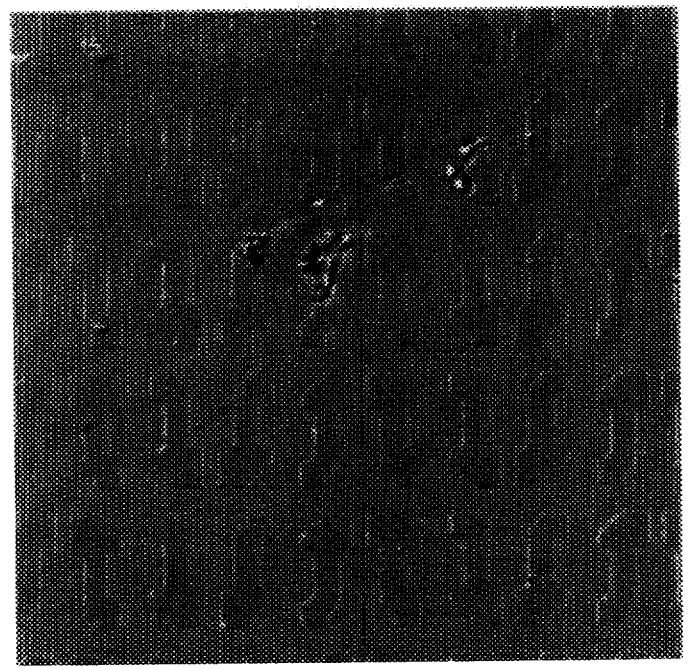

FIGS. 2A and 2B respectively show the results of differential interference images captured with two different kinds of contrast being set when a periodic circuit pattern formed on a semiconductor wafer is used as the sample object 7.

When the contrast for a defect-free region of the image pickup area in the periodic circuit pattern is set to the maximum as shown in FIG. 2A, the contrast for a defect region which is disposed nearly at the center of the image pickup area in the periodic circuit pattern is set high. In this case, the defect-free region can be observed with the defect-free state being highlighted.

On the other hand, when the contrast for the defect-free region is set to the minimum as shown in FIG. 2B, the contrast for the defect region is set high. Also, in this case, the defect-free region can be observed with the defect-free state being highlighted.

Second Embodiment

Figure 3:
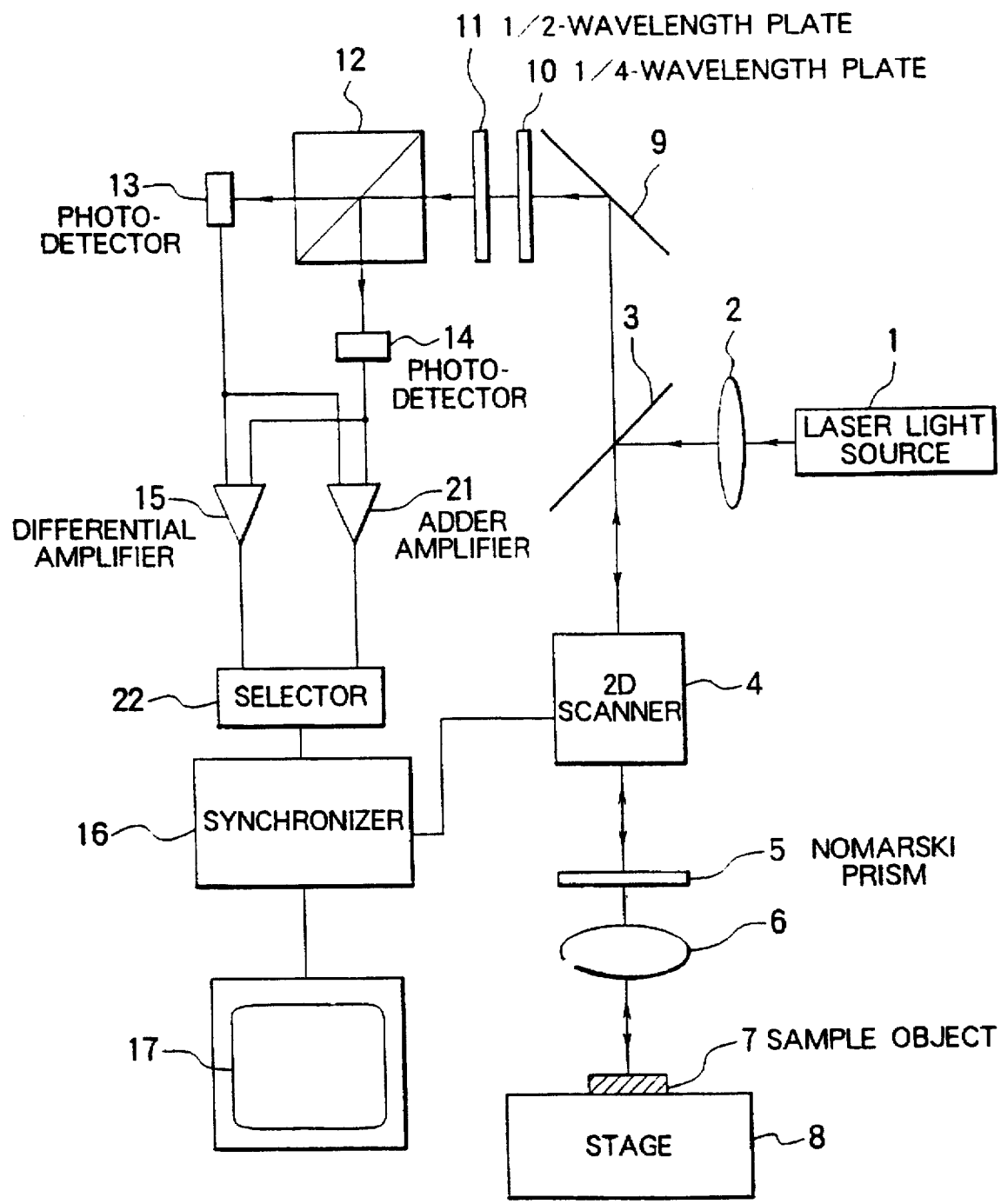
FIG. 3 is a block diagram schematically showing a configuration of a differential interference microscope as a second embodiment in accordance with the observation apparatus of the present invention.

As shown in FIG. 3, the differential interference microscope of this embodiment has a configuration similar to that of the first embodiment. The present embodiment basically differs from the first embodiment only in that an adder amplifier 21 and a selector 22 are additionally provided. Accordingly, in FIG. 3, elements having functions similar to those of the first embodiment are referred to with marks identical thereto. In the following, the configuration and operation of the present embodiment will be explained with their differences from those of the first embodiment being taken into account.

In the differential interference microscope of this embodiment, by way of the collimator lens 2, half mirror 3, two-dimensional scanner 4, Nomarski prism 5, and objective lens 6, the laser beam from the laser light source 1 forms two laser spots on the sample object 7 mounted on the stage 8.

The two reflected laser beams from the object 7 with respect to the two laser spots are transmitted through the objective lens 6 again and then combined together by way of the Nomarski prism 5.

The composite laser beam formed by way of the Nomarski prism 5 is made incident on the ¼-wavelength plate 10 by way of the two-dimensional scanner 4, half mirror 3, and mirror 9. As in the case of the first embodiment, the laser beam emitted from the ¼-wavelength plate 10 is made incident on the ½-wavelength plate 11 as circularly polarized light when the object 7 is of a mirror surface, while the ½-wavelength plate 11 is rotatable around its optical axis.

Then, the light transmitted through the polarizing beam splitter 12 is detected by the photodetector 13, whereas the light reflected by the polarizing beam splitter 12 is detected by the photodetector 14.

Each of the respective electric signals photoelectrically converted by the two photodetectors 13 and 14 is supplied to the differential amplifier 15 and the adder amplifier 21. The differential amplifier 15 determines the difference signal S based on the respective signals from the two photodetectors 13 and 14, whereas the adder amplifier 21 determines the sum signal W based on the respective signals from the two photodetectors 13 and 14. The difference signal S determined by the differential amplifier 15 and the sum signal W determined by the adder amplifier 21 are supplied to the selector 22. The selector 22 selects one of the difference signal S and sum signal W and supplies thus selected signal to the synchronizer 16.

The synchronizer 16 synchronizes information about the scanning position of the laser spots corresponding to the operation of the two-dimensional scanner 4 and the signal S or W from the selector 22 with each other and supplies them to the image display device 17.

The image display device 17 forms an image based on the information about the scanning position of the laser spots and the signal S or W and displays thus formed image. Here, a differential interference image is formed on the image display device 17 when the difference signal S is selected by the selector 22, whereas a bright field image is formed on the image display device 17 when the sum signal W is selected by the selector 22.

Here, when the difference signal S is selected by the selector 22, the contrast of the differential interference image displayed on the image display device 17 changes depending on the polarization rotational angle due to the ½-wavelength plate 11 and, accordingly, depending on the analyzer angle of the polarizing beam splitter 12. Namely, also in the present embodiment, the contrast of the resulting differential interference image can be adjusted from maximum to minimum when the ½-wavelength plate 11 is appropriately rotated around its optical axis.

Third Embodiment

Figure 4:
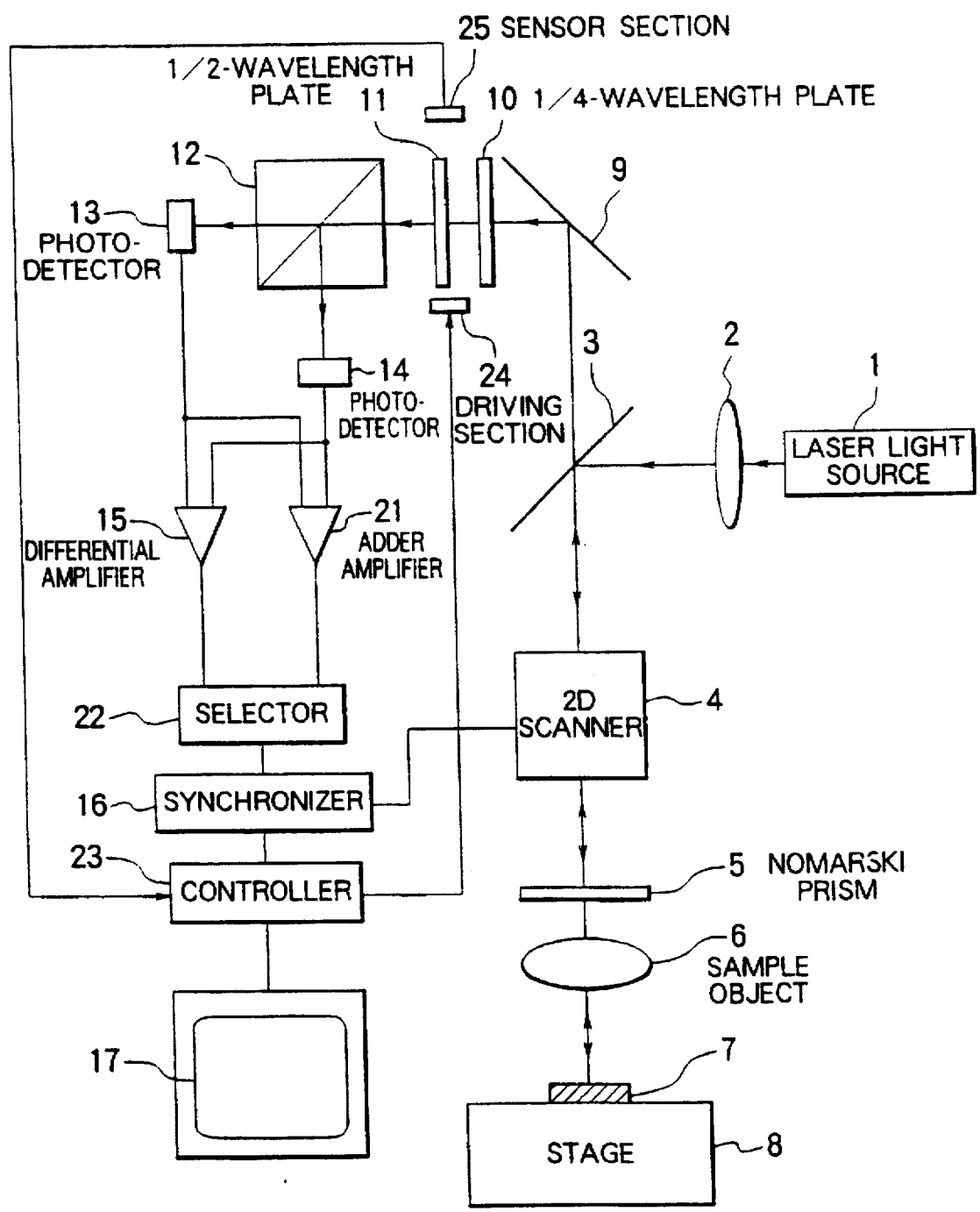
FIG. 4 is a block diagram schematically showing a configuration of a level-difference measuring apparatus as a third embodiment in accordance with the observation apparatus of the present invention.

As shown in FIG. 4, the level-difference measuring apparatus of this embodiment comprises the laser light source 1 which supplies, as spatially coherent light, a linearly polarized laser beam having a polarization direction which is in parallel to the paper surface of FIG. 4, for example. The laser beam from the laser light source 1 is turned into parallel light by way of the collimator lens 2 and then made incident on the half mirror 3.

The laser beam reflected by the half mirror 3 in a downward direction in the drawing is spatially deflected by the two-dimensional scanner 4 and then made incident on the Nomarski prism 5. The Nomarski prism 5 is a birefringence prism which has an optic axis intersecting the polarization direction of the incident laser beam at 45° and splits the incident laser beam into two light components according to their polarization characteristics.

The two light components split by the Nomarski prism 5 are converged by way of the objective lens 6 so as to form two laser spots on the sample object 7 such as a substrate mounted on the stage 8.

Thus, due to the operation of the Nomarski prism 5, two laser spots slightly distanced from each other are formed on the sample object 7. The object 7 is two-dimensionally scanned with these two laser spots according to the two-dimensional deflecting operation of the two-dimensional scanner 4.

Two reflected laser beams from the object 7 with respect to the two laser spots are transmitted through the objective lens 6 again and then combined together by way of the Nomarski prism 5.

Here, the inserting position of the Nomarski prism 5 with respect to the optical axis of the objective lens 6 is defined such that the Nomarski prism 5 imparts a phase difference of $\pi$ multiplied by an integer to the light components corresponding to the two laser spots as they travel therethrough to-and-fro. Accordingly, when the object 7 is of a flat surface having no level difference, i.e., a mirror surface, the phase difference between the two reflected laser beams by way of the Nomarski prism 5 becomes $\pi$ multiplied by an integer. In other words, the two reflected laser beams from the object 7 with respect to the two laser spots are combined together, by way of the Nomarski prism 5, into a linearly polarized laser beam having a polarization direction in parallel to the paper surface of FIG. 4.

The composite laser beam formed by way of the Nomarski prism 5 is turned into a parallel luminous flux again by way of the two-dimensional scanner 4 and then made incident on the half mirror 3. Here, the parallel luminous flux emitted from the two-dimensional scanner 4 attains a still state within the space since it has been subjected to the deflecting operation of the two-dimensional scanner 4 twice.

The composite laser beam transmitted through the half mirror 3 is made incident on the ¼-wavelength plate 10 by way of the mirror 9. The ¼-wavelength plate 10 is positioned so as to have an azimuth of $\pi/4$ with respect to the linear polarization direction of the composite linearly polarized laser beam which is incident on the ¼-wavelength plate 10 when the object 7 is of a mirror surface. Accordingly, when the object 7 is of a mirror surface, the laser beam emitted from the ¼-wavelength plate 10 becomes circularly polarized light and then is made incident on the ½-wavelength plate 11 which is rotatable around an optical axis conforming to the optical axis of the objective lens 6. Here, the ½-wavelength plate 11 is rotatably driven by a driving section 24, whereas the rotational angle of the ½-wavelength plate 11 is detected by a sensor section 25.

The laser beam emitted from the ½-wavelength plate 11 is separated into transmitted light and reflected light by a polarizing beam splitter 12. Thus, the ½-wavelength plate 11 is an analyzer whose polarization rotational angle is variable. The rotatable ½-wavelength plate 11 and the fixed polarizing beam splitter 12 constitute a polarizing beam splitter having a variable analyzer angle.

The light transmitted through the polarizing beam splitter 12 is detected and photoelectrically converted by the photodetector 13. On the other hand, the light reflected by the polarizing beam splitter 12 is detected and photoelectrically converted by the photodetector 14.

Each of the respective electric signals photoelectrically converted by the two photodetectors 13 and 14 is supplied to the differential amplifier 15 and the adder amplifier 21. The differential amplifier 15 determines the difference signal S based on the respective signals from the two photodetectors 13 and 14, whereas the adder amplifier 21 determines the sum signal W based on the respective signals from the two photodetectors 13 and 14. The difference signal S determined by the differential amplifier 15 and the sum signal W determined by the adder amplifier 21 are supplied to the selector 22. The selector 22 selects one of the difference signal S and sum signal W and supplies thus selected signal to the synchronizer 16.

The synchronizer 16 synchronizes information about the scanning position of the laser spots corresponding to the operation of the two-dimensional scanner 4 and the signal S or W from the selector 22 with each other and supplies them to a controller 23.

By way of the driving section 24, the controller 23 rotates the ½-wavelength plate 11 around its optical axis such that the difference signal S from the selector 22 is maximized (or minimized). The rotational angle of the ½-wavelength plate 11 (corresponding to the half value of the analyzer angle), from a predetermined position, at which the difference signal S from the selector 22 is maximized (or minimized) is detected by the sensor section 25 and then supplied to the controller 23.

As previously explained in conjunction with the operation of the present invention, the controller 23 calculates the level difference based on the rotational angle of the ½-wavelength plate 11 (i.e., analyzer angle) at which the difference signal S is maximized (or minimized). Thus calculated level difference data is supplied to the display device 17.

Also, the controller 23 forms an image based on the information about the scanning position of the laser spots and the signal S or W. Namely, the controller 23 forms a differential interference image when the difference signal S is selected by the selector 22, whereas it forms a bright field image when the sum signal W is selected by the selector 22. Thus formed differential interference image data or bright field image data is supplied to the display device 17.

Thus, the display device 17 displays, together with the measured value of the level difference, a differential interference image or bright field image in response to the switching of the selector 22. In this case, the profiles of the difference signal S and sum signal W are superposed on the displayed differential interference image and bright field image, respectively.

Figure 5A:
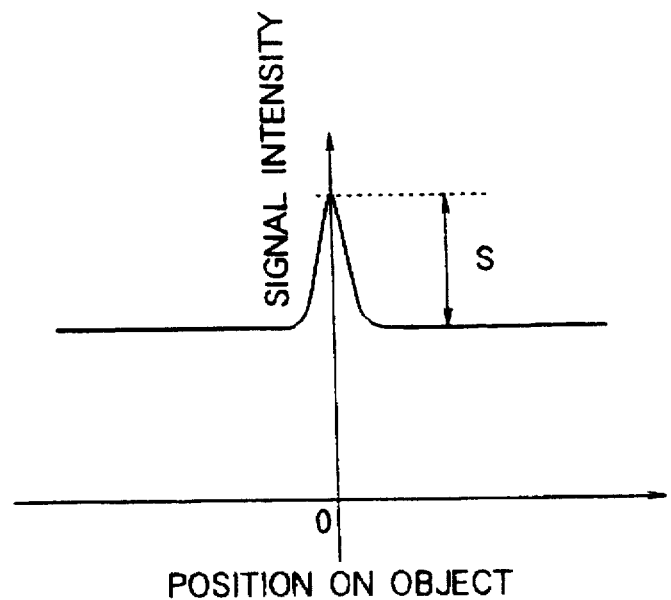
FIGS. 5A and 5B are graphs respectively showing typical profiles of the difference signal S and sum signal W in the level-difference measuring apparatus of FIG. 4.
Figure 5B:
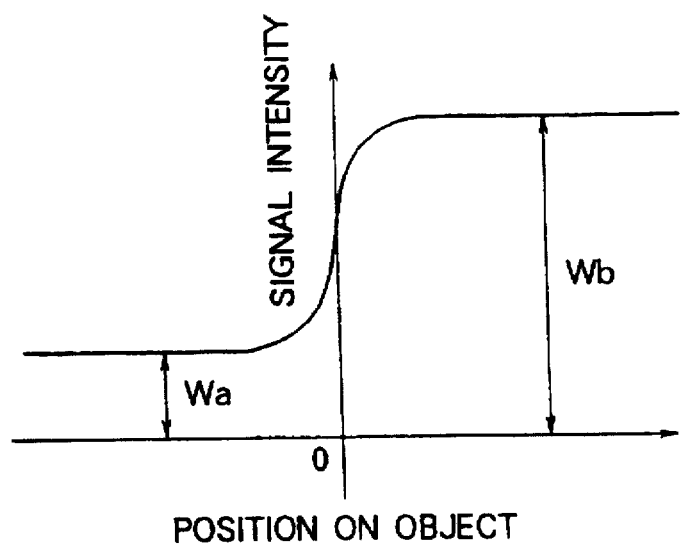

FIGS. 5A and 5B show typical profiles of the difference signal S and sum signal W, respectively. In these two graphs, the horizontal axis indicates the position of two laser spots on the object 7 along the direction of positional deviation (origin being the level difference position), whereas the vertical axis indicates the signal intensity at each position.

In a specific procedure for calculating the level difference, the right side value (or its inverse number) of expression (13) is determined on the basis of the analyzer angle at which the difference signal S in FIG. 5A is maximized (or minimized). On the other hand, based on the value of the sum signal $W_a$ in FIG. 5B, the amplitude reflectance a is determined from expression (16). Also, based on the value of the sum signal $W_b$ in FIG. 5B, the amplitude reflectance b is determined from an expression corresponding to expression (16). As previously explained in conjunction with the operation of the present invention, in order to determine the amplitude reflectances a and b, calibration is performed with an object whose reflectivity is known, thereby determining the apparatus constant of expression (16).

Thus, the phase difference $\Psi$ can be determined on the basis of the right side value (or its inverse number) of expression (13) and the amplitude reflectances a and b, while thus determined phase difference $\Psi$ can be input into expression (17) to calculate the level difference $\Delta h$.

In this manner, in this embodiment, an amount including the phase difference $\Psi$ is determined when the analyzer angle at which the difference signal S is qualitatively maximized or minimized is measured, namely, without the value of the difference signal S being quantitatively determined. Then, the phase difference $\Psi$ is calculated on the basis of the amplitude reflectances a and b on both sides of the level difference and the amount including the phase difference $\Psi$. Based on thus calculated phase difference $\Psi$, the level difference $\Delta h$ can be calculated. Accordingly, in this embodiment, any level difference can be measured with a high accuracy even when the light reflectivity changes between both sides of the level difference.

Fourth Embodiment

Figure 6:
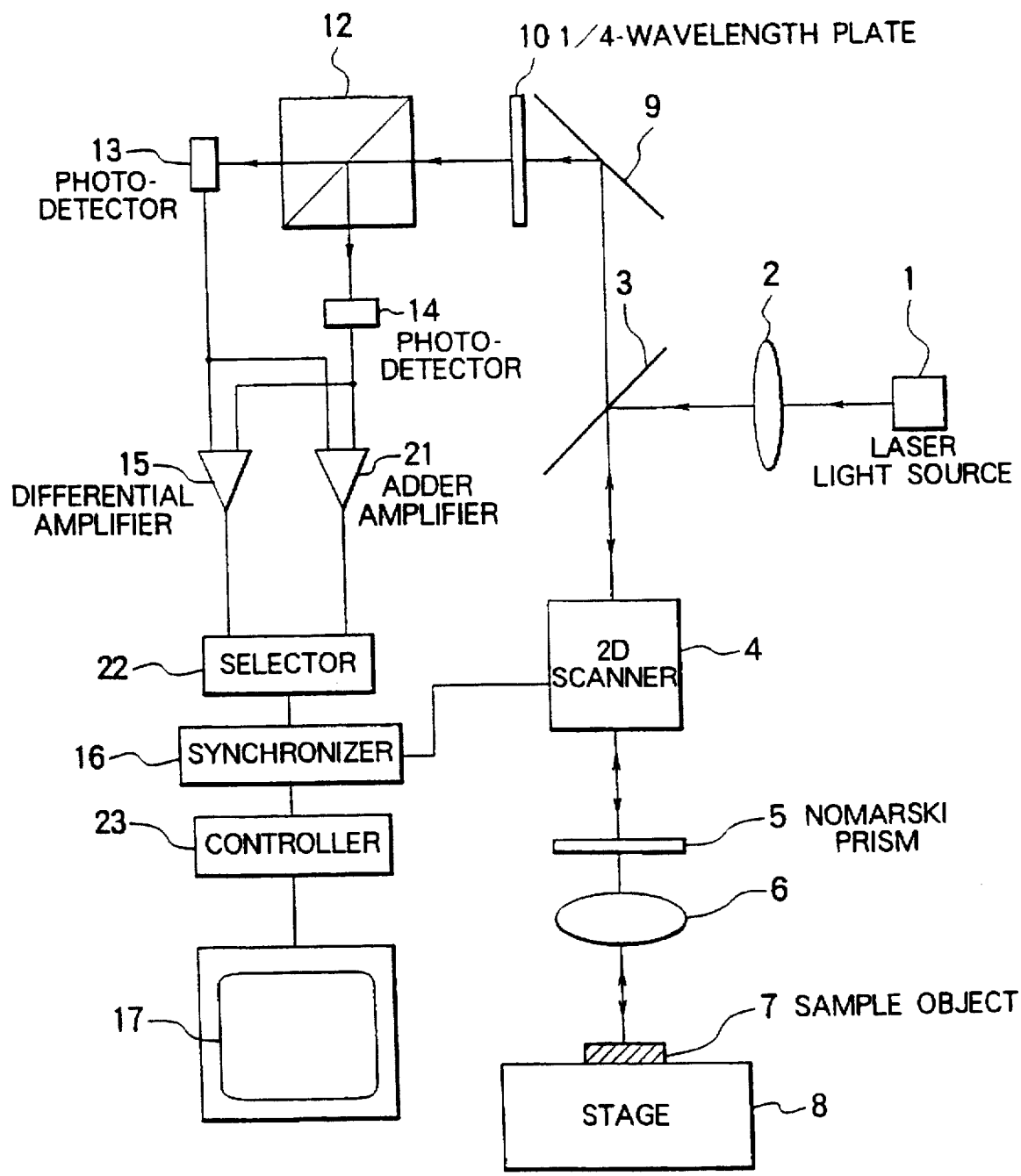
FIG. 6 is a block diagram schematically showing a configuration of a level-difference measuring apparatus as a fourth embodiment in accordance with the observation apparatus of the present invention.

As shown in FIG. 6, the level-difference measuring apparatus of this embodiment comprises the laser light source 1 which supplies, as spatially coherent light, a linearly polarized laser beam having a polarization direction which is in parallel to the paper surface of FIG. 6, for example. The laser beam from the laser light source 1 is turned into parallel light by way of the collimator lens 2 and then made incident on the half mirror 3.

The laser beam reflected by the half mirror 3 in a downward direction in the drawing is spatially deflected by the two-dimensional scanner 4 and then made incident on the Nomarski prism 5. The Nomarski prism 5 is a birefringence prism which has an optic axis intersecting the polarization direction of the incident laser beam at 45° and splits the incident laser beam into two light components according to their polarization characteristics.

The two light components split by the Nomarski prism 5 are converged by way of the objective lens 6 so as to form two laser spots on the sample object 7 such as a substrate mounted on the stage 8.

Thus, due to the operation of the Nomarski prism 5, two laser spots slightly distanced from each other are formed on the sample object 7. The object 7 is two-dimensionally scanned with these two laser spots according to the two-dimensional deflecting operation of the two-dimensional scanner 4.

Two reflected laser beams from the object 7 with respect to the two laser spots are transmitted through the objective lens 6 again and then combined together by way of the Nomarski prism 5.

Here, the inserting position of the Nomarski prism 5 with respect to the optical axis of the objective lens 6 is defined such that the Nomarski prism 5 imparts a phase difference of $\pi$ multiplied by an integer to the light components corresponding to the two laser spots as they travel therethrough to-and-fro. Accordingly, when the object 7 is of a flat surface having no level difference, namely, a mirror surface, the phase difference between the two reflected laser beams by way of the Nomarski prism 5 becomes $\pi$ multiplied by an integer. In other words, the two reflected laser beams from the object 7 with respect to the two laser spots are combined together, by way of the Nomarski prism 5, into a linearly polarized laser beam having a polarization direction in parallel to the paper surface of FIG. 6.

The composite laser beam formed by way of the Nomarski prism 5 is turned into a parallel luminous flux again by way of the two-dimensional scanner 4 and then made incident on the half mirror 3. Here, the parallel luminous flux emitted from the two-dimensional scanner 4 attains a still state within the space since it has been subjected to the deflecting operation of the two-dimensional scanner 4 twice.

The composite laser beam transmitted through the half mirror 3 is made incident on the ¼-wavelength plate 10 by way of the mirror 9. The ¼-wavelength plate 10 is positioned so as to have an azimuth of $\pi/4$ with respect to the linear polarization direction of the composite linearly polarized laser beam which is incident on the ¼-wavelength plate 10 when the object 7 is of a mirror surface. Accordingly, when the object 7 is of a mirror surface, the laser beam emitted from the ¼-wavelength plate 10 becomes circularly polarized light and then is made incident on the polarizing beam splitter 12 which is an analyzer.

Here, the polarizing beam splitter 12 is positioned such that the analyzer angle φ becomes π/4, whereby the incident laser beam is separated into transmitted light and reflected light.

The light transmitted through the polarizing beam splitter 12 is detected and photoelectrically converted by the photodetector 13. On the other hand, the light reflected by the polarizing beam splitter 12 is detected and photoelectrically converted by the photodetector 14.

Each of the respective electric signals photoelectrically converted by the two photodetectors 13 and 14 is supplied to the differential amplifier 15 and the adder amplifier 21. The differential amplifier 15 determines the difference signal S based on the respective signals from the two photodetectors 13 and 14, whereas the adder amplifier 21 determines the sum signal W based on the respective signals from the two photodetectors 13 and 14. The difference signal S determined by the differential amplifier 15 and the sum signal W determined by the adder amplifier 21 are supplied to the selector 22. The selector 22 selects one of the difference signal S and sum signal W and supplies thus selected signal to the synchronizer 16.

The synchronizer 16 synchronizes information about the scanning position of the laser spots corresponding to the operation of the two-dimensional scanner 4 and the signal S or W from the selector 22 with each other and supplies them to the controller 23.

As previously explained in conjunction with the operation of the present invention, the controller 23 calculates the level difference based on the difference signal S and sum signal W from the selector 22. Thus calculated level difference data is supplied to the display device 17.

Also, the controller 23 forms an image based on the information about the scanning position of the laser spots and the signal S or W. Namely, the controller 23 forms a differential interference image when the difference signal S is selected by the selector 22, whereas it forms a bright field image when the sum signal W is selected by the selector 22. Thus formed differential interference image data or bright field image data is supplied to the display device 17.

Thus, the display device 17 displays, together with the measured value of the level difference, a differential interference image or bright field image in response to the switching of the selector 22. In this case, the profiles of the difference signal S and sum signal W are superposed on the displayed differential interference image and bright field image, respectively.

FIGS. 5A and 5B show typical profiles of the difference signal S and sum signal W, respectively. In these two graphs, the horizontal axis indicates the position of two laser spots on the object 7 along the direction of positional deviation (origin being the level difference position), whereas the vertical axis indicates the signal intensity at each position.

In a specific procedure for calculating the level difference, the phase difference Ψ is determined from expression (19) on the basis of the difference signal S of FIG. 5A and the sum signals $W_a$ and $W_b$ in FIG. 5B. As previously explained in conjunction with the operation of the present invention, in order to determine the phase difference Ψ, calibration is performed with an object whose reflectivity is known, thereby determining the apparatus constant D of expression (19). Thus determined phase difference Ψ can be input into expression (17) to calculate the level difference Δh.

Thus, in this embodiment, the phase difference Ψ is calculated on the basis of expression (19) which is a relational expression between the difference signal S and the phase difference Ψ depending on the change in amplitude reflectance. Based on thus calculated phase difference Ψ, the level difference Δh can be calculated. Accordingly, in this embodiment, any level difference can be measured with a high accuracy even when the light reflectivity changes between both sides of the level difference.

Fifth Embodiment

Figure 7:
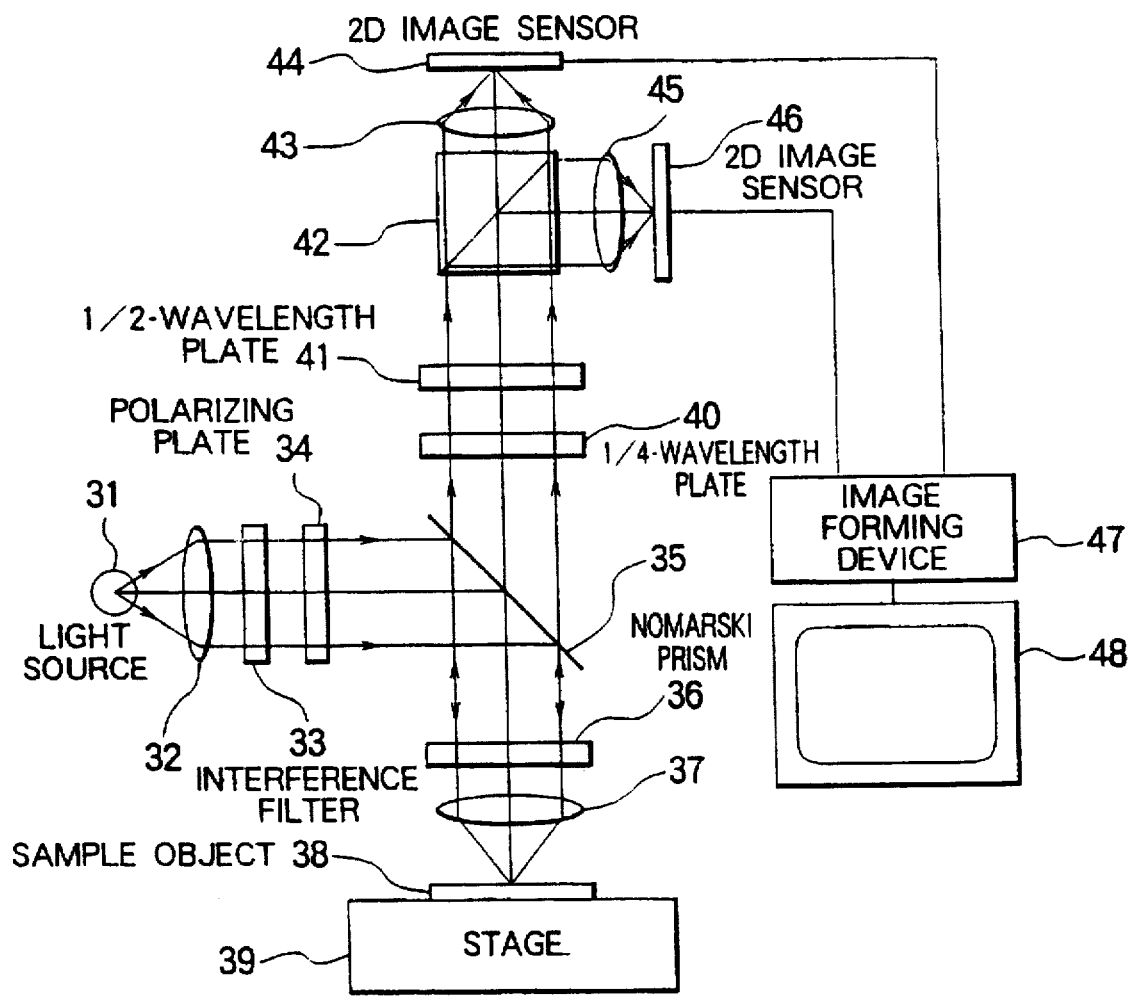
FIG. 7 is a block diagram schematically showing a configuration of a differential interference microscope as a fifth embodiment in accordance with the observation apparatus of the present invention.

As shown in FIG. 7, in the differential interference microscope of this embodiment, light emitted from a light source 31, which is a tungsten lamp, is turned into parallel light as being transmitted through a collimator lens 32. Then, as it is transmitted through an interference filter 33, a wavelength thereof is selected. In this embodiment, the selected wavelength is 550 nm. The light transmitted through the interference filter 33 is turned into linearly polarized light by way of a polarizing plate 34 and then made incident on a half mirror 35. The polarization direction at this time is in parallel to the paper surface of FIG. 7.

The light reflected by the half mirror 35 in a downward direction in the drawing is made incident on a Nomarski prism 36. The Nomarski prism 36 is a birefringence prism which has an optic axis intersecting the polarization direction of the incident light at 45° and splits the incident light into two light components according to their polarization characteristics.

The two light components split by the Nomarski prism 36 are converged by way of an objective lens 37 so as to form two illumination light components on a sample object 38 mounted on a stage 39. Thus, due to an operation of the Nomarski prism 36, two illumination light components slightly distanced from each other are formed on the sample object 38. The two reflected light components from the sample object 38 with respect to the two illumination light components are transmitted through the objective lens 37 again and then combined together by way of the Nomarski prism 36.

Here, the inserting position of the Nomarski prism 36 with respect to the optical axis of the objective lens 37 is defined such that the Nomarski prism 36 imparts a phase difference of π multiplied by an integer to the two illumination light components as they travel therethrough to-and-fro. Accordingly, when the sample object 38 is of a flat surface having no level difference, namely, a mirror surface upon which the two illumination light components do not relatively change their wavelengths and phases, the phase difference between the two reflected light components by way of the Nomarski prism 36 becomes π multiplied by an integer. In other words, the two reflected light components from the sample object 38 with respect to the two illumination light components are combined together, by way of the Nomarski prism 36, into linearly polarized light having a polarization direction in parallel to the paper surface of FIG. 7.

The composite light formed by way of the Nomarski prism 36 is made incident on the half mirror 35. The composite light transmitted through the half mirror 35 is made incident on a ¼-wavelength plate 40. The ¼-wavelength plate 40 is positioned so as to have an azimuth of π/4 with respect to the linear polarization direction of the composite linearly polarized light which is incident on the ¼-wavelength plate 40 when the sample object is of a mirror surface. Accordingly, when the sample object 38 is of a mirror surface, the composite light emitted from the ¼-wavelength plate 40 becomes circularly polarized light and then is made incident on a ½-wavelength plate 41 which is rotatable around the optical axis of the objective lens 37.

The composite light emitted from the ½-wavelength plate 41 is separated into transmitted light and reflected light by a polarizing beam splitter 42. Thus, the ½-wavelength plate 41 is an analyzer whose polarization rotational angle is variable. The rotatable ½-wavelength plate 41 and the fixed polarizing beam splitter 42 constitute a polarizing beam splitter having a variable analyzer angle.

By way of an imaging lens 43, the light transmitted through the polarizing beam splitter 42 forms an image on a two-dimensional image sensor 44 and is photoelectrically converted thereby. On the other hand, by way of an imaging lens 45, the light reflected by the polarizing beam splitter 42 forms an image on a two-dimensional image sensor 46 and is photoelectrically converted thereby. The two-dimensional image sensors 44 and 46 have pixel configurations identical to each other, while their corresponding pixels are aligned so as to receive the reflected light from the identical position on the sample object 38. Here, an image sensor such as CCD (Charge Coupled Device) may be used as these two-dimensional image sensors. The respective electric signals photoelectrically converted by these two-dimensional sensors 44 and 46 are supplied to an image forming device 47.

The image forming device 47 determines the difference signal S of the photoelectrically converted electric signals for each pair of pixels respectively constituting the two-dimensional sensors 44 and 46 and displays it as a differential interference image on a monitor 48. Here, the contrast of the differential interference image displayed on the monitor 48 changes depending on the polarization rotational angle due to the ½-wavelength plate 41 and, accordingly, depending on the analyzer angle of the polarizing beam splitter 42. Namely, in the present embodiment, the contrast of the resulting differential interference image changes as the ½-wavelength plate 41 is appropriately rotated around its optical axis.

Here, the contrast of the differential interference image can be maximized when the polarization rotational angle due to the ¼-wavelength plate 41, i.e., analyzer angle, satisfies $\phi$ in the above-mentioned expression (13). Also, the contrast of the differential interference image can be minimized when an analyzer angle of $\phi$ in the above-mentioned expression (13) with $\pm\pi/4$ being added thereto is used as the ½-wavelength plate 41 is rotated. Namely, in the present embodiment, the contrast of the resulting differential interference image can be arbitrarily adjusted from maximum to minimum as the ½-wavelength plate 41 is appropriately rotated around its optical axis.

Sixth Embodiment

Figure 8:
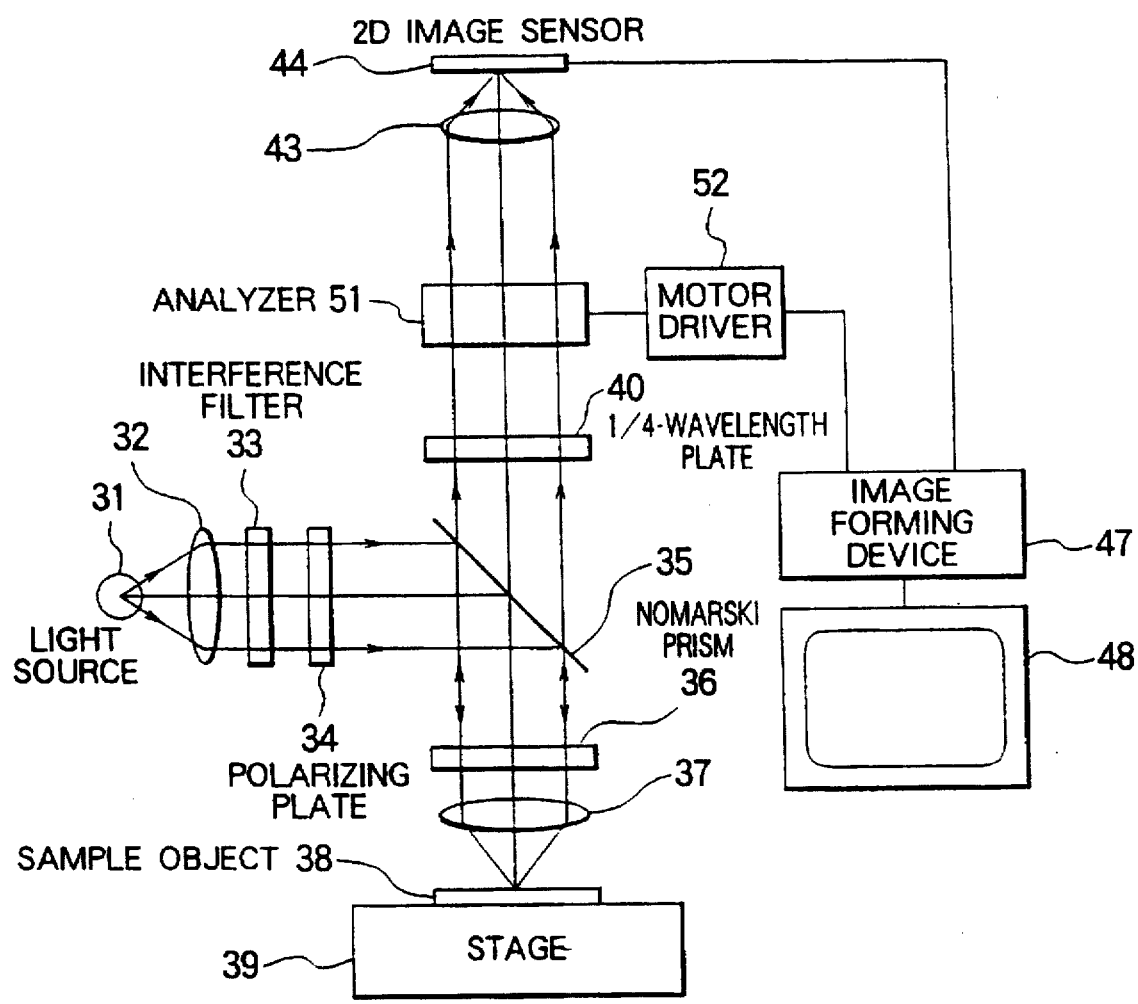
FIG. 8 is a block diagram schematically showing a configuration of a differential interference microscope as a sixth embodiment in accordance with the observation apparatus of the present invention.

As shown in FIG. 8, in the differential interference microscope of this embodiment, light emitted from the light source 31, which is a tungsten lamp, is turned into parallel light as being transmitted through the collimator lens 32. Then, as it is transmitted through the interference filter 33, a wavelength thereof is selected. In this embodiment, the selected wavelength is 550 nm. The light transmitted through the interference filter 33 is turned into linearly polarized light by way of the polarizing plate 34 and then made incident on the half mirror 35. The polarization direction at this time is in parallel to the paper surface of FIG. 8.

The light reflected by the half mirror 35 in a downward direction in the drawing is made incident on the Nomarski prism 36. The Nomarski prism 36 is a birefringence prism which has an optic axis intersecting the polarization direction of the incident laser beam at 45° and splits the incident light into two light components according to their polarization characteristics.

The two light components split by the Nomarski prism 36 are converged by way of the objective lens 37 so as to form two illumination light components on the sample object 38 mounted on the stage 39. Thus, due to the operation of the Nomarski prism 36, two illumination light components slightly distanced from each other are formed on the sample object 38. The two reflected light components from the sample object 38 with respect to the two illumination light components are transmitted through the objective lens 37 again and then combined together by way of the Nomarski prism 36.

Here, the inserting position of the Nomarski prism 36 with respect to the optical axis of the objective lens 37 is defined such that the Nomarski prism 36 imparts a phase difference of $\pi$ multiplied by an integer to the two illumination light components as they travel therethrough to-and-fro. Accordingly, when the sample object 38 is of a flat surface having no level difference, i.e., a mirror surface, the phase difference between the two reflected light components by way of the Nomarski prism 36 becomes $\pi$ multiplied by an integer. In other words, the two reflected light components from the sample object 38 with respect to the two illumination light components are combined together, by way of the Nomarski prism 38, into linearly polarized light having a polarization direction in parallel to the paper surface of FIG. 8.

The composite light formed by way of the Nomarski prism 36 is made incident on the half mirror 35. The composite light transmitted through the half mirror 35 is made incident on the ¼-wavelength plate 40. The ¼-wavelength plate 40 is positioned so as to have an azimuth of $\pi/4$ with respect to the linear polarization direction of the composite linearly polarized light which is incident on the ¼-wavelength plate 40 when the sample object is of a mirror surface. Accordingly, when the sample object 38 is of a mirror surface, the composite light emitted from the ¼-wavelength plate 40 becomes circularly polarized light and then is made incident on an analyzer 51. The analyzer 51 is constituted by a polarizing plate which is rotatable around the optical axis of the objective lens 37 and a motor which rotates the polarizing plate based on an analyzer angle signal output from a motor driver 52. The motor driver 52 supplies the analyzer angle of the analyzer 51, as an electric signal, to the image forming device 47.

By way of the imaging lens 43, the light transmitted through the analyzer 51 forms an image on a two-dimensional image sensor 44 and is photoelectrically converted thereby. The electric signal photoelectrically converted by the two-dimensional sensor 44 is supplied to the image forming device 47.

Based on the analyzer angle signal from the motor driver 52, at a predetermined analyzer angle such as $\phi 1$, the image forming device 47 captures the electric signal photoelectrically converted by the two-dimensional image sensor 44 and stores it in an image storage device accommodated therein. Then, when the analyzer angle becomes $\phi 1\pm n\pi/2$, it captures the electric signal photoelectrically converted by the two-dimensional image sensor 44 again, determines the difference signal S between thus captured signal and the image at the analyzer angle of $\phi 1$ stored in the image storage device for each pixel, and displays thus determined difference signal S on the monitor 48 as a differential interference image. Here, n is an odd number.

The contrast of the differential interference image displayed on the monitor 48 changes depending on the analyzer angle $\phi 1$ at which the image forming device 47 captures the image. Namely, in this embodiment, when the image-capturing timing for the image forming device 47 is changed, the contrast of the final differential interference image can be changed.

Also, the contrast of the differential interference image can be maximized when the analyzer angle $\phi 1$ at which the image forming device 47 captures the image satisfies $\phi$ in the above-mentioned expression (13). The contrast of the differential interference image can be minimized when the analyzer angle $\phi 1$ corresponds to $\phi$ in the above-mentioned expression (13) with $\pm \pi/4$ being added thereto. Namely, in this embodiment, when the image-capturing timing for the image forming device 47 is changed, the contrast of the resulting differential interference image can be arbitrarily adjusted from maximum to minimum. As explained in the foregoing, this embodiment can be distinguished from the fifth embodiment in that only one two-dimensional image sensor is used.

Seventh Embodiment

Figure 9:
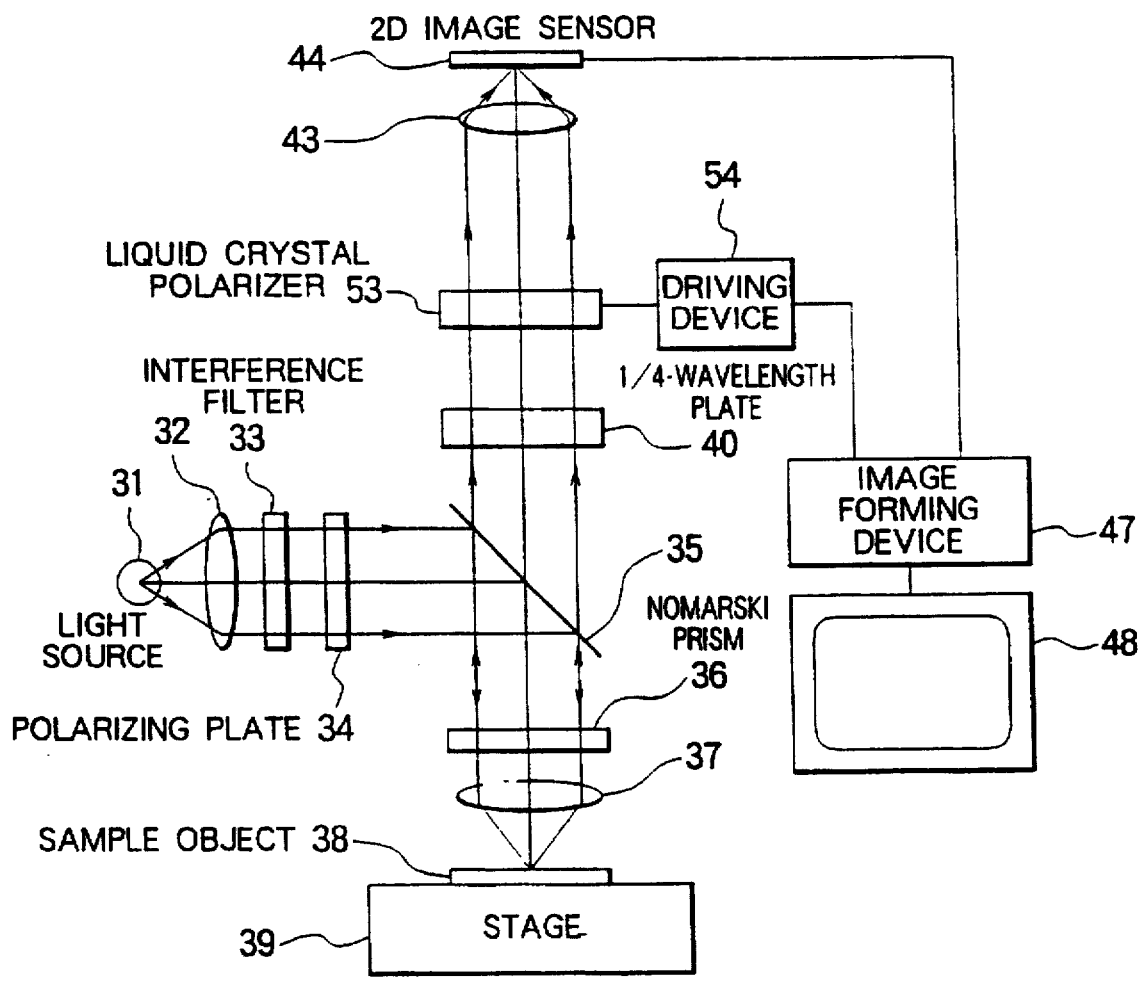
FIG. 9 is a block diagram schematically showing a configuration of a differential interference microscope as a seventh embodiment in accordance with the observation apparatus of the present invention.

As shown in FIG. 9, the differential interference microscope of this embodiment has mostly the same configuration as that of the differential interference microscope of the sixth embodiment. Accordingly, in FIG. 9, the constituents identical to those of the sixth embodiment are referred to with the marks identical thereto without repeating their overlapping explanations. Here, only the points different from the sixth embodiment will be explained.

In this embodiment, in place of the polarizing plate in the sixth embodiment which is rotated by a motor, a liquid crystal polarizer 53 is used. The liquid crystal polarizer 53 is controlled by a driving device 54 and functions as a polarizing plate whose polarization direction can be arbitrarily changed when the voltage applied thereto from the driving device 54 is arbitrarily changed, namely, as an analyzer whose analyzer angle can be arbitrarily set. The driving device 54 supplies the analyzer angle, as an electric signal, to the image forming device 47.

By way of the imaging lens 43, the light transmitted through the liquid crystal polarizer 53 forms an image on the two-dimensional image sensor 44 and is photoelectrically converted thereby. The signal photoelectrically converted by the two-dimensional image sensor 44 is supplied to the image forming device 47.

By setting the analyzer angle to a predetermined angle such as $\phi 1$ by way of the driving device 54, the image forming device 47 captures the electric signal photoelectrically converted by the two-dimensional image sensor 44 at this angle and stores it in an image storage device accommodated therein. Then, by changing the analyzer angle to $\phi 1 \pm n\pi/2$, it captures the electric signal photoelectrically converted by the two-dimensional image sensor 44 again, determines the difference signal S between thus captured signal and the image at the analyzer angle of $\phi 1$ stored in the image storage device for each pixel, and displays thus determined difference signal S on the monitor 48 as a differential interference image. Here, n is an odd number.

The contrast of the differential interference image displayed on the monitor 48 changes depending on the analyzer angle $\phi 1$ at which the image forming device 47 captures the image. Namely, in this embodiment, when the analyzer angle set by the image forming device 47 by way of the driving device 54 is changed, the contrast of the resulting differential interference image can be changed.

This embodiment can constitute the differential interference microscope of the present invention without using two sets of two-dimensional image sensors, unlike the fifth embodiment, and without using a mechanical movable section such as that used in the fifth and sixth embodiments.

Eighth Embodiment

Figure 10:
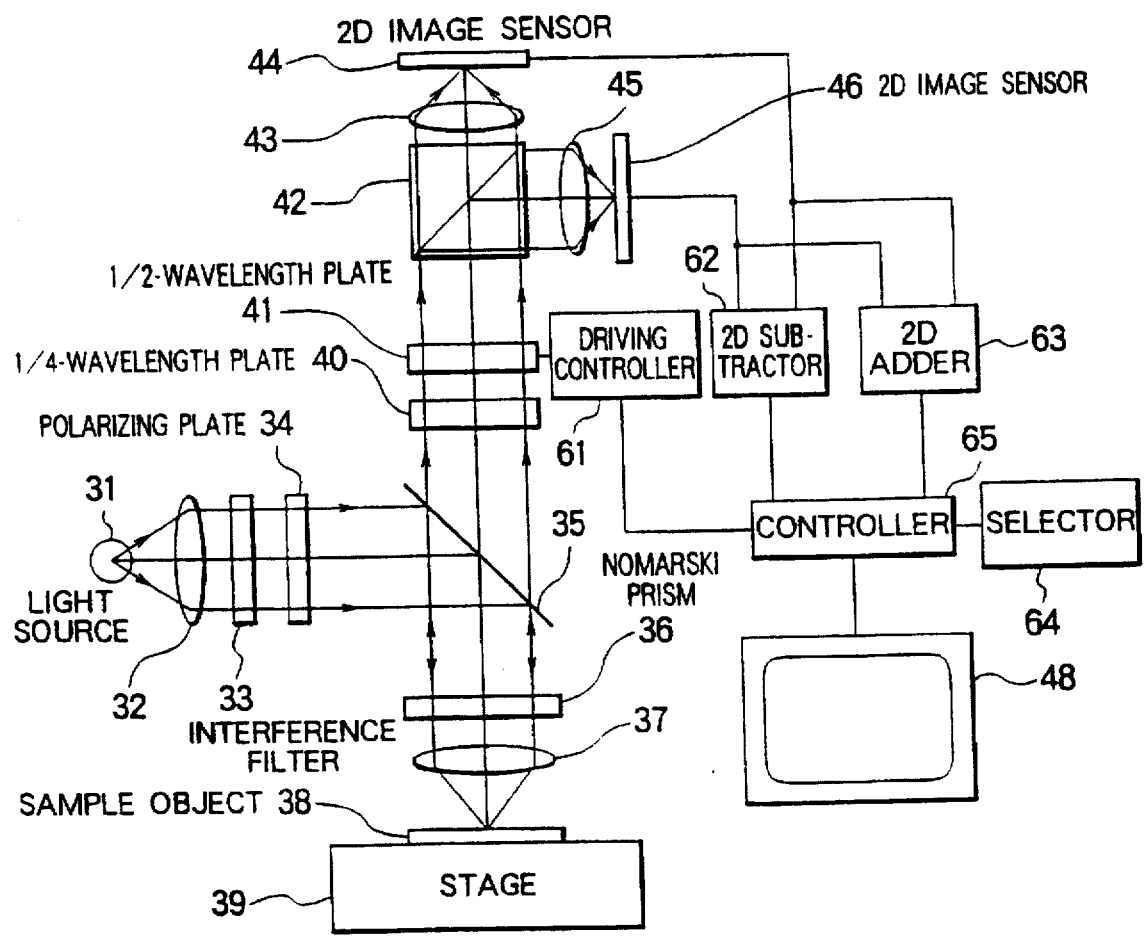
FIG. 10 is a block diagram schematically showing a configuration of a level-difference measuring apparatus as an eighth embodiment in accordance with the observation apparatus of the present invention.

In the level-difference measuring apparatus of this embodiment, though the light source 31 is depicted as a point light source in FIG. 10 in order to facilitate explanation, it is actually a light source such as tungsten lamp which has a definite size.

The light emitted from the light source 31 is turned into parallel light as being transmitted through the collimator lens 32. Then, as it is transmitted through the interference filter 33, a wavelength thereof is selected. In this embodiment, the selected wavelength is 550 nm. The light transmitted through the interference filter 33 is turned into linearly polarized light by way of the polarizing plate 34 and then made incident on the half mirror 35. The polarization direction at this time is in parallel to the paper surface of FIG. 10.

The light reflected by the half mirror 35 in a downward direction in the drawing is made incident on the Nomarski prism 36. The Nomarski prism 36 is a birefringence prism which has an optic axis intersecting the polarization direction of the incident laser beam at 45° and splits the incident light into two light components according to their polarization characteristics. Here, in place of the Nomarski prism, a Wallaston prism or the like may also be used.

The two light components split by the Nomarski prism 36 are converged by way of the objective lens 37 so as to form two illumination light components on the sample object 38 mounted on the stage 39. Thus, due to the operation of the Nomarski prism 36, two illumination light components slightly distanced from each other at their centers are formed on the sample object 38. The two reflected light components from the sample object 38 with respect to the two illumination light components are transmitted through the objective lens 37 again and then combined together by way of the Nomarski prism 36.

Here, the inserting position of the Nomarski prism 36 with respect to the optical axis of the objective lens 37 is defined such that the Nomarski prism 36 imparts a phase difference of $\pi$ multiplied by an integer to the two illumination light components as they travel therethrough to-and-fro. Accordingly, when the sample object 38 is of a flat surface providing no change in reflectivity, i.e., a mirror surface, the phase difference between the two reflected light components by way of the Nomarski prism 36 becomes $\pi$ multiplied by an integer. In other words, the two reflected light components from the sample object 38 with respect to the two illumination light components are combined together, by way of the Nomarski prism 38, into linearly polarized light having a polarization direction in parallel to or perpendicular to the paper surface of FIG. 10.

The composite light formed by way of the Nomarski prism 36 is made incident on the half mirror 35. The composite light transmitted through the half mirror 35 is made incident on the ¼-wavelength plate 40.

The ¼-wavelength plate 40 is positioned so as to have an azimuth of $\pi/4$ with respect to the linear polarization direction of the composite linearly polarized light which is incident on the ¼-wavelength plate 40 when the sample object is of a mirror surface. Accordingly, when the sample object 38 is of a mirror surface, the composite light emitted from the ¼-wavelength plate 40 becomes circularly polarized light and then is made incident on the ½-wavelength plate 41 which is rotatable around the optical axis of the objective lens 37. Here, the ½-wavelength plate 41 has a driving device by which it is rotated to an arbitrary angle according to a signal from a driving controller 61. The driving controller 61 supplies the rotational angle of the ½-wavelength plate to a controller 65.

The light transmitted through the ½-wavelength plate 41 is separated into transmitted light and reflected light by the polarizing beam splitter 42. Thus, the ½-wavelength plate 41 is an analyzer whose polarization rotational angle is variable. The rotatable ½-wavelength plate 41 and the fixed polarizing beam splitter 42 constitute a polarizing beam splitter having a variable analyzer angle.

By way of the imaging lens 43, the light transmitted through the polarizing beam splitter 42 forms an image on the two-dimensional image sensor 44 and is photoelectrically converted thereby. On the other hand, by way of the imaging lens 45, the light reflected by the polarizing beam splitter 42 forms an image on the two-dimensional image sensor 46 and is photoelectrically converted thereby. The two-dimensional image sensors 44 and 46 have pixel configurations identical to each other, while their corresponding pixels are aligned so as to receive the reflected light from the identical position on the sample object 38. Here, an image sensor such as CCD may be used as these two-dimensional image sensors.

Each of the respective electric signals photoelectrically converted by these two-dimensional sensors 44 and 46 is supplied to a two-dimensional subtractor 62 and a two-dimensional adder 63. The two-dimensional subtractor 62 determines the difference signal S for each pixel based on the respective signals from the two-dimensional image sensors 44 and 46, whereas the two-dimensional adder 63 determines the sum signal W for each pixel based on the respective signals from the two-dimensional image sensors 44 and 46. The difference signal S determined by the two-dimensional subtractor 62 and the sum signal W determined by the two-dimensional adder 63 are supplied to the controller 65.

By way of the driving controller 61, the controller 65 rotates the ½-wavelength plate 41 around its optical axis such that the difference signal S from the subtractor 62 is maximized (or minimized). The rotational angle of the ½-wavelength plate 41 (corresponding to the half value of the analyzer angle), from a predetermined position, at which the difference signal S from the subtractor 62 is maximized (or minimized) is detected by the driving controller 61 and then supplied to the controller 65.

As previously explained in conjunction with the operation of the present invention, the controller 65 calculates the level difference based on the rotational angle of the ½-wavelength plate 41 (i.e., analyzer angle) at which the difference signal S is maximized (or minimized). Thus calculated level difference data is supplied to the display device 48.

Also, according to an instruction from a selector 64, the controller 65 supplies an image data based on the difference signal S or sum signal W to the display device 48 together with the measured value of the level difference. Namely, the controller 65 supplies a differential interference image when the difference signal S is selected by the selector 64, whereas it supplies a bright field image when the sum signal W is selected by the selector 64. Thus, the display device 48 displays, together with the measured value of the level difference, a differential interference image or bright field image in response to the switching of the selector 64. In this case, the profiles of the difference signal S and sum signal W are superposed on the displayed differential interference image and bright field image, respectively.

Figure 11A:
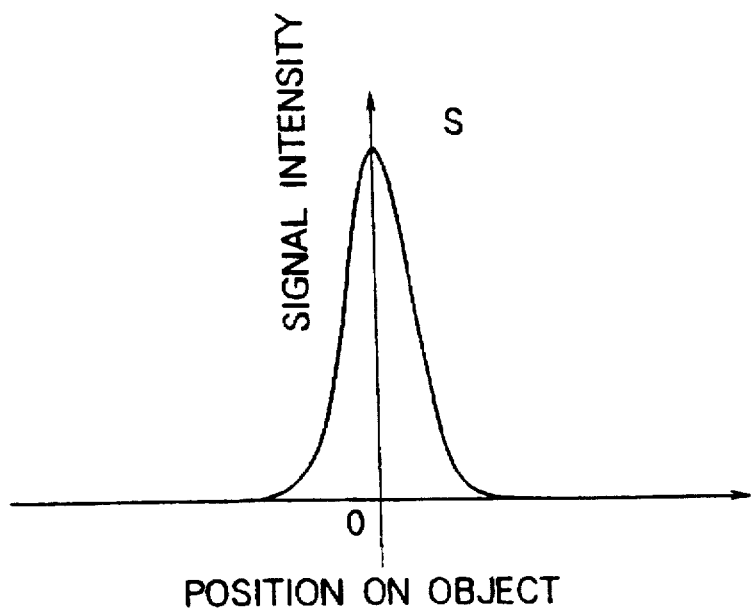
FIGS. 11A and 11B are graphs respectively showing typical profiles of the difference signal S and sum signal W in the level-difference measuring apparatus of FIG. 10.
Figure 11B:
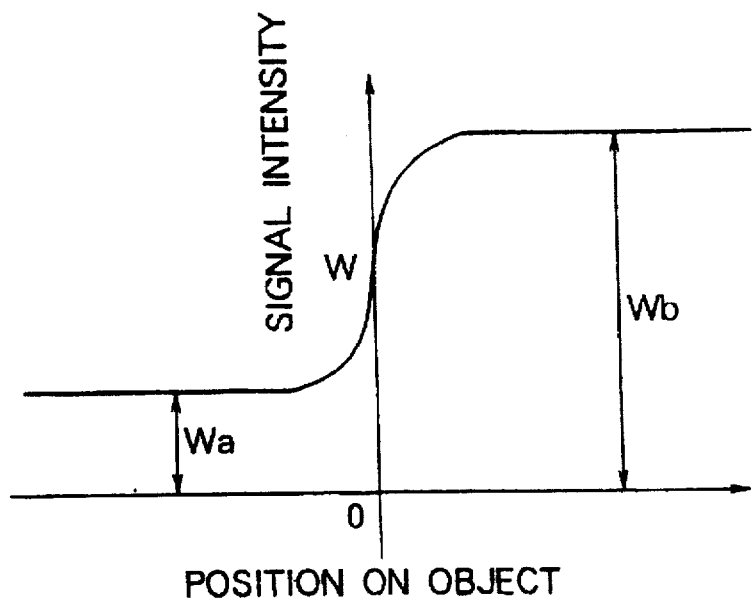

FIGS. 11A and 11B show typical profiles of the difference signal S and sum signal W, respectively. In these two graphs, the horizontal axis indicates the position of two light components on the sample object 38 along the direction of positional deviation (origin being the level difference position), whereas the vertical axis indicates the signal intensity at each position.

In a specific procedure for calculating the level difference, the right side value (or its inverse number) of expression (13) is determined on the basis of the analyzer angle at which the difference signal S in FIG. 11A is maximized (or minimized). On the other hand, based on the value of the sum signal $W_a$ in FIG. 11B, the amplitude reflectance a is determined from expression (16). Also, based on the value of the sum signal $W_b$ in FIG. 11B, the amplitude reflectance b is determined from an expression corresponding to expression (16). As previously explained in conjunction with the operation of the present invention, in order to determine the amplitude reflectances a and b, calibration is performed with an object whose reflectivity is known, thereby determining the apparatus constant of expression (16).

Also, when a level difference image exists in a certain pixel in the two-dimensional image sensors 44 and 46, the outputs of pixels in front of and behind this pixel or in the left and right of this pixel are used for the sum signals $W_a$ and $W_b$. In this case, according to the resolution of the two-dimensional sensors, the sample object, and the like, appropriate pixels are selected as the pixels in front of and behind or in the left and right of the certain pixel.

Thus, the phase difference $\Psi$ can be determined on the basis of the right side value (or its inverse number) of expression (13) and the amplitude reflectances a and b, while thus determined phase difference $\Psi$ can be input into expression (17) to calculate the level difference $\Delta h$.

In this manner, in this embodiment, an amount including the phase difference $\Psi$ is determined when the analyzer angle at which the difference signal S is qualitatively maximized or minimized is measured, namely, without the value of the difference signal S being quantitatively determined. Then, the phase difference $\Psi$ is calculated on the basis of the amplitude reflectances a and b on both sides of the level difference and the amount including the phase difference $\Psi$. Based on thus calculated phase difference $\Psi$, the level difference $\Delta h$ can be calculated. Accordingly, in this embodiment, any level difference can be measured with a high accuracy even when the light reflectivity changes between both sides of the level difference.

Ninth Embodiment

Figure 12:
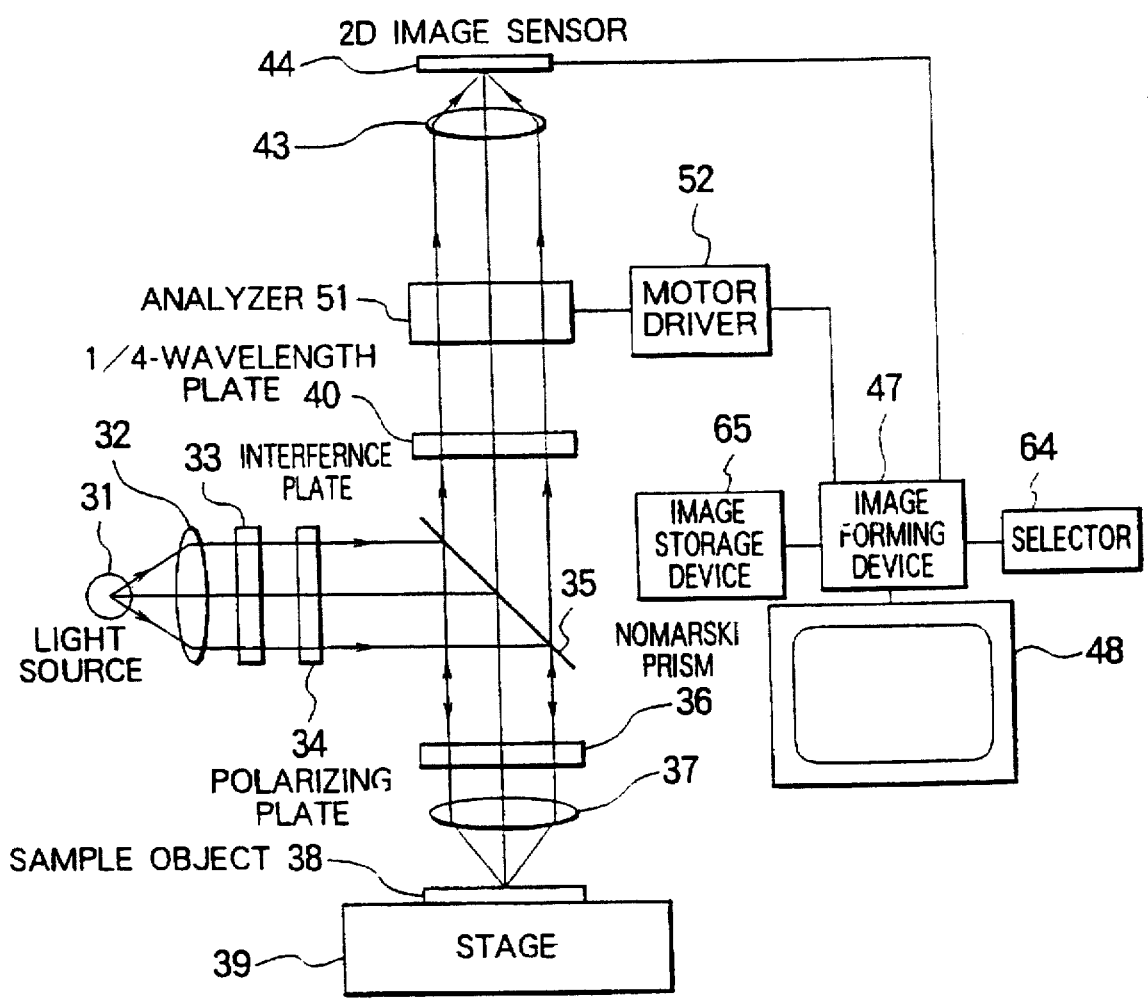
FIG. 12 is a block diagram schematically showing a configuration of a level-difference measuring apparatus as a ninth embodiment in accordance with the observation apparatus of the present invention.

As shown in FIG. 12, the level-difference measuring apparatus of this embodiment uses the light source, illumination optical system, and the like which are similar to those of the eighth embodiment.

The light emitted from the light source 31, which is a tungsten lamp, is turned into parallel light as being transmitted through the collimator lens 32. Then, as it is transmitted through the interference filter 33, a wavelength thereof is selected. In this embodiment, the selected wavelength is 550 nm. The light transmitted through the interference filter 33 is turned into linearly polarized light by way of the polarizing plate 34 and then made incident on the half mirror 35. The polarization direction at this time is in parallel to the paper surface of FIG. 12.

The light reflected by the half mirror 35 in a downward direction in the drawing is made incident on the Nomarski prism 36. The Nomarski prism 36 is a birefringence prism which has an optic axis intersecting the polarization direction of the incident laser beam at 45° and splits the incident light into two light components according to their polarization characteristics.

The two light components split by the Nomarski prism 36 are converged by way of the objective lens 37 so as to form two illumination light components on the sample object 38 mounted on the stage 39. Thus, due to the operation of the Nomarski prism 36, two illumination light components slightly distanced from each other at their centers are formed on the sample object 38. The two reflected light components from the sample object 38 with respect to the two illumination light components are transmitted through the objective lens 37 again and then combined together by way of the Nomarski prism 36.

Here, the inserting position of the Nomarski prism 36 with respect to the optical axis of the objective lens 37 is defined such that the Nomarski prism 36 imparts a phase difference of $\pi$ multiplied by an integer to the two illumination light components as they travel therethrough to-and-fro. Accordingly, when the sample object 38 is of a flat surface providing no change in reflectivity, i.e., a mirror surface, the phase difference between the two reflected light components by way of the Nomarski prism 36 becomes $\pi$ multiplied by an integer. In other words, the two reflected light components from the sample object 38 with respect to the two illumination light components are combined together, by way of the Nomarski prism 38, into linearly polarized light having a polarization direction in parallel to or perpendicular to the paper surface of FIG. 12. The composite light formed by way of the Nomarski prism 36 is made incident on the half mirror 35.

The composite light transmitted through the half mirror 35 is made incident on the ¼-wavelength plate 40. The ¼-wavelength plate 40 is positioned so as to have an azimuth of $\pi/4$ with respect to the linear polarization direction of the composite linearly polarized light which is incident on the ¼-wavelength plate 40 when the sample object is of a mirror surface. Accordingly, when the sample object 38 is of a mirror surface, the composite light emitted from the ¼wavelength plate 40 becomes circularly polarized light and then is made incident on the analyzer 51. The analyzer 51 is constituted by a polarizing plate which is rotatable around the optical axis of the objective lens 37 and a motor which rotates the polarizing plate on the basis of an analyzer angle signal output from the motor driver 52. Here, the motor driver 52 supplies the analyzer angle of the analyzer 51, as an electric signal, to the image forming device 47.

By way of the imaging lens 43, the light transmitted through the analyzer 51 forms an image on the two-dimensional image sensor 44 and is photoelectrically converted thereby. The signal photoelectrically converted by the two-dimensional image sensor 44 is supplied to the image forming device 47.

Based on the analyzer angle signal from the motor driver 52, at a predetermined analyzer angle such as $\phi 1$, the image forming device 47 captures the electric signal photoelectrically converted by the two-dimensional image sensor 44 and stores it in an image storage device 65. Then, when the analyzer angle becomes $\phi 1+\pi/2$ (or $-\pi/2$), it captures the electric signal photoelectrically converted by the two-dimensional image sensor 44 again and calculates, for each pixel, the difference signal S between thus captured signal and the image at the analyzer angle of $\phi 1$ stored in the image storage device 65 as well as their sum signal W. The image forming device 47 repeatedly performs this capturing and calculating operation of electric signals for every $\phi 1$.

As previously explained in conjunction with the operation of the present invention, the image forming device 47 calculates the level difference based on the analyzer angle of the analyzer 51 at which the difference signal S is maximized (or minimized). Thus calculated level difference data is supplied to the display device 48.

Here, the polarizing plate of the analyzer 51 may be always rotated while the image forming device 47 measures and stores the analyzer angle $\phi 1$ at which the difference signal S is maximized or minimized. In this case, only the electric signals output from the two-dimensional image sensor at the analyzer angles of $\phi 1$ and $\phi 1+\pi/2$ (or $-\pi/2$) may be captured and stored such that the above-mentioned difference signal S and sum signal W are calculated therefrom.

Further, according to an instruction from the selector 64, the image forming device 47 supplies an image data based on the difference signal S or sum signal W to the display device 48 together with the measured value of the level difference. Namely, the image forming device 47 supplies a differential interference image when the difference signal S is selected by the selector 64, whereas it supplies a bright field image when the sum signal W is selected by the selector 64.

Thus, the display device 48 displays, together with the measured value of the level difference, a differential interference image or bright field image in response to the switching of the selector 64. In this case, the profiles of the difference signal S and sum signal W are superposed on the displayed differential interference image and bright field image, respectively. Subsequently, as in the case of the eighth embodiment in accordance with the present invention, the level difference $\Delta h$ can be calculated.

Tenth Embodiment

Figure 13:
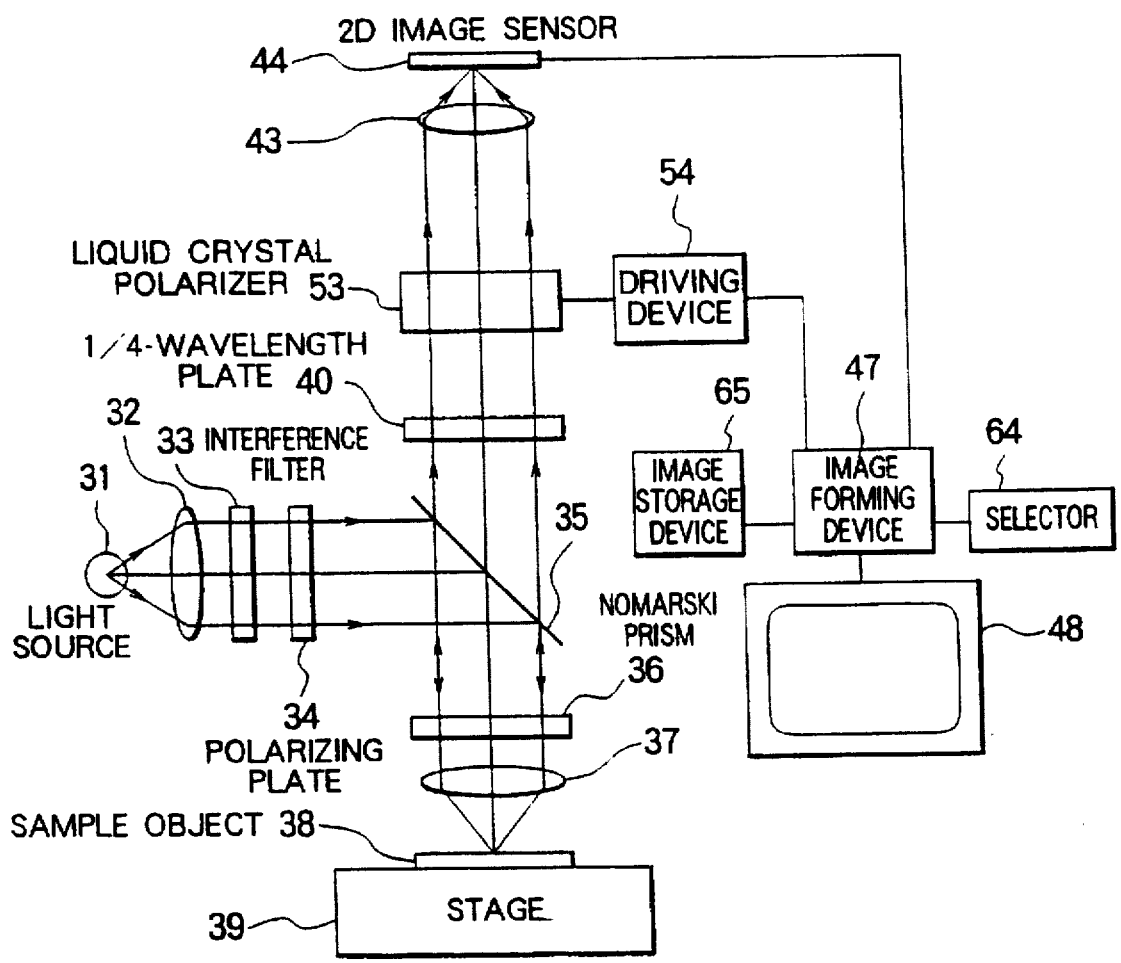
FIG. 13 is a block diagram schematically showing a configuration of a level-difference measuring apparatus as a tenth embodiment in accordance with the observation apparatus of the present invention.

As shown in FIG. 13, the level-difference measuring apparatus of this embodiment has mostly the same configuration as that of the level-difference measuring apparatus of the ninth embodiment. Accordingly, in FIG. 13, the constituents identical to those of the ninth embodiment are referred to with the marks identical thereto without repeating their overlapping explanations. Here, only the points different from the ninth embodiment will be explained.

In this embodiment, in place of the polarizing plate in the ninth embodiment which is rotated by a motor, the liquid crystal polarizer 53 is used. The liquid crystal polarizer 53 functions as a polarizing plate whose polarization direction can be arbitrarily changed when the voltage applied thereto from the driving device 54 is arbitrarily changed, namely, as an analyzer whose analyzer angle can be arbitrarily set. The driving device 54 supplies the analyzer angle, as an electric signal, to the image forming device 47.

By way of the imaging lens 43, the light transmitted through the liquid crystal polarizer 53 forms an image on the two-dimensional image sensor 44 and is photoelectrically converted thereby. The signal photoelectrically converted by the two-dimensional image sensor 44 is supplied to the image forming device 47.

Based on the analyzer angle signal from the driving device 54, at a predetermined analyzer angle such as $\phi 1$, the image forming device 47 captures the electric signal photoelectrically converted by the two-dimensional image sensor 44 and stores it in the image storage device 65. Then, when the analyzer angle becomes $\phi 1+\pi/2$ (or $-\pi/2$), it captures the electric signal photoelectrically converted by the two-dimensional image sensor 44 again and calculates, for each pixel, the difference signal S between thus captured signal and the image at the analyzer angle of $\phi 1$ stored in the image storage device 65 as well as their sum signal W. The image forming device 47 repeatedly performs this capturing and calculating operation of electric signals for every $\phi 1$. Subsequently, as in the case of the ninth embodiment, the level difference $\Delta h$ can be calculated.

Eleventh Embodiment

Figure 14:
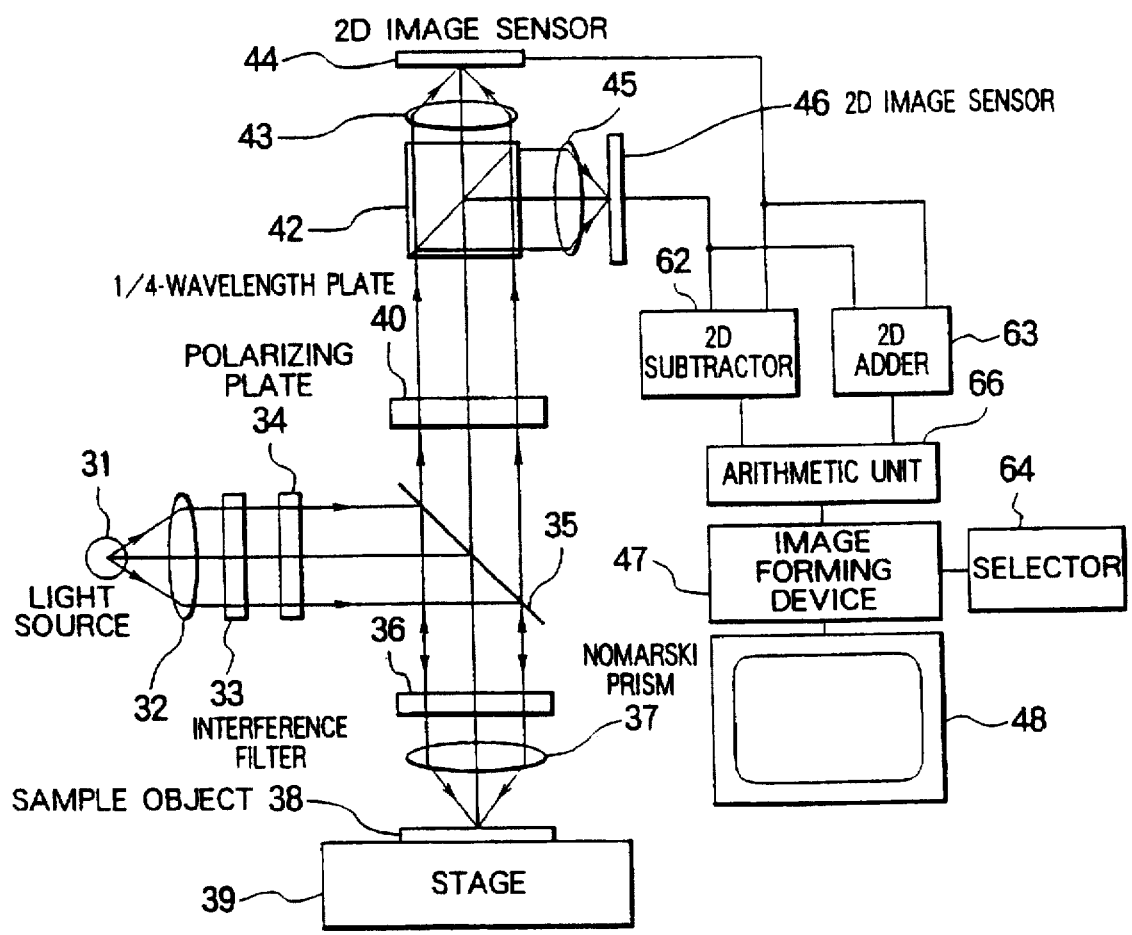
FIG. 14 is a block diagram schematically showing a configuration of a level-difference measuring apparatus as an eleventh embodiment in accordance with the observation apparatus of the present invention.

In the level-difference measuring apparatus of this embodiment, though the light source 31 is depicted as a point light source in FIG. 14 in order to facilitate explanation, it is actually a light source such as tungsten lamp which has a definite size.

The light emitted from the light source 31 is turned into parallel light as being transmitted through the collimator lens 32. Then, as it is transmitted through the interference filter 33, a wavelength thereof is selected. In this embodiment, the selected wavelength is 550 nm. The light transmitted through the interference filter 33 is turned into linearly polarized light by way of the polarizing plate 34 and then made incident on the half mirror 35. The polarization direction at this time is in parallel to the paper surface of FIG. 14.

The light reflected by the half mirror 35 in a downward direction in the drawing is made incident on the Nomarski prism 36. The Nomarski prism 36 is a birefringence prism which has an optic axis intersecting the polarization direction of the incident laser beam at 45° and splits the incident light into two light components according to their polarization characteristics. Here, in place of the Nomarski prism, a Wallaston prism or the like may also be used.

The two light components split by the Nomarski prism 36 are converged by way of the objective lens 37 so as to form two illumination light components on the sample object 38 mounted on the stage 39. Thus, due to the operation of the Nomarski prism 36, two illumination light components slightly distanced from each other at their centers are formed on the sample object 38. The two reflected light components from the object 38 with respect to the two illumination light components are transmitted through the objective lens 37 again and then combined together by way of the Nomarski prism 36.

Here, the inserting position of the Nomarski prism 36 with respect to the optical axis of the objective lens 37 is defined such that the Nomarski prism 36 imparts a phase difference of $\pi$ multiplied by an integer to the two illumination light components as they travel therethrough to-and-fro. Accordingly, when the sample object 38 is of a flat surface providing no change in reflectivity, i.e., a mirror surface, the phase difference between the two reflected light components by way of the Nomarski prism 36 becomes $\pi$ multiplied by an integer. In other words, the two reflected light components from the object 38 with respect to the two illumination light components are combined together, by way of the Nomarski prism 38, into linearly polarized light having a polarization direction in parallel to or perpendicular to the paper surface of FIG. 14.

The composite light formed by way of the Nomarski prism 36 is made incident on the half mirror 35. The composite light transmitted through the half mirror 35 is made incident on the ¼-wavelength plate 40.

The ¼-wavelength plate 40 is positioned so as to have an azimuth of $\pi/4$ with respect to the linear polarization direction of the composite linearly polarized light which is incident on the ¼-wavelength plate 40 when the sample object 38 is of a mirror surface. Accordingly, when the sample object 38 is of a mirror surface, the composite light emitted from the ¼-wavelength plate 40 becomes circularly polarized light and then is made incident on the polarizing beam splitter 42 which is an analyzer.

The polarizing beam splitter 42 is positioned such that the analyzer angle $\phi$ becomes $\pi/4$ and separates incident light into transmitted light and reflected light. By way of the imaging lens 43, the light transmitted through the polarizing beam splitter 42 forms an image on the two-dimensional image sensor 44 and is photoelectrically converted thereby. On the other hand, by way of the imaging lens 45, the light reflected by the polarizing beam splitter 42 forms an image on the two-dimensional image sensor 46 and is photoelectrically converted thereby. The two-dimensional image sensors 44 and 46 have pixel configurations identical to each other, while their corresponding pixels are aligned so as to receive the reflected light from the identical position on the sample object 38. Here, an image sensor such as CCD are used as these two-dimensional image sensors.

Each of the respective electric signals photoelectrically converted by these two-dimensional sensors 44 and 46 is supplied to the two-dimensional subtractor 62 and the two-dimensional adder 63. The two-dimensional subtractor 62 determines the difference signal S for each pixel based on the respective signals from the two-dimensional image sensors 44 and 46, whereas the two-dimensional adder 63 determines the sum signal W for each pixel based on the respective signals from the two-dimensional image sensors 44 and 46. The difference signal S determined by the two-dimensional subtractor 62 and the sum signal W determined by the two-dimensional adder 63 are supplied to an arithmetic unit 66.

As previously explained in conjunction with the operation of the present invention, the arithmetic unit 66 calculates the level difference based on the difference signal S and the sum signal W. The level difference data calculated by the arithmetic unit 66 is supplied to the image forming device 47 together with the difference signal S and the sum signal W.

Also, according to an instruction from the selector 64, the image forming device 47 supplies an image data based on the difference signal S or sum signal W to the display device 48 together with the measured value of the level difference. Namely, the image forming device 47 supplies a differential interference image when the difference signal S is selected by the selector 64, whereas it supplies a bright field image when the sum signal W is selected by the selector 64. Thus, the display device 48 displays, together with the measured value of the level difference, a differential interference image or bright field image in response to the switching of the selector 64. In this case, the profiles of the difference signal S and sum signal W are superposed on the displayed differential interference image and bright field image, respectively.

FIGS. 11A and 11B show typical profiles of the difference signal S and sum signal W, respectively. In these two graphs, the horizontal axis indicates the position of two illumination light components on the object 38 along the direction of positional deviation (origin being the level difference position), whereas the vertical axis indicates the signal intensity at each position.

In a specific procedure for calculating the level difference, the phase difference $\Psi$ is determined on the basis of the difference signal S of FIG. 11A and the sum signals $W_a$ and $W_b$ in FIG. 11B. Here, as previously explained in conjunction with the operation of the present invention, in order to determine the phase difference $\Psi$, calibration is performed with an object whose reflectivity is known, thereby determining the apparatus constant D of expression (19).

Also, when a level difference image exists in a certain pixel in the two-dimensional image sensors 44 and 46, the outputs of pixels in front of and behind this pixel or in the left and right of this pixel are used for the sum signals $W_a$ and $W_b$. In this case, according to the resolution of the two-dimensional sensors, the sample object, and the like, appropriate pixels are selected as the pixels in front of and behind or in the left and right of the certain pixel.

Thus determined phase difference $\Psi$ can be input into expression (17) to calculate the level difference $\Delta h$. Accordingly, in this embodiment, any level difference can be measured with a high accuracy even when the light reflectivity changes between both sides of the level difference.

Twelfth Embodiment

Figure 15:
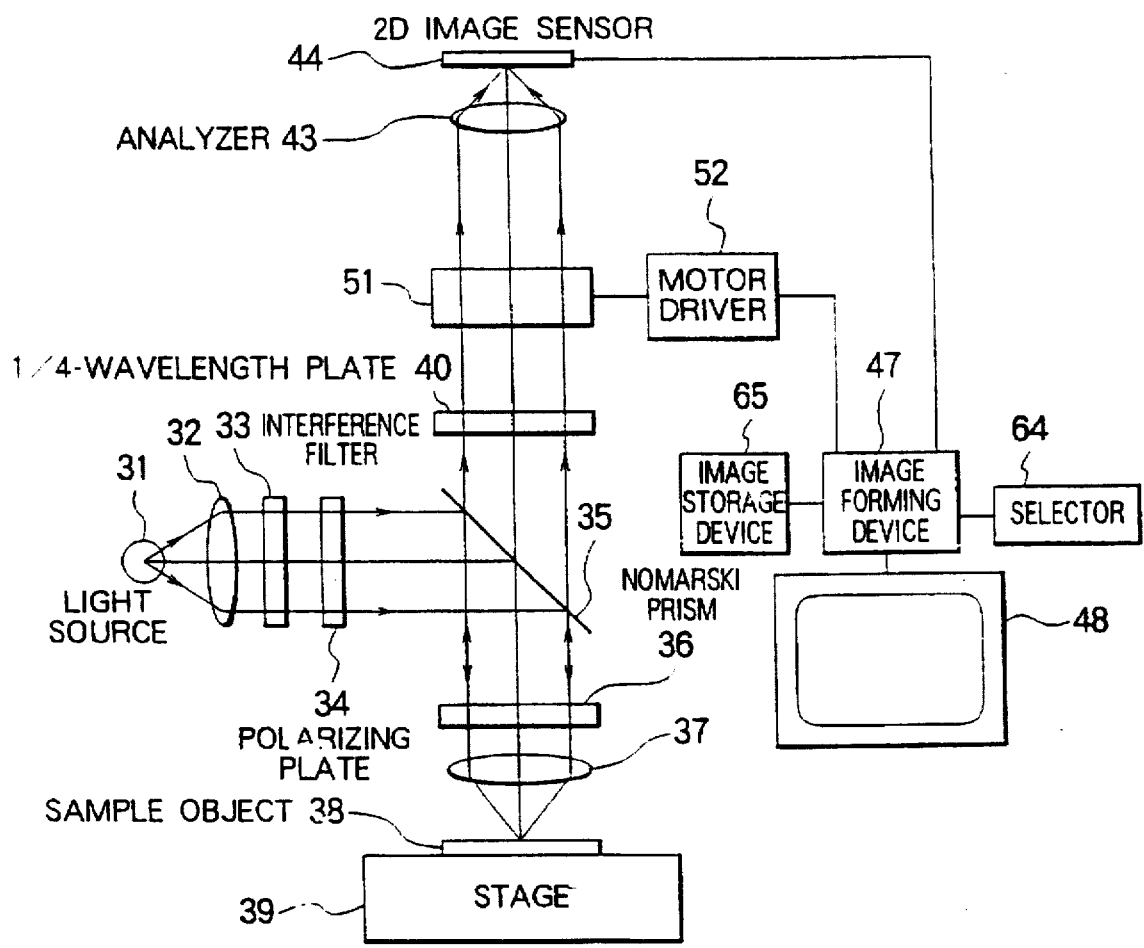
FIG. 15 is a block diagram schematically showing a configuration of a level-difference measuring apparatus as a twelfth embodiment in accordance with the observation apparatus of the present invention.

As shown in FIG. 15, the level-difference measuring apparatus of this embodiment uses the light source, illumination optical system, and the like which are similar to those of the eleventh embodiment.

The light emitted from the light source 31, which is a tungsten lamp, is turned into parallel light as being transmitted through the collimator lens 32. Then, as it is transmitted through the interference filter 33, a wavelength thereof is selected. In this embodiment, the selected wavelength is 550 nm. The light transmitted through the interference filter 33 is turned into linearly polarized light by way of the polarizing plate 34 and then made incident on the half mirror 35. The polarization direction at this time is in parallel to the paper surface of FIG. 15.

The light reflected by the half mirror 35 in a downward direction in the drawing is made incident on the Nomarski prism 36. The Nomarski prism 36 is a birefringence prism which has an optic axis intersecting the polarization direction of the incident laser beam at 45° and splits the incident light into two light components according to their polarization characteristics.

The two light components split by the Nomarski prism 36 are converged by way of the objective lens 37 so as to form two illumination light components on the sample object 38 mounted on the stage 39. Thus, due to the operation of the Nomarski prism 36, two illumination light components slightly distanced from each other at their centers are formed on the sample object 38. The two reflected light components from the sample object 38 with respect to the two illumination light components are transmitted through the objective lens 37 again and then combined together by way of the Nomarski prism 36.

Here, the inserting position of the Nomarski prism 36 with respect to the optical axis of the objective lens 37 is defined such that the Nomarski prism 36 imparts a phase difference of $\pi$ multiplied by an integer to the two illumination light components as they travel therethrough to-and-fro. Accordingly, when the sample object 38 is of a flat surface having no level difference, i.e., a mirror surface, the phase difference between the two reflected light components by way of the Nomarski prism 36 becomes $\pi$ multiplied by an integer. In other words, the two reflected light components from the object 38 with respect to the two illumination light components are combined together, by way of the Nomarski prism 38, into linearly polarized light having a polarization direction in parallel to or perpendicular to the paper surface of FIG. 15. The composite light formed by way of the Nomarski prism 36 is made incident on the half mirror 35.

The composite light transmitted through the half mirror 35 is made incident on the ¼-wavelength plate 40. The ¼-wavelength plate 40 is positioned so as to have an azimuth of $\pi/4$ with respect to the linear polarization direction of the composite linearly polarized light which is incident on the ¼-wavelength plate 40 when the sample object 38 is of a mirror surface. Accordingly, when the sample object 38 is of a mirror surface, the composite light emitted from the ¼-wavelength plate 40 becomes circularly polarized light and then is made incident on the analyzer 51. The analyzer 51 is constituted by a polarizing plate which is rotatable around the optical axis of the objective lens 37 and a motor which rotates the polarizing plate based on an analyzer angle signal output from the motor driver 52. Here, the motor driver 52 supplies the analyzer angle of the analyzer 51, as an electric signal, to the image forming device 47.

By way of the imaging lens 43, the light transmitted through the analyzer 51 forms an image on the two-dimensional image sensor 44 and is photoelectrically converted thereby. The signal photoelectrically converted by the two-dimensional image sensor 44 is supplied to the image forming device 47.

Based on the analyzer angle signal from the motor driver 52, at an analyzer angle of $\pi/4$ (which is defined as $\phi1$), the image forming device 47 captures the electric signal photoelectrically converted by the two-dimensional image sensor 44 and stores it in the image storage device 65. Then, when the analyzer angle becomes $\phi1+m\pi/2$ (m being an odd number), it captures the electric signal photoelectrically converted by the two-dimensional image sensor 44 again and calculates, for each pixel, the difference signal S between thus captured signal and the image at the analyzer angle of $\phi1$ stored in the image storage device 65 as well as their sum signal W.

Further, according to an instruction from the selector 64, the image forming device 47 supplies an image data based on the difference signal S or sum signal W to the display device 48 together with the measured value of the level difference. Namely, the image forming device 47 supplies a differential interference image when the difference signal S is selected by the selector 64, whereas it supplies a bright field image when the sum signal W is selected by the selector 64.

Thus, the display device 48 displays, together with the measured value of the level difference, a differential interference image or bright field image in response to the switching of the selector 64. In this case, the profiles of the difference signal S and sum signal W are superposed on the displayed differential interference image and bright field image, respectively. Subsequently, as in the case of the above-mentioned eleventh embodiment in accordance with the present invention, the level difference $\Delta h$ can be calculated.

Thirteenth Embodiment

Figure 16:
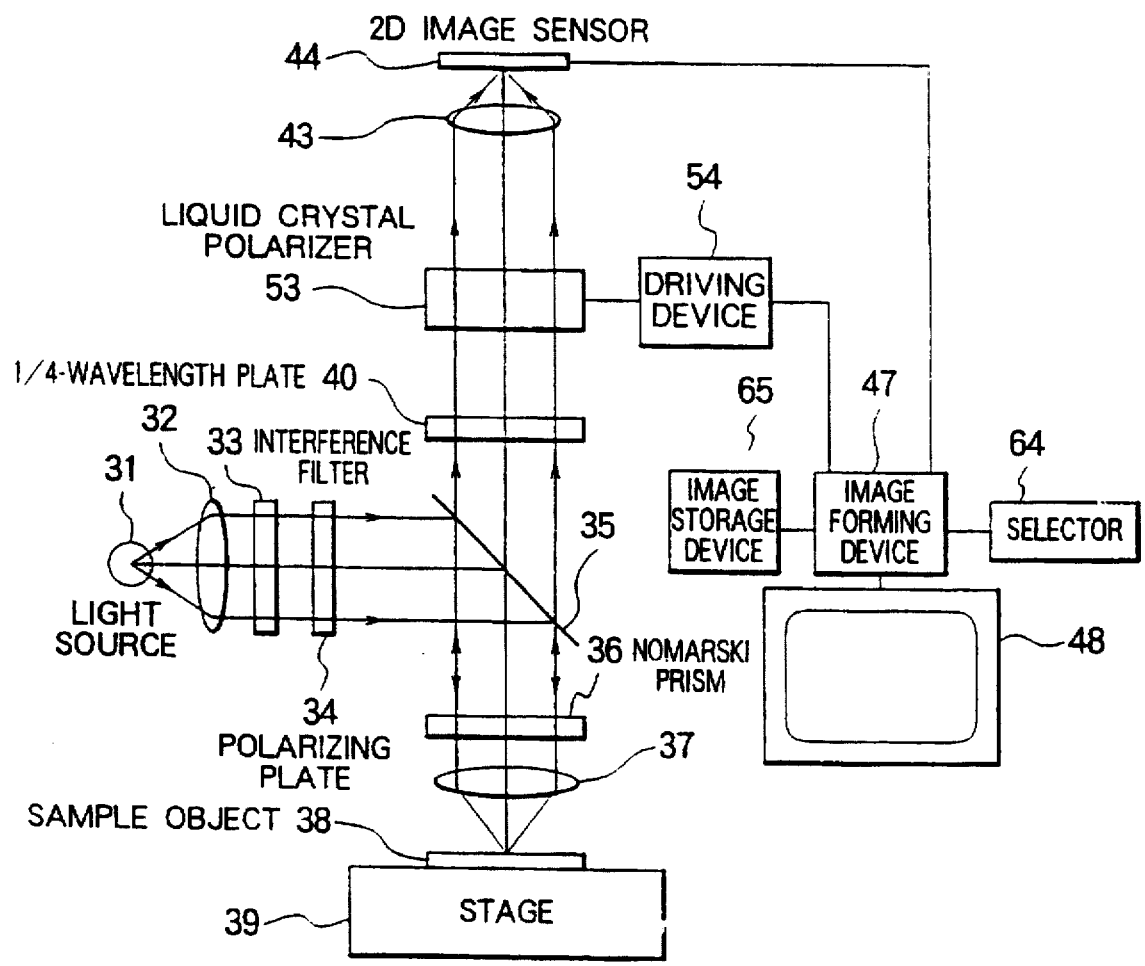
FIG. 16 is a block diagram schematically showing a configuration of a level-difference measuring apparatus as a thirteenth embodiment in accordance with the observation apparatus of the present invention.

As shown in FIG. 16, the level-difference measuring apparatus of this embodiment has mostly the same configuration as that of the level-difference measuring apparatus of the twelfth embodiment. Accordingly, in FIG. 16, the constituents identical to those of the twelfth embodiment are referred to with the marks identical thereto without repeating their overlapping explanations. Here, only the points different from the twelfth embodiment will be explained.

In this embodiment, in place of the polarizing plate in the twelfth embodiment which is rotated by a motor, the liquid crystal polarizer 53 is used. The liquid crystal polarizer 53 functions as a polarizing plate whose polarization direction can be arbitrarily changed when the voltage applied thereto from the driving device 54 is arbitrarily changed, namely, as an analyzer whose analyzer angle can be arbitrarily set. The driving device 54 supplies the analyzer angle, as an electric signal, to the image forming device 47.

By way of the imaging lens 43, the light transmitted through the liquid crystal polarizer 53 forms an image on the two-dimensional image sensor 44 and is photoelectrically converted thereby. The signal photoelectrically converted by the two-dimensional image sensor 44 is supplied to the image forming device 47.

Based on the analyzer angle signal from the driving device 54, at an analyzer angle of $\pi/4$ (which is defined as $\phi1$), the image forming device 47 captures the electric signal photoelectrically converted by the two-dimensional image sensor 44 and stores it in the image storage device 65. Then, when the analyzer angle becomes $\phi1+m\pi/2$ (m being an odd number), it captures the electric signal photoelectrically converted by the two-dimensional image sensor 44 again and calculates, for each pixel, the difference signal S between thus captured signal and the image at the analyzer angle of φ1 stored in the image storage device 65 as well as their sum signal W. Subsequently, as in the case of the above-mentioned twelfth embodiment in accordance with the present invention, the level difference Δh can be calculated.

Fourteenth Embodiment

Figure 17:
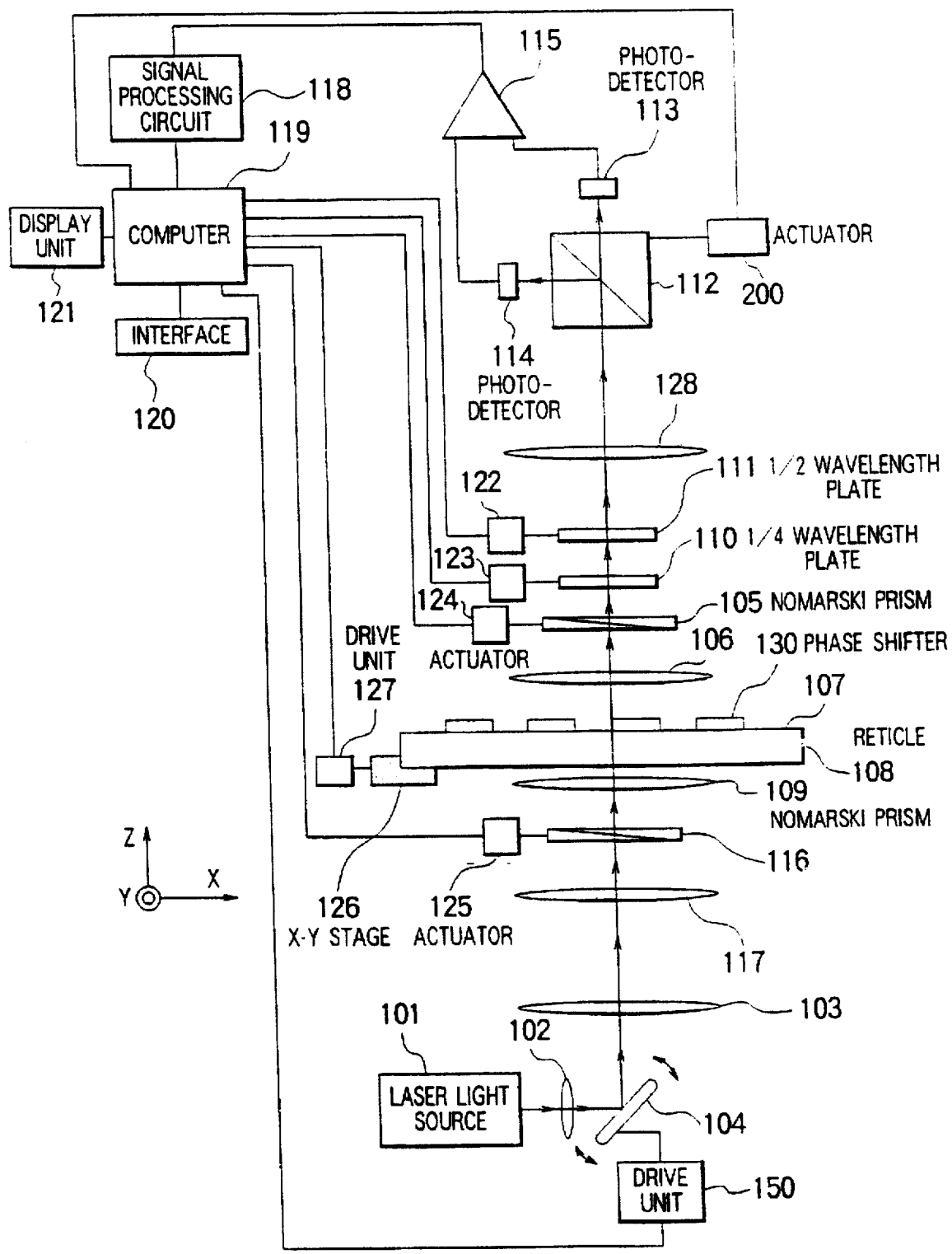
FIG. 17 is a block diagram schematically showing a configuration of a defect inspection apparatus as a fourteenth embodiment in accordance with the observation apparatus of the present invention.

As shown FIG. 17, in the defect inspection apparatus according to the fourteenth embodiment of the present invention, a predetermined circuit pattern is drawn with a phase shifter portion 130 on the transparent quartz portion (glass portion) of a reticle 108 to be inspected. The phase shifter portion is a phase shift member for controlling the transmittance and phase for, e.g., an $SiO_2$ or halftone reticle.

A laser light source 101 emits a monochromatic light beam (inspection light beam) having a wavelength for which the amount of phase shift caused by the phase shifter portion 130 of the reticle 108 to be inspected substantially becomes π. When the phase shifter portion 130 is for the i-line (wavelength: 365 nm) of a mercury lamp, the wavelength of a light beam (inspection light beam) from the laser light source 101 can be close to 365 nm (e.g., 365 nm ±50 nm).

When the wavelength of a laser beam is set at a wavelength for which the amount of phase shift caused by the phase shifter portion 130 is substantially π, both a defect in phase shifter and a foreign substance (phase object) on the reticle can be detected. When only the phase shifter is to be inspected, the inspection light beam can be set at any wavelength.

The linearly polarized laser beam emitted from the laser light source 101 is collimated by a collimator lens 102 into a parallel beam and incident on a vibration mirror 104. The vibration mirror 104 can deflect the laser beam by a driving section 150. The polarization direction of the laser beam is parallel to the paper surface, and the vibration mirror 104 deflects the laser beam in a one-dimensional direction. The driving section 150 is controlled by a computer 119.

The laser beam reflected by the vibration mirror 104 is refracted by a first relay lens 103 and a second relay lens 117, transmitted through a Nomarski prism 116, separated into linearly polarized light beams having polarization directions perpendicular to each other at a slight relative angle. The light beams are refracted by a condenser lens 109 and incident on the reticle 108 mounted on an X-Y stage 126. The Nomarski prism 116 is arranged at the pupil position of the condenser lens 109 or at a position near the conjugate position of the condenser lens 109.

These light beams form beam spots in a circuit drawn surface 107 of the reticle 108. Two beam spots slightly shifted from each other are formed by the function of the Nomarski prism 116. The two light beams forming the two beam spots are two linearly polarized light beams having polarization directions perpendicular to each other. The two spots one-dimensionally scan the circuit drawn surface 107 in the X direction by the function of the vibration mirror 104. Simultaneously, the X-Y stage 126 moves the reticle 108 along the Y direction at a constant velocity. These spots perform X-Y raster scanning in the circuit drawn surface 107, thereby performing defect inspection in an area having a predetermined size.

The X-direction length of this shot area is regulated by the optical system, though the length along the Y direction is not regulated. Therefore, a rectangular area with its long sides extending along the Y direction can be set. When an area larger than this shot area (an area larger than the area having the predetermined size) is to be inspected, stage movement along the Y direction at the constant velocity and the step operation along the X direction by the X-Y stage 126 can be alternately performed a plurality of times such that a plurality of the shot areas overlap along the X direction.

The X-Y stage 126 is driven by a driving section 127 constituted by a motor and the like. The computer 119 controls the driving section 127. The Nomarski prism 116 can be moved in a direction crossing the optical axis of the condenser lens 109 (e.g., a direction almost perpendicular to the optical axis) by an actuator 125 constituted by a piezoelectric device and the like. The computer 119 controls the actuator 125.

The two linearly polarized laser beams transmitted through the reticle 108 and having polarization directions perpendicular to each other are refracted by an objective lens 106 and reach a Nomarski prism 105 as two light beams having polarization directions perpendicular to each other at a slight relative angle. These two light beams are parallel beams of light. These parallel beams of light are converted into one parallel beam of light by the function of the Nomarski prism 105, and the parallel beam of light reaches a ¼-wavelength plate 110.

The Nomarski prism 105 can also be moved in a direction crossing the optical axis of the condenser lens 109 (the optical axis of the objective lens 106), e.g., a direction almost perpendicular to the optical axis by an actuator 124 constituted by a piezoelectric device and the like. The computer 119 controls the actuator 124. The polarized state of the parallel beam of light immediately before the ¼-wavelength plate 110 can be changed from the circularly polarized state to the linearly polarized state by adjusting the inserting positions of the two Nomarski prisms 105 and 116.

Here, the inserting positions of the two Nomarski prisms 105 and 116 are adjusted such that the parallel beam of light immediately before the ¼-wavelength plate 110 is in a linearly polarized state for a flat glass portion of the circuit drawn surface 107 of the reticle 108, where no level difference such as a circuit pattern is present. At this time, adjustment is performed such that the two linearly polarized laser beams having polarization directions perpendicular to each other have a relative phase difference of π multiplied by an integer. The inserting azimuths of the two Nomarski prisms 105 and 116 are set such that the azimuths of wedge portions of the two prisms coincide each other, and the shear direction of the two linearly polarized laser beams is set to have an azimuth of π/4 with respect to the paper surface.

The ¼-wavelength plate 110 is inserted to have an azimuth of π/4 with respect to the linear polarization direction of the immediately preceding parallel beam of light, i.e., the direction parallel or perpendicular to the paper surface. Therefore, for the flat glass portion of the circuit drawn surface 107 of the reticle 108, where no level difference such as a circuit pattern is present, the laser beam transmitted through the ¼-wavelength plate 110 is in a circularly polarized state. This laser beam is transmitted through a ½-wavelength plate 111 arranged to freely rotate about the optical axis of the objective lens 106, refracted by a collector lens 128, and polarized and separated by a polarizing beam splitter 112 serving as an analyzer.

A linearly polarized light component parallel to the paper surface is photoelectrically converted by a photodetector 113 while a linearly polarized light component perpendicular to the paper surface is photoelectrically converted by a photodetector 114. The two photodetectors 113, 114 is constituted by a photomultiplier, an SPD (Silicon Photo Diode), or the like. The two photodetectors 113, 114 can be arranged at any position after the synthesizing optical system. For example, the two photodetector 113, 114 can be arranged on the pupil conjugate surface of the objective lens 106 or on the image conjugate surface of the reticle 108.

The ¼-wavelength plate 110 is rotated about the optical axis of the objective lens 106 by an actuator 123 constituted by a piezoelectric device and the like and set to have the above-described azimuth. The ½-wavelength plate 111 can be rotated about the optical axis of the objective lens 106 by an actuator 122 constituted by a piezoelectric device and the like. The two actuators 122, 123 is controlled by the computer 119.

The rotational angle of the ½-wavelength plate 111 corresponds to a value twice the analyzer angle φ described above in the section "Principle". The azimuth of the ½-wavelength plate 111 is set such that the analyzer angle φ of the analyzer (polarizing beam splitter 112) substantially becomes π/4. More specifically, the actuator 122 sets the ½-wavelength plate 111 such that the analyzer angle φ substantially becomes π/4.

Prior to actual inspection, the actuator 122 finely adjusts the azimuth of the ½-wavelength plate 111 by using the nondefective phase shifter portion of the reticle to be inspected such that the difference between electrical signals from the two photodetectors 113 and 114, which are adjusted to have the same gain, is minimized. With this adjustment, the analyzer angle φ of the analyzer is set to be π/4 (in other words, the sensitivity for detecting foreign substances is maximized). At the same time, the gains of outputs from the two photodetectors 113 and 114 are finely adjusted to minimize the influence of an error remaining in the optical system. With the fixed polarizing beam splitter 112 and rotatable ½-wavelength plate 111, the analyzer capable of changing the analyzer angle can be constituted.

With the above setup operation, in actual inspection, only when a defect in shift amount of the phase shifter portion in the circuit drawn surface 107 of the reticle 108, or a foreign substance as a phase object adhering to the transparent portion (glass portion) of the reticle 108 is present, a difference is generated between electrical signals from the two photodetectors 113 and 114. When no defect is present, no difference is generated between the two electrical signals.

The electrical signals photoelectrically converted by the two photodetectors 113 and 114 become a differential signal in a differential amplifier 115 and input to a signal processing circuit 118 having a window comparator circuit. The window comparator circuit is a binary circuit having two slice levels on the positive and negative sides. The signal processing circuit 118 outputs a binary signal value or a differential signal value to the computer 119. The computer 119 detects the presence/absence of a defect on the basis of this binary signal. The two slice levels on the positive and negative sides of the window comparator circuit of the signal processing circuit 118 are set not to produce any pseudo defect due to optical or electrical noise. The computer 119 can also receive output values from the two photodetectors 113 and 114 without any processing.

The computer 119 performs synchronous control of the vibration mirror 104 and the X-Y stage 126 when defect inspection is being executed. As described above, the computer 119 controls the four actuators 122 to 125. The computer 119 can also finely adjust the four optical elements 105, 110, 111, and 116 and automatically perform the setup operation before inspection. The computer 119 stores the differential signal or the output values from the two photodetectors 113 and 114 in synchronism with the position information of the vibration mirror 104 or the X-Y stage 126 (e.g., a control signal).

The computer 119 generates the map of a signal representing the defect position in the reticle and the size of the foreign substance at the defect position (e.g., the differential signal amount, larger or smaller one of output values from the two photodetectors 113 and 114, the average of the output values from the two photodetectors 113 and 114, or the like) and displays the map on a display section 121 such as a CRT display unit. The foreign substance can be visually observed using a visual system (not shown) on the basis of this map to discriminate a defect in phase shifter from a foreign substance as a phase object. The operator inputs the inspection sensitivity, the inspection area, execution of initial setting of the apparatus, execution of inspection, and the like to the computer 119 through an interface 120 such as a keyboard.

Fifteenth Embodiment

Figure 18:
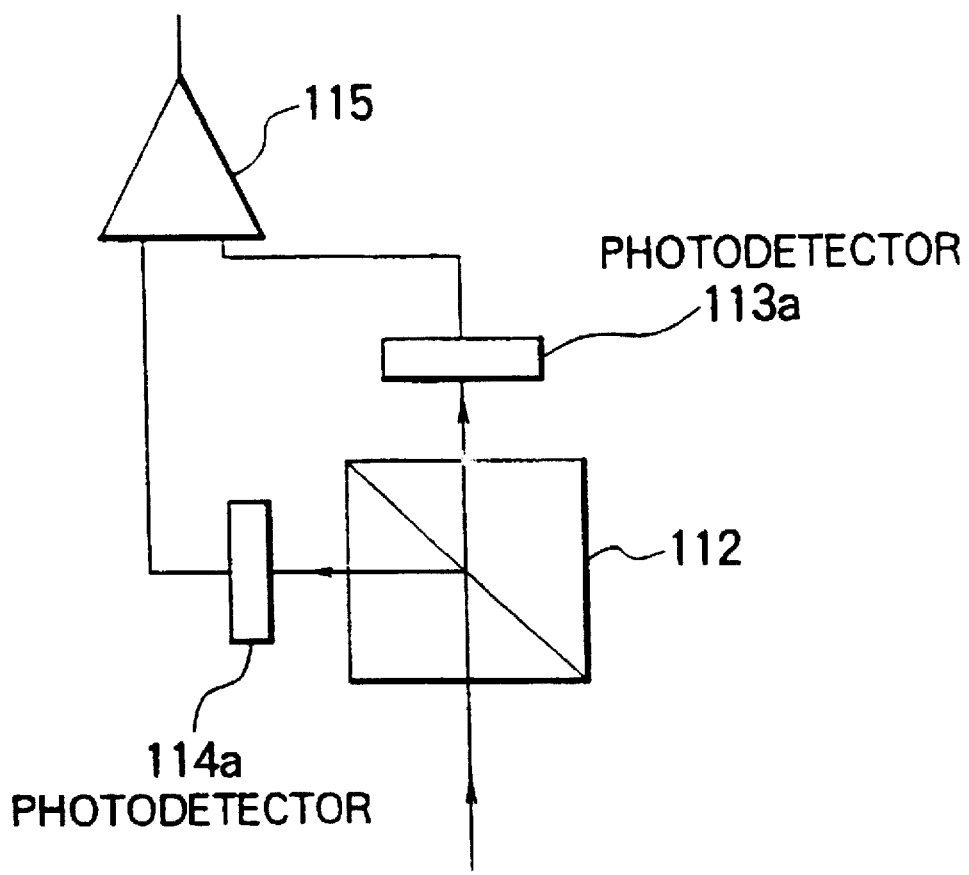
FIG. 18 is a block diagram schematically showing a configuration of a defect inspection apparatus as a fifteenth embodiment in accordance with the observation apparatus of the present invention.

As shown FIG. 18, the defect inspection apparatus according to the fifteenth embodiment of the present invention differs from the fourteenth embodiment mainly in the two photodetectors 113 and 114. In the fourteenth embodiment, a sensor constituted by only one element is used as the two photodetector 113 and 114. In this embodiment, a one-dimensional linear sensor constituted by multiple elements is used as two photodetector 113a and 114a. In FIG. 18, other constituent elements are the same as those in FIG. 17 and will not be illustrated.

The two photodetectors 113a and 114a are one-dimensional linear sensors each constituted by multiple elements. For this reason, the photodetectors 113a and 114a are arranged on planes conjugate to a circuit drawn surface 107 of a reticle 108 to be inspected. The direction of alignment of the plurality of photodetection elements of the photodetectors 113a and 114a coincides with the moving direction of the image of a beam spot on the circuit drawn surface 107, which image is moved in accordance with one-dimensional scanning of the beam spot by a vibration mirror 104.

In this embodiment, positioning between the two one-dimensional linear sensors is particularly important. If an error in positioning remains, a pseudo defect in a size equal to the error is generated at the level difference portion of the pattern drawn surface. When positioning cannot be completely mechanically performed, an image processing circuit is arranged in a signal processing circuit 118 to electrically perform positioning using a known image processing technique.

Sixteenth Embodiment

Figure 19:
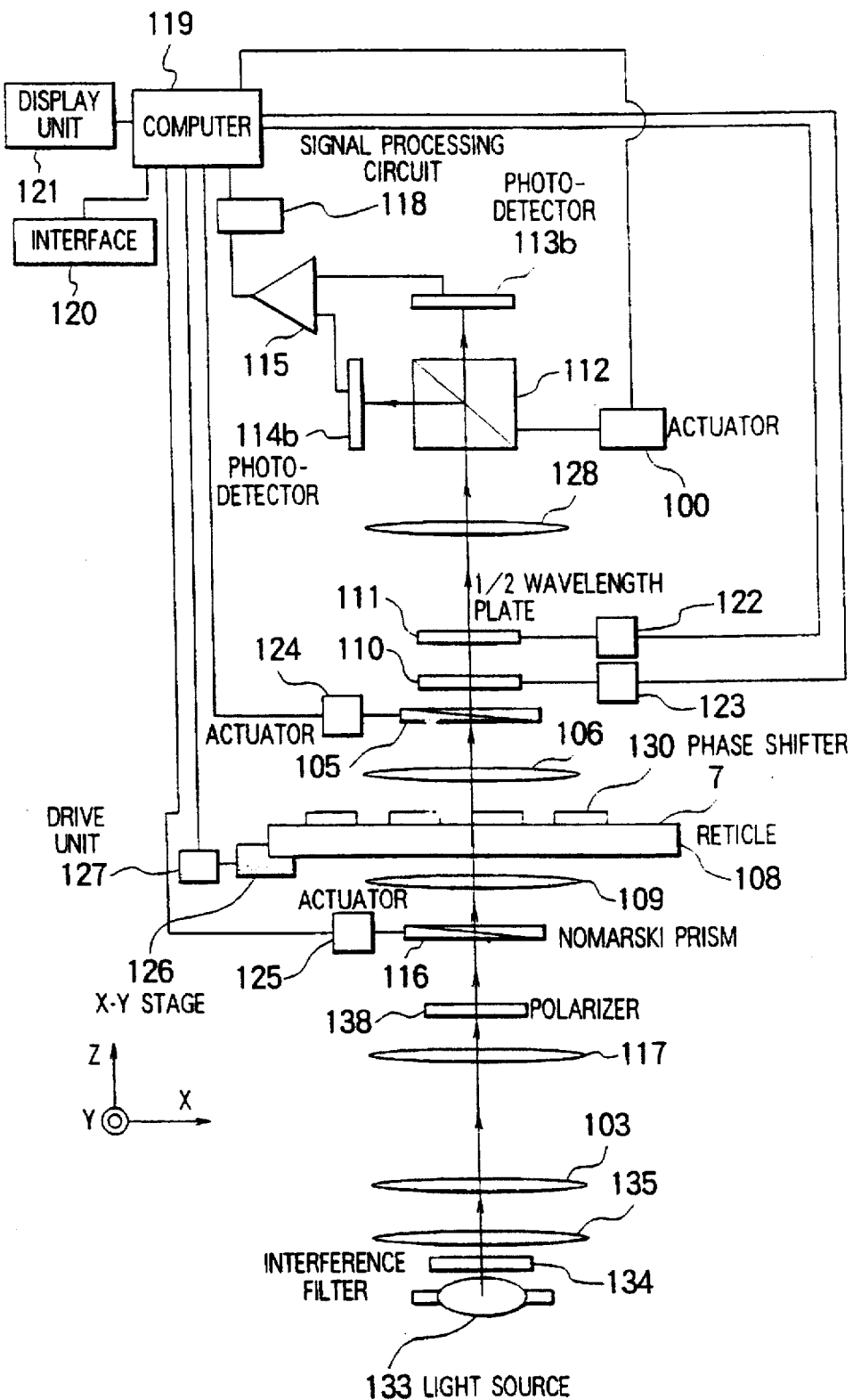
FIG. 19 is a block diagram schematically showing a configuration of a defect inspection apparatus as a sixteenth embodiment in accordance with the observation apparatus of the present invention.

As shown FIG. 19, the defect inspection apparatus according to the sixteenth embodiment of the present invention differs from the fourteenth and fifteenth embodiments mainly in the illumination method. Both the above two embodiments are based on the optical system of a differential interference microscope having a laser scanning type illumination optical system. However, this embodiment is based on an imaging type differential interference microscope. The same reference numerals as in FIG. 17 denote the same members in FIG. 19, and a detailed description thereof will be omitted.

A light source 133 is a mercury lamp. For an emitted light beam, an optimum wavelength is selected by an interference filter 134. When the phase shifter of a reticle 108 to be inspected is for the i-line, a wavelength of 365 nm is selected. More specifically, the interference filter 134 outputs a monochromatic light beam having a wavelength for which the amount of phase shift of a phase shifter portion 130 substantially becomes π. The light beam transmitted through the interference filter 134 is transmitted through a collector lens 135, a first relay lens 103, and a second relay lens 117, and converted by a polarizer 138 into a linearly polarized light beam having a plane of polarization parallel to the paper surface.

This linearly polarized light beam is separated into two linearly polarized light beams having planes of polarization perpendicular to each other through a Nomarski prism 116. The light beams are refracted by a condenser lens 109. The two linearly polarized light beams illuminate the field of an objective lens 106 on the reticle 108. The linearly polarized light beams having planes of polarization perpendicular to each other are transmitted through the objective lens 106 and combined into one light beam again through a Nomarski prism 105.

The inserting positions of the two Nomarski prisms are adjusted such that a phase difference of π multiplied by an integer is imparted between the two Nomarski prisms when no phase modulation caused by an object is present. The inserting azimuths of the two Nomarski prisms 116 and 105 are set to make the azimuths of the wedge portions of the two prisms match each other and have an azimuth of π/4 with respect to the paper surface. At this time, when no phase modulation caused by an object is present, the light beam emerging from the Nomarski prism 105 becomes a linearly polarized light beam having a plane of polarization parallel or perpendicular to the paper surface.

A ¼-wavelength plate 110 is inserted to have an azimuth of π/4 with respect to the linear polarization direction of the light beam immediately before, i.e., the direction parallel or perpendicular to the paper surface. Therefore, the light beam transmitted through a flat glass portion where no level difference such as a circuit pattern on a circuit drawn surface 107 of the reticle 108 is present is transmitted through the ¼-wavelength plate 110 to be in a circularly polarized light beam. The circularly polarized light beam is transmitted through a ½-wavelength plate 111 arranged to freely rotate about the optical axis of the objective lens 106, refracted by a collector lens 128, and polarized and separated by a polarizing beam splitter 112 serving as an analyzer. A linearly polarized light component parallel to the paper surface is photoelectrically converted by a photodetector 113b while a linearly polarized light component perpendicular to the paper surface is photoelectrically converted by a photodetector 114b.

The two photodetectors 113b and 114b are two-dimensional image pickup devices each constituted by multiple elements. For this reason, the photodetectors 1013b and 1014b are arranged on planes conjugate to the circuit drawn surface 107 of the reticle 108 to be inspected. The position of a foreign substance is detected in accordance with the positions of the respective elements of the two-dimensional imaging devices.

In this embodiment, positioning between the two two-dimensional linear sensors is particularly important. If an error in positioning remains, a pseudo defect in a size equal to the error is generated at the level difference portion 107 of the pattern drawn surface. When perfect positioning cannot be mechanically performed, an image processing circuit is arranged in a signal processing section 118 to electrically perform positioning using a known image processing technique.

The rotational angle of the ½-wavelength plate 111 corresponds to a value twice an analyzer angle φ described above in the section "Principle". The azimuth of the ½-wavelength plate 111 is set such that the analyzer angle φ substantially becomes π/4. Prior to actual inspection, the level difference of a nondefective phase shifter portion of the reticle 108 to be inspected is observed, and the azimuth of the ½-wavelength plate 111 is finely adjusted such that the difference between electrical signals from the two photodetectors 113b and 114b, which are adjusted to have the same gain, is minimized.

With the above setup operation, only when a defect in shift amount of the phase shifter portion in the circuit drawn surface 107 of the reticle 108, or a foreign substance as a phase object adhering to the transparent portion (glass portion) of the reticle 108 is present, a difference is generated between electrical signals from the photodetectors 113b and 114b. When no defect is present, no difference is generated between two electrical signals.

The electrical signals photoelectrically converted by the two photodetectors 113b and 114b become a differential signal in a differential amplifier 115 and input to the signal processing circuit 118 having a window comparator circuit. The window comparator circuit is a binary circuit having two slice levels on the positive and negative sides. The signal processing circuit 118 outputs a binary signal value or a differential signal value to a computer 119. The two slice levels on the positive and negative sides of the window comparator circuit of the signal processing circuit 118 are set not to produce any pseudo defect caused by optical or electrical noise.

In this embodiment, the field of the objective lens 106 can be inspected at once. When an area larger than the field of the objective lens 106 in the circuit drawn surface 107 is to be inspected, an X-Y stage 126 is stepped along a direction crossing the optical axis of the microscope, thereby setting the field of the objective lens 106 in a matrix in the inspection area. With this operation, an area in desired size can be inspected.

As in the fourteenth and fifteenth embodiments, the computer 119 moves the X-Y stage 126 through a driving section 127 and controls the four actuators 122 to 125. The computer 119 can also finely adjust the four optical elements 105, 110, 111, and 116 and automatically perform the setup operation before inspection. The computer 119 also generates a map representing the defect position in the reticle and the differential signal amount at the defect position and displays the map on a display section 121.

Seventeenth Embodiment

Figure 20:
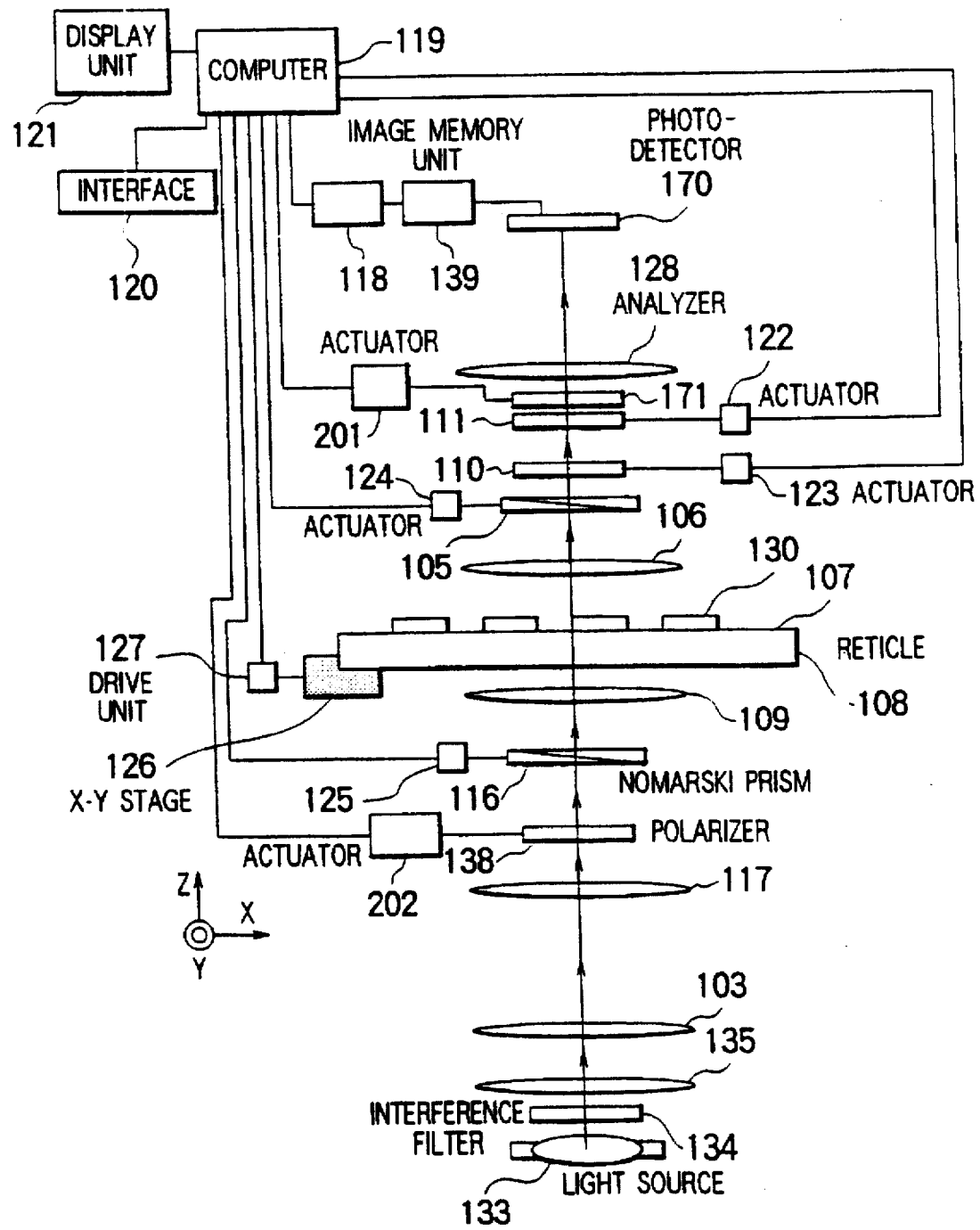
FIG. 20 is a block diagram schematically showing a configuration of a defect inspection apparatus as a seventeenth embodiment in accordance with the observation apparatus of the present invention.

As shown FIG. 20, the defect inspection apparatus according to the seventeenth embodiment of the present invention differs from the sixteenth embodiment mainly in a method of receiving an image. In the sixteenth embodiment, the linearly polarized light component parallel to the paper surface and the linear polarized light component perpendicular to the paper surface are polarized and separated by the polarizing beam splitter 112 and photoelectrically converted by the two photodetectors 113b and 114b, respectively. Therefore, a difference image can be generated in real time. In the this embodiment, one photodetector 170 (a photodetector commonly used as the photodetectors 113b and 114b) and an analyzer 171 for transmitting a linearly polarized light component having a plane of polarization parallel to the paper surface are used. With this arrangement, the image of the linearly polarized light component parallel to the paper surface and the image of the linearly polarized light component perpendicular to the paper surface are received at different times.

An image corresponding to the image of the linearly polarized light component parallel to the paper surface in the fourteenth and fifteenth embodiments is received through a ½-wavelength plate 111 which is set such that an analyzer angle φ becomes π/4 (or the analyzer angle φ determined by expression (22) is set). Subsequently, an image corresponding to the image of the linearly polarized light component perpendicular to the paper surface in the fourteenth and fifteenth embodiments is received through the ½-wavelength plate 111 which is set such that the analyzer angle φ becomes 3π/4 (or an angle obtained by adding 90° (π/2) to the analyzer angle φ determined by expression (22) is set). As a result, two images corresponding to an object on one field of an objective lens 106 can be obtained.

These images are temporarily independently stored in an image memory section 139 as two image data. Thereafter, the difference image between the two images is calculated in the image memory section 139 and input to a signal processing section 118 as a difference image signal. Alternatively, the analyzer 171 controlled by the computer 119 may be directly driven by an actuator 201 to set the analyzer angle φ to be π/4 and 3π/4 or an angle determined by expression (22) and an angle obtained by adding 90° to the angle determined by expression (22), thereby obtaining two images.

The analyzer 171 or the ½-wavelength plate 111 can also be rotated to set the analyzer angle φ to be π/4 or the angle determined by expression (22), and the light beam having a polarization direction perpendicular to the analyzer angle φ can be received while keeping the analyzer 171 or the ½-wavelength plate 111 fixed. At this time, the azimuth of a polarizer 138 is changed by 90° using an actuator 202 controlled by the computer 119, thereby obtaining two images.

More specifically, the azimuth of the polarizer 138 is set parallel to the paper surface first. The analyzer angle φ is set to be the azimuth of the analyzer 171, π/4 or the angle of expression (22) in accordance with the ½-wavelength plate 111. A first image obtained at this time is stored. Subsequently, without changing the analyzer angle φ, the polarizer 138 is set to have an azimuth perpendicular to the paper surface by an actuator 202. This operation is equivalent to 90° rotation of the analyzer angle φ. An image obtained at this time is stored as a second image.

In this embodiment, the angle of the polarizer 138 can be changed by only 90° between the direction parallel to the paper surface and the direction perpendicular to the paper surface for only the purpose of increasing/decreasing the analyzer angle by only 90°. This is important to maintain the amplitude ratio of the two light beams separated by a Nomarski prism 116 at 1:1.

In this embodiment as well, the signal processing circuit 118 having a window comparator circuit serving as a binary circuit having two slice levels on the positive and negative sides outputs a binary signal value or a differential signal value to a computer 119. The two slice levels on the positive and negative sides of the window comparator circuit of the signal processing circuit 118 are set not to produce any pseudo defect even in the presence of optical or electrical noise.

The computer 119 generates the map of a signal representing the defect position in the reticle and the size of the foreign substance at the defect position and displays the map on a display section 121. The computer 119 performs control of the azimuth of the π/2-wavelength plate 111, control of an X-Y stage 126, and control of the image storage section 139 while defect inspection is being executed. The computer 119 controls the four actuators 1022 to 1025. The computer 119 can also finely adjust the four optical elements 105, 110, 111, and 116 and automatically perform the setup operation before inspection.

In this embodiment, prior to actual inspection, the azimuth of the ½-wavelength plate 111 is finely adjusted to determine two azimuths in correspondence with images to be received such that the difference image signal calculated on the basis of the two image data as the image of the level difference at the same position of the nondefective phase shifter portion of the reticle to be inspected is minimized. The operator inputs the inspection sensitivity, the inspection area, execution of initial setting of the apparatus, execution of inspection, and the like to the computer 119 through an interface 120.

Eighteenth Embodiment

Figure 21:
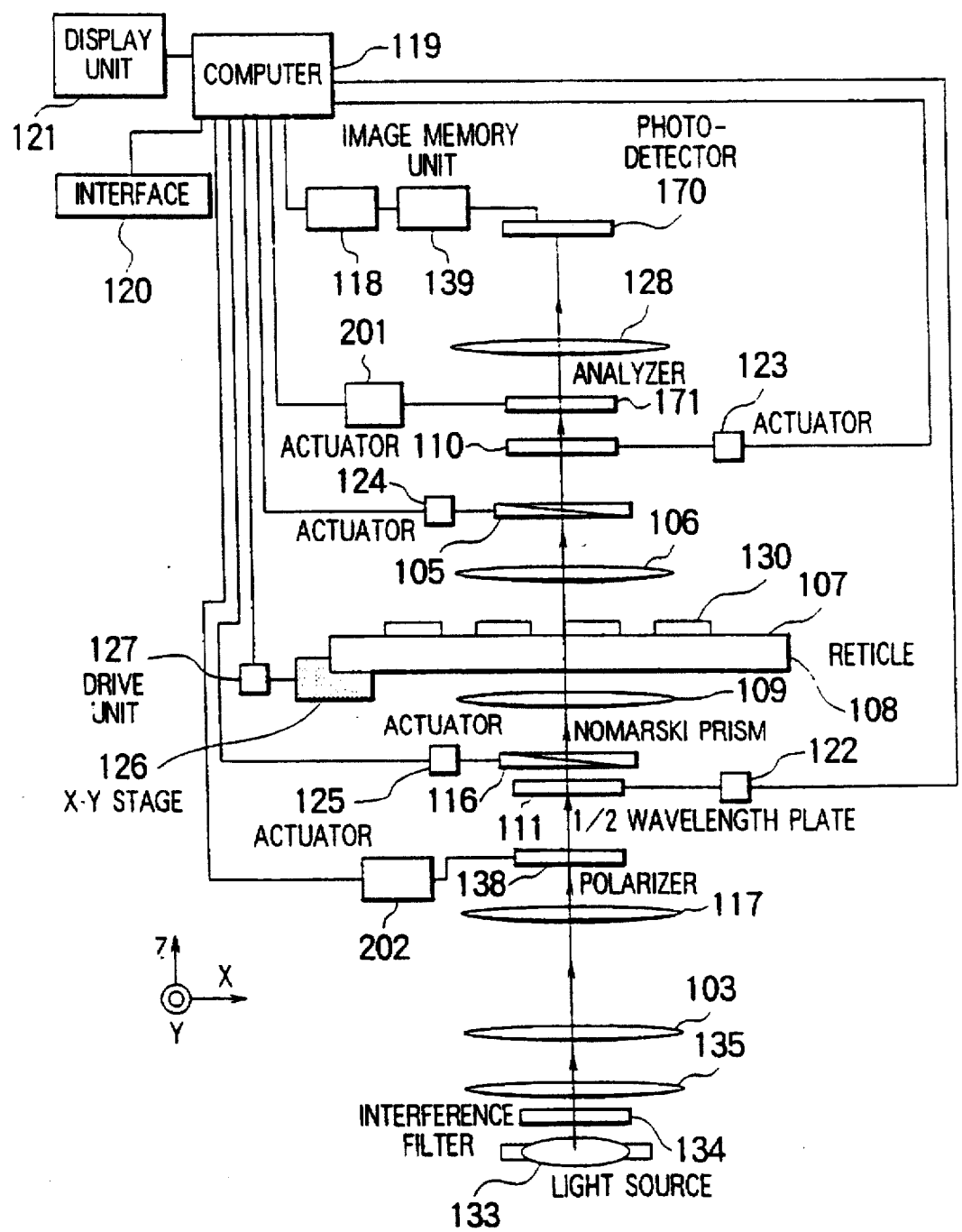
FIG. 21 is a block diagram schematically showing a configuration of a defect inspection apparatus as an eighteenth embodiment in accordance with the observation apparatus of the present invention.

As shown FIG. 21, the defect inspection apparatus according to the eighteenth embodiment of the present invention differs from the seventeenth embodiment only in the setting position of a π/2-wavelength plate 111. In the fourteenth to seventeenth embodiments, the π/2-wavelength plate 111 is arranged between the objective lens 106 and the photodetector (image pickup device). In the this embodiment, the π/2-wavelength plate 111 is arranged between a condenser lens 109 and a light source 133.

In this embodiment, an analyzer angle φ is set to be π/4 or the angle of expression (2) using an analyzer 171 set by an actuator 111. The azimuth of a polarizer 138 and the azimuth of the optic axis of the ½-wavelength plate 111 are set parallel to the paper surface, thereby obtaining a first image. Subsequently, the azimuth of the optic axis of the ½-wavelength plate 111 is set to be 45° with respect to the paper surface, thereby obtaining a second image. That is, instead of rotating the polarizer 138, the ½-wavelength plate 111 is rotated. Since the ½-wavelength plate 111 is positioned between a reticle 108 and the light source 133, no image shift occurs.

This embodiments can be applied to an optical microscope as the above-mentioned seventeenth embodiment. In this case, the light beam from the light source can be white light. When white light is to be used, it is preferable to use neither ½-wavelength plate 111 nor ¼-wavelength plate 110. This embodiment can also be easily applied to an incident-light illumination type optical microscope.

Nineteenth Embodiment

Figure 22:
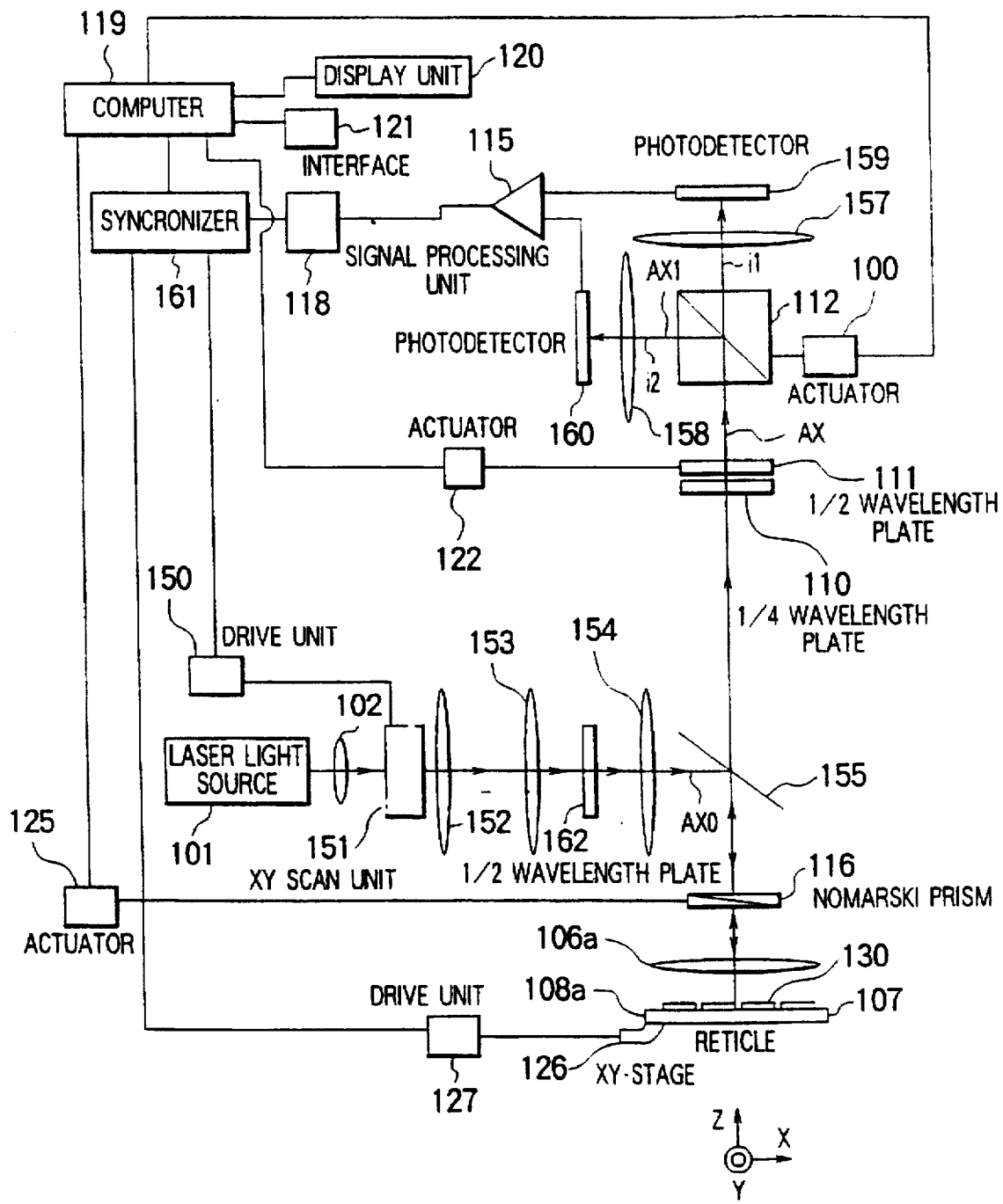
FIG. 22 is a block diagram schematically showing a configuration of a defect inspection apparatus as a nineteenth embodiment in accordance with the observation apparatus of the present invention.

As shown FIG. 22, the defect inspection apparatus according to the eighteenth embodiment of the present invention uses an incident-light illumination method. The same reference numerals as in FIG. 17 denote the same members in FIG. 22, and a detailed description thereof will be omitted.

In this embodiment, a defect inspection using a reflected light beam is performed. The amount of phase shift of the inspection light source, which is caused by a phase shifter, variously changes on the basis of the material of the phase shifter, though the phase shifter is for the i-line, as described above. Therefore, even when the exposure wavelength is used as in the apparatus (transmission type) of the above fourteenth to eighteenth embodiments, the analyzer angle must be determined by expression (22). That is, in this embodiment, the use wavelength is not limited to the exposure wavelength.

A light beam emitted from a laser light source 101 is a linearly polarized light beam having a plane of polarization with an azimuth of 45° with respect to the paper surface. The light beam travels along an optical axis AX0 of an illumination system and is collimated into a parallel beam by a collimator lens 102 and spatially deflected by an X-Y scanning section 151. The X-Y scanning section 151 is constituted by a vibration mirror and the like and one-dimensionally scans the light beam emitted from the laser light source 101 on a reticle 108 in parallel to the paper surface by a driving section 150 such as a motor controlled by the computer 119. The light beam emerging from the driving section 150 is transmitted through a first relay lens 152, a second relay lens 153, and a ½-wavelength plate 162, refracted by a third relay lens 154, reflected by a half mirror 155 along an optical axis AX of an objective lens 109, and separated, through a Nomarski prism 116, into two linearly polarized light beams having polarization directions perpendicular to each other at a slight relative angle.

These two linearly polarized light beams having polarization directions perpendicular to each other at a slight relative angle are refracted by the objective lens 106a to form laser spots on a binary reticle (a reticle having two amplitude transmittances) 108a. The two spots slightly shifted from each other by the function of the Nomarski prism 116 are formed on the binary reticle 108a. These spots one-dimensionally scan the reticle 108a by the function of the X-Y scanning section 151. The ½-wavelength plate 162 finely adjusts the light beam from the laser light source to be accurately 45° with respect to the shear direction of the Nomarski prism 116. The finely adjusted light beam is incident on the Nomarski prism 116.

The light beam reflected by the binary reticle 108a is incident on a condenser lens (objective lens) 106a, refracted by the condenser lens 106a, transmitted through the Nomarski prism 116 positioned near the pupil position of the condenser lens 106a again, transmitted through the half mirror 155, then through a ¼-wavelength plate 110 and a ½-wavelength plate 111, and reaches a polarizing beam splitter 112. The light beam transmitted through the polarizing beam splitter 112 becomes a light beam i1 which is a linearly polarized light beam having an azimuth of 45° with respect to the X-axis about the optical axis AX of the condenser lens 106a. The light beam reflected by the polarizing beam splitter 112 becomes a light beam i2 which is a linearly polarized light beam having an azimuth of 135° with respect to the X-axis about the optical axis AX of the condenser lens 106a.

As for the azimuth of each optical element with respect to the X-axis about the optical axis AX in FIG. 22, assuming that the Y-axis direction is positive, the optic axis of the ¼-wavelength plate 110 is 0°, the direction of wedge of the Nomarski prism 116 is 0°, and an analyzer angle ($\phi$) of the polarizing beam splitter 112 is determined by expression (22). Actually, an actuator 122 rotates the ½-wavelength plate 111 such that the differential output at the level difference of a nondefective shifter of the reticle 108a is minimized.

When no circuit pattern for generating a phase difference between the two beams is present on the binary reticle 108a, the position of the Nomarski prism 116 is adjusted by an actuator 125 controlled by the computer 119 in a direction crossing the optical axis AX such that the initial value of the phase difference imparted to the two light beams (two light beams separated by the Nomarski prism 116) between the Nomarski prism 116 and the reticle 108a becomes $2\pi$ multiplied by an integer, i.e., such that the light beam transmitted through the ¼-wavelength plate 110 becomes a circularly polarized light beam.

The light beam i1 is refracted by a imaging lens 157 and incident on a photoelectric conversion device 159. The photoelectric conversion device 159 photoelectrically converts the light beam i1 to output an image signal. The light beam i2 is refracted by a lens 158 and incident on a photoelectric conversion device 160. The photoelectric conversion device 160 photoelectrically converts the light beam i2 to output an image signal. The two image signals are input to a differential amplifier 115, and the differential amplifier 115 outputs an amplitude differential signal.

This differential signal is input to a signal processing circuit 118 which is a window comparator circuit having two slice levels on the positive and negative sides. The signal processing circuit 118 outputs a binary signal value or a differential signal value to a synchronizer 161. The two slice levels of the signal processing circuit 118 are set as in the fourteenth embodiment. Note that the slice levels can be set from an external device through an interface 120 and the computer 119.

The synchronizer 161 performs synchronous control of the X-Y scanning section 151 and an X-Y stage 126 while inspection is being executed. The X-Y stage 126 is moved by a driving section 127 along a direction almost perpendicular to the direction of one-dimensional scanning by the X-Y scanning section 151. Inspection of a two-dimensional area on the reticle 108a is enabled by the X-Y scanning section 151 and the driving section 127. The computer 119 receives a binary signal, a differential signal, or signals from the two photoelectric conversion devices 159 and 160 in synchronism with the control information for the X-Y stage 126 and the X-Y scanning section from the synchronizer 1061, thereby generating a foreign substance map, as in the fourteenth embodiment, and displaying the map on a display section 121.

The computer 119 controls the actuator 125, thereby finely adjusting the Nomarski prism 1016, and controls the actuator 122, thereby finely adjusting the ½-wavelength plate 111. Thus, the computer 119 automatically performs the setup operation before inspection. The operator inputs the inspection sensitivity, the inspection area, execution of initial setting of the apparatus, execution of inspection, and the like to the computer 119 through the interface 120.

Twentieth Embodiment

Figure 23:
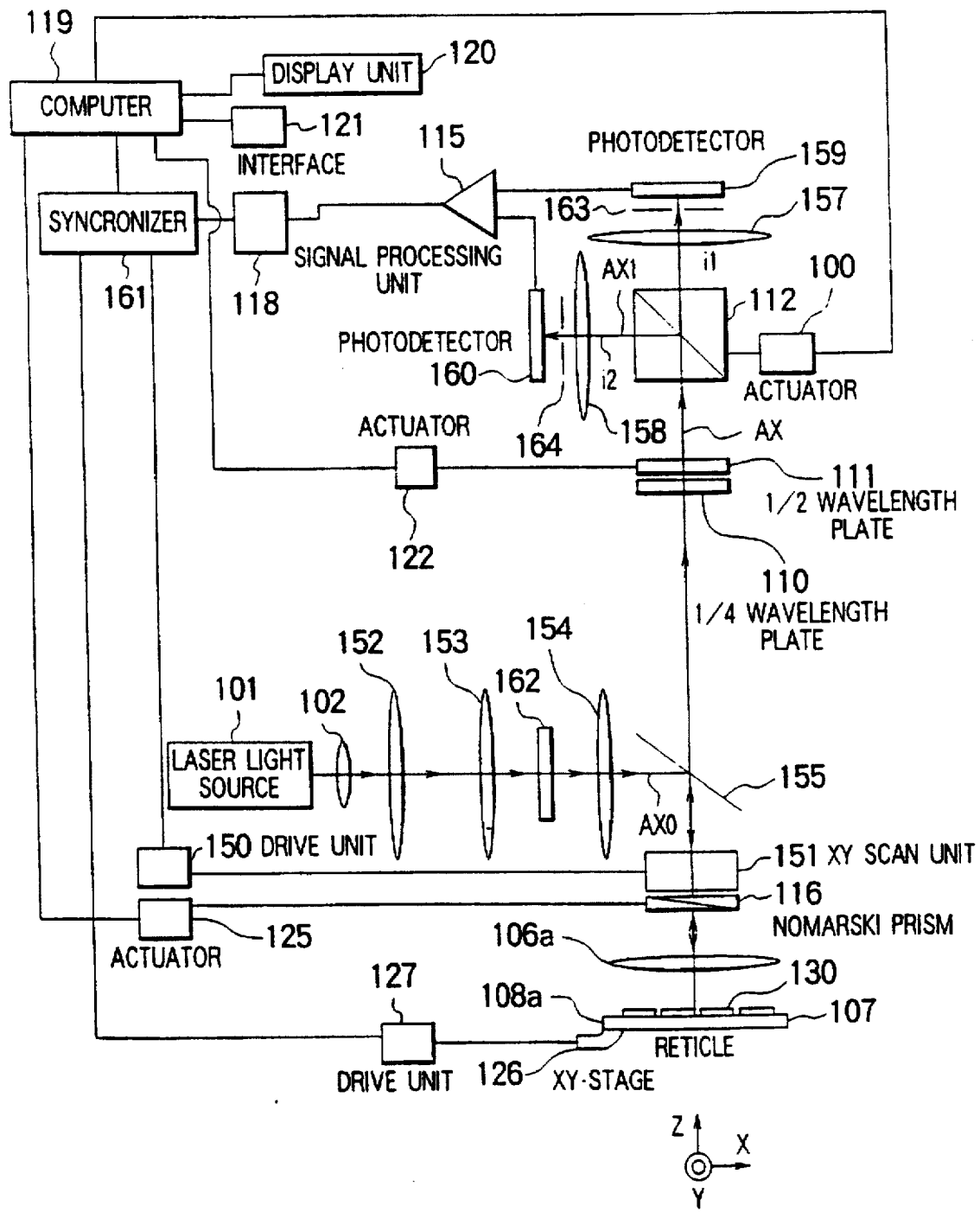
FIG. 23 is a block diagram schematically showing a configuration of a defect inspection apparatus as a twentieth embodiment in accordance with the observation apparatus of the present invention.

As shown FIG. 23, the defect inspection apparatus according to the nineteenth embodiment of the present invention differs from the nineteenth embodiment in the position of an X-Y scanning section 151. The same reference numerals as in FIG. 22 denote the same members in FIG. 23, and a detailed description thereof will be omitted.

In this embodiment, a light beam reflected by a reticle 108a passes through the X-Y scanning section 151 again. That is, this apparatus has the optical arrangement of a confocal microscope. Light beams incident on two photoelectric conversion devices 159 and 160 are always stationary independently of the scanning position on the reticle 108a. These light beams are converged by two imaging lenses 157 and 158. Two pinholes 163 and 164 are set at the convergence points (points conjugate to the target inspection surface on the reticle 108a), thereby decreasing unnecessary light (flare and the like).

Without being restricted to the foregoing embodiments, the present invention can be modified in various manners.

Figure 24:
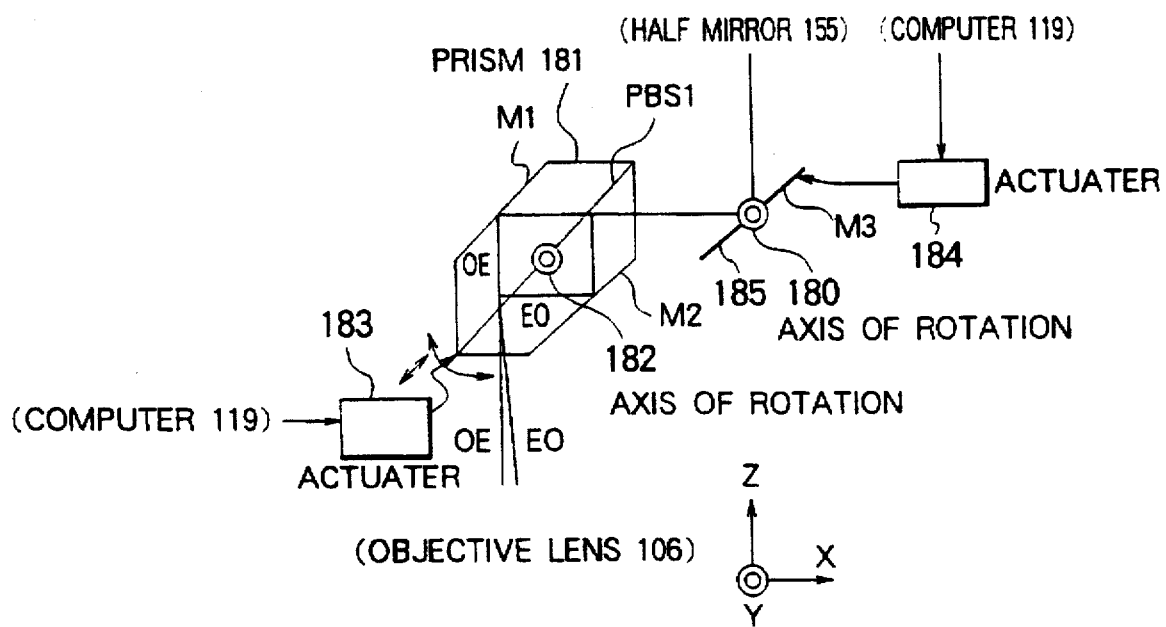
FIG. 24 is a block diagram schematically showing a configuration of a first modification according to the embodiments shown in FIGS. 1–23.

For example, as shown in FIG. 24, a first modification according to the foregoing embodiments replaces the Nomarski prisms 5, 36, 105, 116 in the above embodiments with a prism having a polarizing beam splitter plane. Other constituent elements are the same as those of the above embodiments, and only the prism portion having the polarizing beam splitter plane will be described. For the descriptive convenience, the Nomarski prism 116 and the actuator 125 of the above embodiments are replaced with devices a reflecting mirror 185, a prism 181, and two actuators 183 and 184.

In the defect inspection apparatus of this modification, a light beam from a laser light source 101 is reflected by a half mirror 155 and incident on the reflecting mirror 185. The light beam reflected by the reflecting mirror 185 is incident on the prism 181. The prism 181 comprises two reflecting surfaces M1 and M2 and a polarizing beam splitter surface PBS1. These surfaces are perpendicular to the paper surface. The polarizing beam splitter surface PBS1 transmits a linearly polarized light beam having a plane of polarization parallel to the paper surface and reflects a linearly polarized light beam having a plane of polarization perpendicular to the paper surface. The reflecting surface M1 and the polarizing beam splitter surface PBS1 are parallel to each other. The reflecting surface M2 and the polarizing beam splitter surface PBS1 are parallel to each other or have a small angle (e.g., several degrees) therebetween. The prism 181 can be rotated about a rotational axis 182 extending to the Y direction by the actuator 183 and can also be moved along a direction parallel to the polarizing beam splitter surface PBS1 and the paper surface. The actuator 183 is also controlled by a computer 119.

The prism 181 has the same function as that of a Nomarski prism. More specifically, the prism 181 separates an incident light beam into two light beams OE and EO having planes of polarization perpendicular to each other at a slight angle (separation angle). The two light beams OE and EO are incident on a reticle 108a through a condenser lens 106a to form two spots slightly shifted from each other on the reticle 108a. The two light beams OE and EO are reflected by the reticle 108a and propagate back along the optical path as one light beam. The light beam emerges from the prism 181.

When the prism 181 is rotated about a rotational axis 182 by the actuator 183, the shear amount can be changed. In addition, when the prism 181 is moved along a direction parallel to the polarizing beam splitter surface PBS1 and the paper surface (a direction perpendicular to the optical axis of the objective lens 106a), the phase difference between the two light beams can be adjusted. When the mirror 185 is rotated about the rotational axis 180 extending to the Y direction by the actuator 184 in accordance with rotation of the prism 181 such that the reflecting surface M3 of the mirror 185 is always parallel to the polarizing beam splitter plane PBS1, movement of one light beam can be suppressed, and only the other light beam can be moved. The actuator 184 is also controlled by the computer 119.

In this manner, the prism 181 can adjust the shear amount (a shift amount on the reticle 108a) and the initial phase difference amount of the two light beams, so that the prism 181 can be treated like a Nomarski prism. Therefore, the arrangement and function except the light beam separating means or the light beam synthesizing means are the same as those of the above embodiments and pose no problem.

Figure 25:
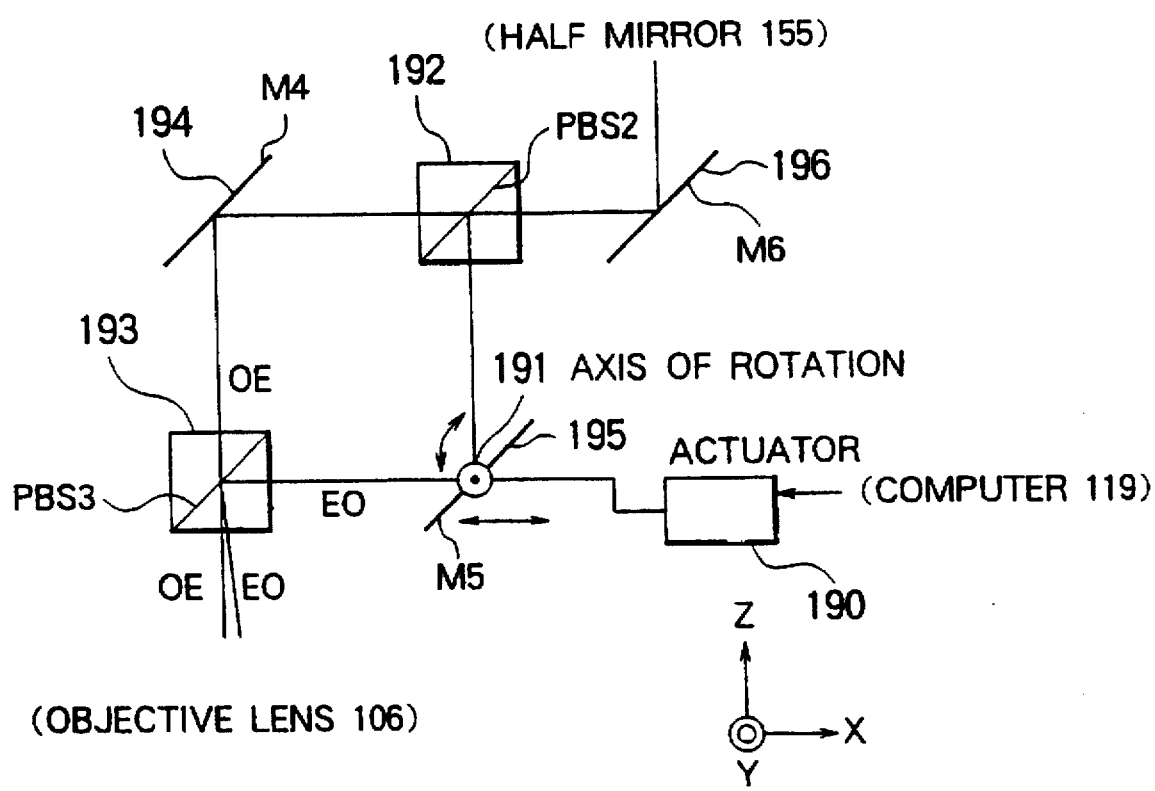
FIG. 25 is a block diagram schematically showing a configuration of a second modification according to the embodiments shown in FIGS. 1–23.

Also, as shown in FIG. 25, a second modification according to the foregoing embodiments replaces the Nomarski prisms 5, 36, 105, 116 in the above embodiments with two prisms having polarizing beam splitter planes. For the descriptive convenience, in this modification as well, the Nomarski prism 116 and the actuator 125 of the above embodiments are replaced with three reflecting mirrors 194 to 196, two polarizing beam splitters 192 and 193, and an actuator 190.

In the defect inspection apparatus of this modification, in place of a Nomarski prism, the two mirrors 194 and 195 respectively having two reflecting mirror M4 and M5, and the two prism 192, 193 respectively having two polarizing beam splitter planes PBS2 and PBS3 are used to constitute a light beam separating means (or a light beam synthesizing means). The two polarizing beam splitter surfaces PBS2 and PBS3 and the reflecting surfaces M4 and M5 are perpendicular to the paper surface. The polarizing beam splitter surfaces PBS2 and PBS3 and the reflecting surface M4 are parallel to each other. The mirror 195 can be rotated about a rotational axis 191 perpendicular to the paper surface by the actuator 190 which is controlled by the computer 119. The entire optical system or part (e.g., only the mirrors) of this optical system can also be translated along the X direction by the actuator 190. Here, the mirror 196 having a reflecting surface M6 is disposed in the optical path between the half mirror 155 and the prism 192.

The two polarizing beam splitter surfaces PBS2 and PBS3 transmit a linearly polarized light beam having a plane of polarization parallel to the paper surface and reflect a linearly polarized light beam having a plane of polarization perpendicular to the paper surface. Therefore, an illumination light beam reflected by the mirror 196 is polarized and separated by the polarizing beam splitter surface PBS1 into light beams OE and EO having planes of polarization perpendicular to each other. The two light beams OE and EO are reflected by the reflecting mirrors 194 and 195, respectively. The light beam OE is transmitted through the polarizing beam splitter surface PBS2. The light beam EO is reflected by the polarizing beam splitter surface PBS2. These light beams propagate toward a condenser lens 106a. When the reflecting mirror 195 is inclined by a small angle with respect to the rotational axis 191, the light beam EO is made to emerge from the polarizing beam splitter surface PBS2 while having a small angle with respect to the light beam OE. Therefore, a shear amount 2δ of the two light beams after transmission through the objective lens 106a can be arbitrarily adjusted. In addition, when the reflecting mirror 191 is moved along the X direction by the actuator 190, the initial phase difference amount between the two light beams OE and EO can be adjusted.

As described above, two polarizing beam splitters and two plane mirrors can be used in place of a Nomarski prism, and the same function as that of a Nomarski prism can be obtained.

Also, as the two-dimensional scanners in the first to fourth embodiments and the fourteenth, the nineteenth, and the twentieth embodiments, such means as vibrating mirror, rotary polygon mirror, and acousto-optic devices have been known. However, it is needless to mention that, without being restricted to these known means, other appropriate deflecting members may also be used as the two-dimensional scanner.

Also, though a laser beam is spatially deflected in the two-dimensional scanner in the first to third embodiments and the fourteenth, the nineteenth, and the twentieth embodiments, the stage may be two-dimensionally scanned.

Also, the first to fourth embodiments and the twentieth embodiment are configured such that the reflected light from the object is transmitted through the two-dimensional scanner again so as to make the laser beam stand still in the air and incident on the half mirror. However, such a configuration is not essential in the present invention. The reflected light may not travel through the two-dimensional scanner to-and-fro when each of the ¼-wavelength plate, ½-wavelength plate, polarizing beam splitter, and photodetector has an opening sufficient for transmitting or receiving the reflected light from the object without blocking it, while the amount of displacement of the laser beam caused by scanning is suppressed to such an extent that the operations of the ¼-wavelength plate, ½-wavelength plate, and polarizing beam splitter as polarizing devices are not remarkably deteriorated.

Also, in the first, second, fifth, and eighth embodiments and the fourteenth to the twentieth embodiments, the analyzer angle of the fixed polarizing beam splitter is changed upon the operation of the ½-wavelength plate which is rotatable around the optical axis. However, without being restricted to the ½-wavelength plate, such azimuth rotator as Faraday rotor using magneto-optic effect and azimuth rotator using electro-optic effect may also be used as the analyzer having a polarization rotating effect. Further, it is needless to mention that, when the polarizing beam splitter and the two photodetectors are unitedly rotatable around the optical axis, the azimuth rotator such as ½-wavelength plate which can variably rotate polarization may be omitted. For examples, as shown in the FIG. 17, FIG. 19, FIG. 22, and FIG. 23, an actuator 100 which is controlled by the computer 119, rotates the polarizing beam splitter 112 around the optical axis of the objective lens 106.

Also, the above-mentioned embodiments are configured such that the linearly polarized laser beam is incident on the ¼-wavelength plate when a mirror surface is observed. However, the ¼-wavelength plate can be omitted when the inserting position of the Nomarski prism with respect to the optic axis or the like is defined such that the Nomarski prism imparts a phase difference of π multiplied by an integer to two light components, which have been split by the Nomarski prism, as they travel therethrough to-and-fro so as to turn the laser beam into circularly polarized light before it reaches the ¼-wavelength plate.

Also, while the first to thirteenth embodiments explain a microscope which is of a type detecting the reflected light from the sample object, they may be configured so as to detect the light transmitted through the sample. In this case, the laser light source, collimator lens, two-dimensional scanner, Nomarski prism, and objective lens are disposed so as to illuminate the sample object with light from the rear side thereof. Further, another objective lens and Nomarski prism are disposed in the optical path of the light transmitted through the sample.

Also, in the fourteenth to twentieth embodiments, the circuit pattern on the reticle is drawn by a shifter. Even a foreign substance (semi-transparent foreign substance) as a phase object on the reticle on which a circuit pattern formed of a light-shielding film of chromium or the like (or a circuit pattern formed of a light-shielding film of chromium or the like and a circuit pattern formed of a shifter) is drawn can be detected in a similar manner.

When the light beam separating means (e.g., a Nomarski prism) can be arranged near the pupil of the objective lens, the two linearly polarized light beams preferably have a small angle therebetween. At other positions, a device for separating the light beam in parallel can be used. The setting position can be appropriately selected in accordance with the optical design of the optical system such as an objective lens and the light beam separating means (e.g., a Nomarski prism) to be used.

Further, in the fifth to thirteenth embodiments and the sixteenth to eighteenth embodiments, using the combination of a polarizer and a ¼-wavelength plate adjacent to the polarizer, the phase difference between the two linearly polarized light beams separated by the Nomarski prism 116 can be adjusted by rotating the polarizer, as in a case wherein the Nomarski prism 116 is moved.

In the foregoing embodiments, the analyzer angle of the analyzer, azimuth of the ¼-wavelength plate, and the like are represented by their typical values. It is needless to mention, however, that these angles include all the angles which are equivalent thereto based on the periodicity of angle-dependent functions.

As explained in the foregoing, the present invention can realize a differential type differential interference microscope which, with respect to any level difference, can arbitrarily change the contrast of its differential interference image. According to the contrast-adjusting function of the present invention, not only any level difference can be observed with the maximum contrast but also the contrast for level differences which are less important to the observer can be minimized such that only the remaining desired level differences are observed. Thus, the function of the present invention to selectively observe the level differences become quite powerful in defect testing for IC patterns or the like, testing for dust, and so forth.

Also, the present invention can realize a level-difference measuring apparatus which calculates the phase difference caused by a level difference on the basis of the analyzer angle at which the difference signal S is maximized or minimized and the amplitude reflectances on both sides of the level difference and, based on thus calculated phase difference caused by the level difference, determines the level difference.

Also, the present invention can realize a level-difference measuring apparatus which calculates the phase difference $\Psi$ on the basis of a relational expression, which is dependent on the change in amplitude reflectance, between the difference signal S and the phase difference $\Psi$ caused by a level difference and, based on thus calculated phase difference $\Psi$, determines the level difference.

Accordingly, the present invention can realize a level-difference measuring apparatus which, even when the light reflectivity changes between both sides of a level difference, can measure any level difference with a high accuracy.

Further, the present invention can realize a defect inspection apparatus which inspects, for all reticles including a conventional reticle having a circuit pattern formed of a chromium light-shielding film, a halftone reticle on which a circuit pattern is drawn by only a phase shifter formed of a thin transparent film, and a reticle with phase shifters, which has both phase shifters and a chromium pattern, the presence/absence of an abnormality in the amount of phase shift of a phase shifter portion or a foreign substance as a transparent phase object.

The present invention can provide a defect inspection apparatus capable of inspecting both the presence/absence of an abnormality in the phase shift amount of a phase shifter portion and the presence/absence of a foreign substance as a transparent phase object for these reticles. In addition, a defect inspection apparatus using a differential interference microscope capable of changing the contrast of a differential interference image can be realized. With this apparatus, the contrast of an unnecessary circuit pattern can be minimized, and only the image of a defect can be observed.

Furthermore, a differential interference microscope capable of changing the contrast of a differential interference image can be obtained. With this microscope, the contrast of an unnecessary sample can be minimized, and only the image of a necessary sample can be observed.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Applications No. 188509/1995 filed on Jun. 30, 1995, No. 188510/1995 filed on Jun. 30, 1995, No. 188511/1995 filed on Jun. 30, 1995, No. 215580/1995 filed on Aug. 24, 1995, No. 217915/1995 filed on Aug. 25, 1995, No. 301579/1995 filed on Nov. 20, 1995, and No. 301580/1995 filed on Nov. 20, 1995 are hereby incorporated by reference.

What is claimed is:

1. An observation apparatus comprising:

a light source for generating light;

a separating optical system which splits the light emitted from said light source into two different polarized light beams;

a condenser optical system which converges the two polarized light beams emitted from said separating optical system so as to respectively form light spots on two different positions on a sample object;

a polarization selecting means, which has a predetermined analyzer angles, for selecting a specific polarized light component from composite light made of the two polarized light beams reflected by or transmitted through said sample object;

light detecting means for detecting the polarized light component selected by said polarization selecting means; and phase difference adjustment means for adjusting a phase difference between the two polarized light beams reflected by or transmitted through said sample object to provide a circularly polarized light by composing the two polarized light beams to said polarization selecting means, when said sample object does not modulate both the phase and amplitude of the light incident thereon.

2. An observation apparatus according to claim 1, further comprising a scanning device for scanning said sample object with the two light spots thereon which are split by said separating optical system, wherein said light source generates spatially coherent light and guides thus generated light to said separating optical system.

3. An observation apparatus according to claim 2, wherein said light source generates linearly polarized light having a predetermined direction of polarization; wherein, when said sample object is a light reflecting member having a mirror surface, said phase difference adjustment means imparts a phase difference of $\pi$ multiplied by an integer to the two polarized light beams split by said separating optical system and then reflected by said sample object, as said two polarized light beams travel through said separating optical system to-and-fro, and wherein said phase difference adjustment means includes a ¼-wavelength plate which converts the linearly polarized light emitted from said separating optical system into the circularly polarized light.

4. An observation apparatus according to claim 2, wherein said light source generates linearly polarized light having a predetermined direction of polarization; and wherein, when said sample object is a light reflecting member having a mirror surface, said phase difference adjustment means imparts a phase difference of $\pi/2$ multiplied by an odd number to the two polarized light beams split by said separating optical system and then reflected by said sample object, as said two polarized light beams travel through said separating optical system to-and-fro.

5. An observation apparatus according to claim 2, further comprising a synthesizing optical system which combines the two polarized light beams transmitted through said sample object and guides the composite light to said polarization selecting means, wherein said light source generates linearly polarized light having a predetermined direction of polarization; wherein, when said sample object is optically flat, said phase difference adjustment means imparts a phase difference of $\pi$ multiplied by an integer to the two polarized light beams split by said separating optical system and then transmitted through said sample object, and wherein said phase difference adjustment means includes a ¼-wavelength plate which converts the linearly polarized light emitted from said synthesizing optical system into the circularly polarized light.

6. An observation apparatus according to claim 2, further comprising a synthesizing optical system which combines the two polarized light beams transmitted through said sample object and guides the composite light to said polarization selecting means, wherein said light source generates linearly polarized light having a predetermined direction of polarization; and wherein, when said sample object is optically flat, said phase difference adjustment means imparts a phase difference of $\pi/2$ multiplied by an odd number to the two polarized light beams split by said separating optical system and then transmitted through said sample object.

7. An observation apparatus according to claim 1, further comprising an illumination optical system which is disposed between said light source and said separating optical system and illuminates said sample object with the light thereon emitted from said light source by way of said separating optical system, wherein said light detecting means is constituted by a two-dimensional image sensor disposed on at least one of respective focal planes of said condenser optical system.

8. An observation apparatus according to claim 7, wherein said illumination optical system includes a wavelength selecting means for selecting a specific wavelength component from the light emitted from said light source.

9. An observation apparatus according to claim 7, wherein said illumination optical system includes a polarized light selecting means for selecting a specific linear polarized light component from the light emitted from said light source.

10. An observation apparatus according to claim 9, wherein, when said sample object is a light reflecting member having a mirror surface, said phase difference adjustment means imparts a phase difference of $\pi$ multiplied by an integer to the two polarized light beams split by said separating optical system and then reflected by said sample object, as said two polarized light beams travel through said separating optical system to-and-fro, and wherein said phase difference adjustment means includes a ¼-wavelength plate which converts the linearly polarized light emitted from said separating optical system into the circularly polarized light.

11. An observation apparatus according to claim 9, wherein, when said sample object is a light reflecting member having a mirror surface, said phase difference adjustment means imparts a phase difference of $\pi/2$ multiplied by an odd number to the two polarized light beams split by said separating optical system and then reflected by said sample object, as said two polarized light beams travel through said separating optical system to-and-fro.

12. An observation apparatus according to claim 9, further comprising a synthesizing optical system which combines the two polarized light beams transmitted through said sample object and guides the composite light to said polarization selecting means, wherein, when said sample object is optically flat, said phase difference adjustment means imparts a phase difference of $\pi$ multiplied by an integer to the two polarized light beams split by said separating optical system and then transmitted through said sample object, and wherein said polarization selecting means includes a ¼-wavelength plate which converts the linearly polarized light emitted from said synthesizing optical system into the circularly polarized light.

13. An observation apparatus according to claim 9, further comprising a synthesizing optical system which combines the two polarized light beams transmitted through said sample object and guides the composite light to said polarization selecting means, wherein, when said sample object is optically flat, said phase difference adjustment means imparts a phase difference of π/2 multiplied by an odd number to the two polarized light beams split by said separating optical system and then transmitted through said sample object.

14. An observation apparatus according to claim 1, wherein said condenser optical system is arranged so as to serve as an objective optical system which collects the two polarized light beams reflected by said sample object, and said separating optical system is arranged so as to serve as a synthesizing optical system which combines the two polarized light beams again exited from said condenser optical system and guides the composite light to said polarization selecting means.

15. An observation apparatus according to claim 14, wherein said separating optical system includes a birefringence prism.

16. An observation apparatus according to claim 14, wherein said separating optical system includes a prism having two reflecting surfaces non-parallel to each other, and a polarizing beam splitter surface disposed between said two reflecting surfaces and parallel to either of said two reflecting surfaces.

17. An observation apparatus according to claim 14, wherein said separating optical system includes two mirrors having respective reflecting surfaces non-parallel to each other, and two prisms disposed between said two mirrors and having respective polarizing beam splitter surfaces parallel to either of said reflecting surfaces of two reflecting mirrors.

18. An observation apparatus according to claim 14, wherein said phase difference adjustment means comprises a driving member capable of moving said separating optical system.

19. An observation apparatus according to claim 1, further comprising an objective optical system which collects the two polarized light beams transmitted through said sample object, and a synthesizing optical system which combines the two polarized light beams exited from said objective optical system and guides the composite light to said polarization selecting means.

20. An observation apparatus according to claim 19, wherein at least one of said separating optical system and said synthesizing optical system includes a birefringence prism.

21. An observation apparatus according to claim 19, wherein at least one of said separating optical system and said synthesizing optical system includes a prism having two reflecting surfaces non-parallel to each other, and a polarizing beam splitter surface disposed between said two reflecting surfaces and parallel to either of said two reflecting surfaces.

22. An observation apparatus according to claim 19, wherein at least one of said separating optical system and said synthesizing optical system includes two mirrors having respective reflecting surfaces non-parallel to each other, and two prisms disposed between said two mirrors and having respective polarizing beam splitter surfaces parallel to either of said reflecting surfaces of two reflecting mirrors.

23. An observation apparatus according to claim 19, wherein said phase difference adjustment means comprises a driving member capable of moving at least one of said separating optical system and said synthesizing optical system.

24. An observation apparatus according to claim 1, further comprising a measuring means for quantitatively measuring, based on an output of said light detecting means, a level difference on said sample object; wherein said polarization selecting means includes a polarizing beam splitter which splits the composite light composed of the two polarized light beams emitted from said sample object into two different directions; wherein said light detecting means includes a first photodetector for detecting the polarized light transmitted through said polarizing beam splitter and a second photodetector for detecting the polarized light reflected by said polarizing beam splitter; wherein said measuring means measures the level difference of said sample object based on a relationship which is established between an output difference in said first and second photodetectors for the level difference of said sample object and a phase difference in the two polarized light beams caused by the level difference of said sample object, while depending on change in an amplitude reflectance between two regions holding the level difference of said sample object therebetween.

25. An observation apparatus according to claim 24, wherein the analyzer angle of said polarization selecting means is set to nπ/4 as the analyzer angle of said polarizing beam splitter wherein n is an odd number.

26. An observation apparatus according to claim 24, wherein said measuring means measures the level difference of said object sample based on a phase difference Ψ between the two polarized light beams calculated by the following relationship:

$$\sin \Psi = D \cdot S / (W_a^{1/2} \cdot W_b^{1/2})$$

wherein Ψ is the phase difference between the two polarized light beams caused by the level difference of said sample object, S is an output difference between said first and second photodetectors, $W_a$ is an output sum of said first and second photodetectors for one of two regions holding the level difference of said sample object therebetween reflecting amplitude reflectance of said region, $W_b$ is an output sum of said first and second photodetectors for the other of the two regions holding the level difference of said sample object therebetween reflecting amplitude reflectance of said other region, and D is a constant depending on said apparatus as a whole.

27. An observation apparatus according to claim 1, further comprising a measuring means for quantitatively measuring, based on an output of said light detecting means, a level difference on said sample object; wherein said polarization selecting means variably sets the analyzer angle with respect to the composite light composed of the two polarized light beams reflected by or transmitted through said sample object; wherein said measuring means measures the level difference of the sample object based on a relationship which is established between an output difference in said light detecting means for the level difference of said sample object when two different analyzer angles for said polarization selecting means are respectively set and a phase difference in the two polarized light beams caused by the level difference of said sample object, while depending on change in amplitude reflectance between two regions holding the level difference of said sample object therebetween.

28. An observation apparatus according to claim 27, said polarization selecting means includes a polarizing plate which is disposed so as to be rotatable around an optical axis of said condenser optical system.

29. An observation apparatus according to claim 27, wherein said polarization selecting means includes a liquid crystal polarizer which changes a refractive index distribution thereof based on a voltage signal externally applied thereto.

30. An observation apparatus according to claim 27, wherein the analyzer angles of said polarization selecting means are set to $n\pi/4$ and $(n/4+m/2)\pi$, respectively, wherein n and m are odd numbers.

31. An observation apparatus according to claim 27, wherein said measuring means measures a level difference of the object surface based on a phase difference $\Psi$ between the two polarized light beams calculated by the following relationship:

$$\sin \Psi = D \cdot S/(W_a^{1/2} \cdot W_b^{1/2})$$

wherein $\Psi$ is the phase difference between the two polarized light beams caused by the level difference of said sample object, S is an output difference in said light detecting means when two analyzer angles for said polarization selecting means are set, $W_a$ is an output sum of said light detecting means for one of two regions holding the level difference of said sample object therebetween reflecting amplitude reflectance of this region, $W_b$ is an output sum of said light detecting means for the other of the two regions holding the level difference of said sample object therebetween reflecting amplitude reflectance of said other region, and D is a constant depending on said apparatus as a whole.

32. An observation apparatus according to claim 1, further comprising a measuring means for quantitatively measuring, based on an output of said light detecting means, a level difference on said sample object; wherein said polarization selecting means variably sets the analyzer angle with respect to the composite light composed of the two polarized light beams reflected by or transmitted through said sample object and includes a polarizing beam splitter which splits said composite light into two different directions; wherein said light detecting means includes a first photodetector for detecting light transmitted through said polarizing beam splitter and a second photodetector for detecting light reflected by said polarizing beam splitter; and wherein said measuring means measures the level difference of said sample object based on the analyzer angle which is set so as to maximize or minimize the output difference between said first and second photodetectors for the level difference of said sample object.

33. An observation apparatus according to claim 32, wherein said polarizing beam splitter is fixed around an optical axis of said condenser optical system and wherein said polarization selecting means includes an azimuth rotator disposed on an inlet side of said polarizing beam splitter, said azimuth rotator having a variable polarization rotational angle.

34. An observation apparatus according to claim 33, wherein said azimuth rotator is constituted by a ½-wavelength plate disposed so as to be rotatable around the optical axis of said condenser optical system.

35. An observation apparatus according to claim 32, wherein each of said polarizing beam splitter and said first and second photodetectors is disposed so as to be rotatable around the optical axis of said condenser lens.

36. An observation apparatus according to claim 32, wherein an analyzer angle $\phi_{min}$ of said polarization selecting means when the output difference between said first and second photodetectors for the level difference of said sample object is minimum, coincides with $\phi_{max} + n\pi/4$, wherein $\phi_{max}$ is an analyzer angle of said polarization selecting means when the output difference between said first and second photodetectors for the level difference of said sample object is maximum, and n is an odd number.

37. An observation apparatus according to claim 32, wherein said measuring means measures a level difference of said object sample based on a phase difference $\Psi$ between the two polarized light beams calculated by the following relationship:

$$\tan 2\phi = -2a \cdot b \cdot \sin \Psi/(a^2 - b^2)$$

wherein $\phi$ is the analyzer angle of said polarization selecting means when the output difference between said first and second photodetectors for the level difference of said sample object is maximum, $\Psi$ is the phase difference between the two polarized light beams caused by the level difference of said sample object, a is an amplitude reflectance of one of two regions holding the level difference of said sample object therebetween incorporated in an output sum of said light detecting means for said region, and b is an amplitude reflectance of the other of two regions holding the level difference of said sample object therebetween incorporated in an output sum of said light detecting means for said other region.

38. An observation apparatus according to claim 1, further comprising a measuring means for quantitatively measuring, based on an output of said light detecting means, a level difference on said sample object; wherein said polarization selecting means variably sets the analyzer angle with respect to the composite light composed of the two polarized light beams reflected by or transmitted through said sample object and wherein said measuring means measures the level difference of said sample object based on two different analyzer angles which are set so as to maximize or minimize the output difference between said light detecting means for the level difference of said sample object.

39. An observation apparatus according to claim 38, wherein said polarization selecting means includes a polarizing plate which is disposed so as to be rotatable around the optical axis of said condenser optical system.

40. An observation apparatus according to claim 38, wherein said polarization selecting means includes a liquid crystal polarizer which changes a refractive index distribution thereof based on a voltage signal externally applied thereto.

41. An observation apparatus according to claim 38, wherein a difference in the two analyzer angles of said polarization selecting means is set to $n\pi/4$, wherein n is an odd number.

42. An observation apparatus according to claim 38, wherein said measuring means measures a level difference of said object sample based on a phase difference $\Psi$ between the two polarized light beams calculated by the following relationship:

$$\tan 2\phi = -2a \cdot b \cdot \sin \Psi/(a^2 - b^2)$$

wherein $\phi$ is the analyzer angle of said polarization selecting means when $\Psi$ is the phase difference between the two polarized light beams caused by the level difference of said sample object, a is an amplitude reflectance of one of two regions holding the level difference of said sample object therebetween incorporated in an output sum of said light detecting means for said region and b is an amplitude reflectance of the other of the two regions holding the level difference of said sample object therebetween incorporated in an output sum of said light detecting means for said other region when the two analyzer angles for said polarization selecting means are respectively set to $\phi$ and $\phi + \pi/2$ so that the output difference between said light detecting means for the level difference of said sample object is maximum, or when the two analyzer angles for said polarization selecting means are respectively set to φ+π/4 and φ+3π/4 so that the output difference between said light detecting means for the level difference of said sample object is minimum.

43. An observation apparatus according to claim 1, further comprising an image forming means which forms a differential interference image of said sample object based on an output of said light detecting means; wherein said polarization selecting means variably sets the analyzer angle with respect to the composite light composed of the two polarized light beams reflected by or transmitted through said sample object and includes a polarizing beam splitter which splits said composite light into two different directions; wherein said light detecting means includes a first photodetector for detecting light transmitted through said polarizing beam splitter and a second photodetector for detecting light reflected by said polarizing beam splitter; and wherein said image forming means generates, based on an output difference between said first and second photodetectors for the level difference of said sample object, a contrast corresponding to the analyzer angle of said polarization selecting means for the differential interference image of said sample object.

44. An observation apparatus according to claim 43, wherein said polarizing beam splitter is fixed around an optical axis of said condenser optical system and wherein said polarization selecting means includes an azimuth rotator which is disposed on an inlet side of said polarizing beam splitter, said azimuth rotator having a variable polarization rotational angle.

45. An observation apparatus according to claim 44, wherein said azimuth rotator is constituted by a ½-wavelength plate disposed so as to be rotatable around the optical axis of said condenser optical system.

46. An observation apparatus according to claim 43, wherein each of said polarizing beam splitter and said first and second photodetectors is disposed so as to be rotatable around the optical axis of said condenser optical system.

47. An observation apparatus according to claim 43, wherein the analyzer angle of said polarization selecting means is set to nπ/4 wherein n is an odd number.

48. An observation apparatus according to claim 1, further comprising an image forming means which forms a differential interference image of said sample object based on an output of said light detecting means; wherein said polarization selecting means variably sets the analyzer angle with respect to the composite light composed of the two polarized light beams reflected by or transmitted through said sample object; wherein said image forming means generates, based on an output difference in said light detecting means for the level difference of said sample object when two different analyzer angles for said polarization selecting means are respectively set, a contrast corresponding to the analyzer angle of said polarization selecting means for the differential interference image of said sample object.

49. An observation apparatus according to claim 48, wherein said polarization selecting means includes a polarizing plate which is disposed so as to be rotatable around the optical axis of said condenser optical system.

50. An observation apparatus according to claim 48, wherein said polarization selecting means includes a liquid crystal polarizer which changes a refractive index distribution thereof based on a voltage signal externally applied thereto.

51. An observation apparatus according to claim 48, wherein a difference in the two analyzer angles of said polarization selecting means is set to nπ/4, wherein n is an odd number.

52. An observation apparatus according to claim 1, further comprising a defect detection system which detects the defect formed on a substrate being said sample object on the basis of an output from said light detecting means, wherein said polarization selecting means variably sets the analyzer angle with respect to the composite light composed of the two polarized light beams emitted from said sample object and includes a polarizing beam splitter which splits said composite light into two different directions; wherein said light detecting means includes a first photodetector for detecting light transmitted through said polarizing beam splitter and a second photodetector for detecting light reflected by said polarizing beam splitter, and wherein said defect detecting means shows the defects as the differential interference image of said sample object generated with a contrast corresponding to the analyzer angle of said polarization selecting means, based on an output difference between said first and second photodetectors.

53. An observation apparatus according to claim 52, wherein said light source emits a linearly polarized light beam having a wavelength of light for which a phase shift of π multiplied by an integer is caused by a transparent substance constituting a predetermined pattern on said substrate or a wavelength substantially equal to a wavelength of light used to expose said predetermined pattern.

54. An observation apparatus according to claim 52, wherein said defect detection system comprises a differential circuit which generates a difference signal as the difference of two output signals respectively input from said first and second photodetectors, corresponding the two different polarized light beams selected by said polarization selecting means, a binaring circuit which compares the difference signal from said differential circuit with a predetermined threshold value thereby generating a binary signal, and a judging circuit which detects the defects formed on the substrate on the basis of the binary signal from said binaring circuit.

55. An observation apparatus according to claim 52, wherein said polarizing beam splitter is fixed around an optical axis of said condenser optical system and wherein said polarization selecting means includes an azimuth rotator which is disposed on an inlet side of said polarizing beam splitter, said azimuth rotator having a variable polarization rotational angle.

56. An observation apparatus according to claim 55, wherein said azimuth rotator is constituted by a ½-wavelength plate disposed so as to be rotatable around the optical axis of said condenser optical system.

57. An observation apparatus according to claim 52, wherein each of said polarizing beam splitter and said first and second photodetectors is disposed so as to be rotatable around the optical axis of said condenser optical system.

58. An observation apparatus according to claim 52, wherein the analyzer angle of said polarization selecting means is set to nπ/4 wherein n is an odd number.

59. An observation apparatus according to claim 1, further comprising a defect detection system which detects the defect formed on a substrate being said sample object on the basis of an output from said light detecting means, wherein said polarization selecting means variably sets the analyzer angle with respect to the composite light composed of the two polarized light beams emitted from said sample object, and wherein said defect detecting means shows the defects as the differential interference image of said sample object generated with a contrast corresponding to the analyzer angle of said polarization selecting means, based on an output difference in said light detecting means when two different analyzer angles for said polarization selecting means are respectively set.

60. An observation apparatus according to claim 59, wherein said light source emits a linearly polarized light beam having a wavelength of light for which a phase shift of $\pi$ multiplied by an integer is caused by a transparent substance constituting a predetermined pattern on said substrate or a wavelength substantially equal to a wavelength of light used to expose said predetermined pattern.

61. An observation apparatus according to claim 59, wherein said defect detection system comprises a differential circuit which generates a difference signal as the difference of two output signals sequentially input from said light detecting means, corresponding the two different polarized light beams selected by said polarization selecting means when two different analyzer angles for said polarization selecting means are respectively set, a binaring circuit which compares the difference signal from said differential circuit with a predetermined threshold value thereby generating a binary signal, and a judging circuit which detects the defects formed on the substrate on the basis of the binary signal from said binaring circuit.

62. An observation apparatus according to claim 59, wherein said polarization selecting means comprises an analyzer rotatable about an optical axis of said condenser optical system.

63. An observation apparatus according to claim 62, further comprising an azimuth rotator which is disposed between said light source and said substrate, and having a variable polarization rotational angle.

64. An observation apparatus according to claim 63, wherein said azimuth rotator is constituted by a ½-wavelength plate disposed so as to be rotatable around the optical axis of said condenser optical system.

65. An observation apparatus according to claim 66, further comprising an actuator which rotates said azimuth rotator around the optical axis of said condenser optical system, wherein said actuator changes an azimuth of said azimuth rotator by 45° when said polarization selecting means changes selecting either of the two different polarized light components.

66. An observation apparatus according to claim 62, further comprising a polarizer which is disposed between said light source and is rotatable about the optical axis of said condenser optical system.

67. An observation apparatus according to claim 63, further comprising an actuator which rotates said polarizer around the optical axis of said condenser optical system, wherein said actuator changes an azimuth of said polarizer by 90° when said polarization selecting means changes selecting either of the two different polarized light components.

68. An observation apparatus according to claim 61, wherein the two analyzer angles of said polarization selecting means are set to $n\pi/4$ and $(n/4+m/2)\pi$, respectively, wherein n and m are odd numbers.

69. An observation apparatus comprising:
a light source for generating light;
a separating optical system which splits the light emitted from said light source into two different polarized light beams;
a condenser optical system which converges the two polarized light beams emitted from said separating optical system so as to respectively form light spots on two different positions on a sample object;
a polarization selecting means, which includes an azimuth rotator having a variable polarization rotational angle, for variably setting an analyzer angle by said azimuth rotator and selecting a specific polarized light component from composite light made of the two polarized light beams reflected by or transmitted through said sample object;
light detecting means for detecting the polarized light component selected by said polarization selecting means; and
phase difference adjustment means for adjusting a phase difference between the two polarized light beams reflected by or transmitted through said sample object to provide a circularly polarized light by composing the two polarized light beams to said polarization selecting means, when said sample object does not modulate both phase and amplitude of the light incident thereon.

70. An observation apparatus according to claim 69, further comprising a scanning device for scanning said sample object with the two light spots thereon which are split by said separating optical system, wherein said light source generates spatially coherent light and guides thus generated light to said separating optical system.

71. An observation apparatus according to claim 70, wherein said light source generates linearly polarized light having a predetermined direction of polarization; wherein, when said sample object is a light reflecting member having a mirror surface, said phase difference adjustment means imparts a phase difference of $\pi$ multiplied by an integer to the two polarized light beams split by said separating optical system and then reflected by said sample object, as said two polarized light beams travel through said separating optical system to-and-fro, and wherein said phase difference adjustment means includes a ¼-wavelength plate which converts the linearly polarized light emitted from said separating optical system into the circularly polarized light.

72. An observation apparatus according to claim 70, wherein said light source generates linearly polarized light having a predetermined direction of polarization; and wherein, when said sample object is a light reflecting member having a mirror surface, said phase difference adjustment means imparts a phase difference of $\pi/2$ multiplied by an odd number to the two polarized light beams split by said separating optical system and then reflected by said sample object, as said two polarized light beams travel through said separating optical system to-and-fro.

73. An observation apparatus according to claim 70, further comprising a synthesizing optical system which combines the two polarized light beams transmitted through said sample object and guides the composite light to said polarization selecting means, wherein said light source generates linearly polarized light having a predetermined direction of polarization; wherein, when said sample object is optically flat, said phase difference adjustment means imparts a phase difference of $\pi$ multiplied by an integer to the two polarized light beams split by said separating optical system and then transmitted through said sample object, and wherein said phase difference adjustment means includes a ¼-wavelength plate which converts the linearly polarized light emitted from said synthesizing optical system into the circularly polarized light.

74. An observation apparatus according to claim 70, further comprising a synthesizing optical system which combines the two polarized light beams transmitted through said sample object and guides the composite light to said polarization selecting means, wherein said light source generates linearly polarized light having a predetermined direction of polarization; and wherein, when said sample object is optically flat, said phase difference adjustment means imparts a phase difference of π/2 multiplied by an odd number to the two polarized light beams split by said separating optical system and then transmitted through said sample object.

75. An observation apparatus according to claim 69, further comprising an illumination optical system which is disposed between said light source and said separating optical system and illuminates said sample object with the light thereon emitted from said light source by way of said separating optical system, wherein said light detecting means is constituted by a two-dimensional image sensor disposed on at least one of respective focal planes of said condenser optical system.

76. An observation apparatus according to claim 75, wherein said illumination optical system includes a wavelength selecting means for selecting a specific wavelength component from the light emitted from said light source.

77. An observation apparatus according to claim 75, wherein said illumination optical system includes a polarized light selecting means for selecting a specific linear polarized light component from the light emitted from said light source.

78. An observation apparatus according to claim 77, wherein, when said sample object is a light reflecting member having a mirror surface, said phase difference adjustment means imparts a phase difference of π multiplied by an integer to the two polarized light beams split by said separating optical system and then reflected by said sample object, as said two polarized light beams travel through said separating optical system to-and-fro, and wherein said phase difference adjustment means includes a ¼-wavelength plate which converts the linearly polarized light emitted from said separating optical system into the circularly polarized light.

79. An observation apparatus according to claim 77, wherein, when said sample object is a light reflecting member having a mirror surface, said phase difference adjustment means imparts a phase difference of π/2 multiplied by an odd number to the two polarized light beams split by said separating optical system and then reflected by said sample object, as said two polarized light beams travel through said separating optical system to-and-fro.

80. An observation apparatus according to claim 77, further comprising a synthesizing optical system which combines the two polarized light beams transmitted through said sample object and guides the composite light to said polarization selecting means, wherein, when said sample object is optically flat, said phase difference adjustment means imparts a phase difference of π multiplied by an integer to the two polarized light beams split by said separating optical system and then transmitted through said sample object, and wherein said polarization selecting means includes a ¼-wavelength plate which converts the linearly polarized light emitted from said synthesizing optical system into the circularly polarized light.

81. An observation apparatus according to claim 77, further comprising a synthesizing optical system which combines the two polarized light beams transmitted through said sample object and guides the composite light to said polarization selecting means, wherein, when said sample object is optically flat, said phase difference adjustment means imparts a phase difference of π/2 multiplied by an odd number to the two polarized light beams split by said separating optical system and then transmitted through said sample object.

82. An observation apparatus according to claim 69, wherein said condenser optical system is arranged so as to serve as an objective optical system which collects the two polarized light beams reflected by said sample object, and said separating optical system is arranged so as to serve as a synthesizing optical system which combines the two polarized light beams again exited from said condenser optical system and guides the composite light to said polarization selecting means.

83. An observation apparatus according to claim 82, wherein said separating optical system includes a birefringence prism.

84. An observation apparatus according to claim 82, wherein said separating optical system includes a prism having two reflecting surfaces non-parallel to each other, and a polarizing beam splitter surface disposed between said two reflecting surfaces and parallel to either of said two reflecting surfaces.

85. An observation apparatus according to claim 82, wherein said separating optical system includes mirrors having respective reflecting surfaces non-parallel to each other, and two prisms disposed between said two mirrors and having respective polarizing beam splitter surfaces parallel to either of said reflecting surfaces of two reflecting mirrors.

86. An observation apparatus according to claim 82, wherein said phase difference adjustment means comprises a driving member capable of moving said separating optical system.

87. An observation apparatus according to claim 69, further comprising an objective optical system which collects the two polarized light beams transmitted through said sample object, and a synthesizing optical system which combines the two polarized light beams exited from said objective optical system and guides the composite light to said polarization selecting means.

88. An observation apparatus according to claim 87, wherein at least one of said separating optical system and said synthesizing optical system includes a birefringence prism.

89. An observation apparatus according to claim 87, wherein at least one of said separating optical system and said synthesizing optical system includes a prism having two reflecting surfaces non-parallel to each other, and a polarizing beam splitter surface disposed between said two reflecting surfaces and parallel to either of said two reflecting surfaces.

90. An observation apparatus according to claim 87, wherein at least one of said separating optical system and said synthesizing optical system includes two mirrors having respective reflecting surfaces non-parallel to each other, and two prisms disposed between said two mirrors and having respective polarizing beam splitter surfaces parallel to either of said reflecting surfaces of two reflecting mirrors.

91. An observation apparatus according to claim 87, wherein said phase difference adjustment means comprises a driving member capable of moving at least one of said separating optical system and said synthesizing optical system.

92. An observation apparatus according to claim 69, wherein said polarization selecting means variably sets the analyzer angle with respect to the composite light composed of the two polarized light beams reflected by or transmitted through said sample object and includes a polarizing beam splitter which splits said composite light into two different directions; and wherein said light detecting means includes a first photodetector for detecting light transmitted through said polarizing beam splitter and a second photodetector for detecting light reflected by said polarizing beam splitter.

93. An observation apparatus according to claim 92, wherein said polarizing beam splitter is fixed around an optical axis of said condenser optical system and wherein said azimuth rotator is disposed on an inlet side of said polarizing beam splitter.

94. An observation apparatus according to claim 92, wherein said azimuth rotator is constituted by a ½-wavelength plate disposed so as to be rotatable around the optical axis of said condenser optical system.

95. An observation apparatus according to claim 92, wherein each of said polarizing beam splitter and said first and second photodetectors is disposed so as to be rotatable around the optical axis of said condenser optical system.

96. An observation apparatus according to claim 92, wherein an analyzer angle $\phi_{min}$ of said polarization selecting means when the output difference between said first and second photodetectors for the level difference of said sample object is minimum, coincides with $\phi_{max}+n\pi/4$, wherein $\phi_{max}$ is an analyzer angle of said polarization selecting means when the output difference between said first and second photodetectors for the level difference of said sample object is maximum, and n is an odd number.

97. An observation apparatus according to claim 92, further comprising a measuring means for quantitatively measuring, based on an output of said light detecting means, a level difference on said sample object, wherein said measuring means measures the level difference of said sample object based on the analyzer angle which is set so as to maximize or minimize the output difference between said first and second photodetectors for the level difference of said sample object.

98. An observation apparatus according to claim 97, wherein said measuring means measures a level difference of said object sample based on a phase difference $\Psi$ between the two polarized light beams calculated by the following relationship:

$$\tan 2\phi = -2a\cdot b\cdot\sin \Psi/(a^2-b^2)$$

wherein $\phi$ is the analyzer angle of said polarization selecting means when the output difference between said first and second photodetectors for the level difference of said sample object is maximum, $\Psi$ is the phase difference between the two polarized light beams caused by the level difference of said sample object, a is an amplitude reflectance of one of two regions holding the level difference of said sample object therebetween incorporated in an output sum of said light detecting means for said region, and b is an amplitude reflectance of the other of two regions holding the level difference of said sample object therebetween incorporated in an output sum of said light detecting means for said other region.

99. An observation apparatus according to claim 92, further comprising an image forming means which forms a differential interference image of said sample object based on an output of said light detecting means, wherein said image forming means generates, based on an output difference between said first and second photodetectors for the level difference of said sample object, a contrast corresponding to the analyzer angle of said polarization selecting means for the differential interference image of said sample object.

100. An observation apparatus according to claim 92, further comprising a defect detection system which detects the defect formed on a substrate being said sample object on the basis of an output from said light detecting means, wherein said defect detecting means shows the defects as the differential interference image of said sample object generated with a contrast corresponding to the analyzer angle of said polarization selecting means, based on an output difference between said first and second photodetectors.

101. An observation apparatus according to claim 100, wherein said light source emits a linearly polarized light beam having a wavelength of light for which a phase shift of $\pi$ multiplied by an integer is caused by a transparent substance constituting a predetermined pattern on said substrate or a wavelength substantially equal to a wavelength of light used to expose said predetermined pattern.

102. An observation apparatus according to claim 100, wherein said defect detection system comprises a differential circuit which generates a difference signal as the difference of two output signals respectively input from said first and second photodetectors, corresponding the two different polarized light beams selected by said polarization selecting means, a binaring circuit which compares the difference signal from said differential circuit with a predetermined threshold value thereby generating a binary signal, and a judging circuit which detects the defects formed on the substrate on the basis of the binary signal from said binaring circuit.

103. An observation apparatus comprising:

a light source for generating light;

a separating optical system for splitting the light emitted from the light source into two different polarized light beams;

a condenser optical system for converging the two polarized light beams emitted from the separating optical system so as to respectively form light spots on two different positions on a sample object;

a polarization selecting means having a predetermined analyzer angle for selecting a specific polarized light component from composite light made of the two polarized light beams reflected by or transmitted through the sample object;

light detecting means for detecting the polarized light component selected by the polarization selecting means; and phase difference setting means for setting a phase difference between the two polarized light beams reflected by or transmitted through the sample object to provide a circularly polarized light by composing the two polarized light beams to the polarization selecting means, when the sample object does not modulate both phase and amplitude of the light incident thereon.

104. An observation apparatus comprising:

a light source for generating light;

a separating optical system for splitting the light emitted from the light source into two different polarized light beams;

a condenser optical system for converging the two polarized light beams emitted from the separating optical system so as to respectively form light spots on two different positions on a sample object;

a polarization selecting means, including an azimuth rotator having a variable polarization rotational angle, for variably setting an analyzer angle and selecting a specific polarized light component from composite light made of the two polarized light beams reflected by or transmitted through the sample object;

light detecting means for detecting the polarized light component selected by the polarization selecting means; and phase difference setting means for setting a phase difference between the two polarized light beams reflected by or transmitted through the sample object to provide a circularly polarized light by composing the two polarized light beams to the polarization selecting means, when the sample object does not modulate both phase and amplitude of the light incident thereon.

* * * * *